United States Patent
Tiernan et al.

(10) Patent No.: US 12,018,288 B2
(45) Date of Patent: Jun. 25, 2024

(54) ENGINEERED PRODUCER CELL LINES AND METHODS OF MAKING AND USING THE SAME

(71) Applicant: Ultragenyx Pharmaceutical Inc., Novato, CA (US)

(72) Inventors: Aubrey R. Tiernan, Somerville, MA (US); Nicholas Richards, Arlington, MA (US)

(73) Assignee: Ultragenyx Pharmaceutical Inc., Novato, CA (US)

(*) Notice: Subject to any disclaimer, the term of this patent is extended or adjusted under 35 U.S.C. 154(b) by 899 days.

(21) Appl. No.: 16/844,475

(22) Filed: Apr. 9, 2020

(65) Prior Publication Data

US 2020/0325455 A1    Oct. 15, 2020

Related U.S. Application Data

(60) Provisional application No. 62/979,483, filed on Feb. 21, 2020, provisional application No. 62/839,207, filed on Apr. 26, 2019, provisional application No. 62/833,548, filed on Apr. 12, 2019.

(51) Int. Cl.
| | | |
|---|---|---|
| C07H 21/04 | (2006.01) | |
| C12N 7/00 | (2006.01) | |
| C12N 15/11 | (2006.01) | |
| C12N 15/86 | (2006.01) | |
| C12Q 1/6869 | (2018.01) | |

(52) U.S. Cl.
CPC .............. *C12N 7/00* (2013.01); *C12N 15/11* (2013.01); *C12N 15/86* (2013.01); *C12Q 1/6869* (2013.01); *C12N 2310/14* (2013.01); *C12N 2310/315* (2013.01); *C12N 2310/321* (2013.01); *C12N 2750/14143* (2013.01); *C12N 2750/14152* (2013.01)

(58) Field of Classification Search
None
See application file for complete search history.

(56) References Cited

U.S. PATENT DOCUMENTS

| | | |
|---|---|---|
| 5,387,484 A | 2/1995 | Doany et al. |
| 5,658,785 A | 8/1997 | Johnson |
| 5,688,676 A | 11/1997 | Zhou et al. |
| 5,691,176 A | 11/1997 | Lebkowski et al. |
| 5,741,683 A | 4/1998 | Zhou et al. |
| 6,156,303 A | 12/2000 | Russell et al. |
| 6,846,665 B1 | 1/2005 | Hörer et al. |
| 7,510,872 B2 | 3/2009 | Clark et al. |
| 8,163,543 B2 | 4/2012 | Urabe et al. |
| 8,188,060 B2 | 5/2012 | Khvorova et al. |
| 8,409,842 B2 | 4/2013 | Clark et al. |
| 10,035,985 B2 | 7/2018 | Zhao et al. |
| 10,137,188 B2 | 11/2018 | Karpilow et al. |
| 2002/0081721 A1 | 6/2002 | Allen et al. |
| 2016/0319277 A1 | 11/2016 | Shiloach et al. |
| 2019/0083554 A1 | 3/2019 | Morrison et al. |
| 2019/0290710 A1 | 9/2019 | Jing et al. |
| 2020/0032221 A1 | 1/2020 | Tiernan et al. |
| 2020/0048641 A1 | 2/2020 | Jing et al. |
| 2020/0124505 A1 | 4/2020 | Panteli et al. |
| 2020/0340013 A1 | 10/2020 | Li et al. |

FOREIGN PATENT DOCUMENTS

| | | |
|---|---|---|
| WO | WO-1996/17947 A1 | 6/1996 |
| WO | WO-2000/24916 A1 | 5/2000 |
| WO | WO-2000/47757 A1 | 8/2000 |
| WO | WO-2015/114365 A1 | 8/2015 |
| WO | WO-2017/172772 A1 | 10/2017 |
| WO | WO-2018/013705 A1 | 1/2018 |
| WO | WO-2018/071817 A1 | 4/2018 |
| WO | WO-2018/175773 A1 | 9/2018 |
| WO | WO-2018/175775 A1 | 9/2018 |
| WO | WO-2018/208960 A1 | 11/2018 |
| WO | WO-2020/219543 A1 | 10/2020 |

OTHER PUBLICATIONS

Inwood et al., "Methods for using small non-coding RNAs to improve recombinant protein expression in mammalian cells," Genes, 2018, 9(25): 1-14.

Shiloach (2016) "Genome-wide RNAi screen for improved functional expression of recombinant proteins from HEK 293 cells," in "Cell Culture Engineering XV," Robert Kiss, Genentech Sarah Harcum, Clemson University Jeff Chalmers, Ohio State University Eds, ECI Symposium Series, (2016). https://dc.engconfintl.org/cellculture_xv/68 (2 pages).

Clark et al., "Cell lines for the production of recombinant adeno-associated virus", Human Gene Therapy. vol. 6, (1995), pp. 1329-1341.

Conway et al., "High-titer recombinant adeno-associated virus production utilizing a recombinant herpes simplex virus type I vector expressing AAV-2 rep and cap", Gene Therapy. vol. 6, No. 6, (1999), pp. 986-993. Druz et al. "A novel microRNA mmu-miR-466h affects apoptosis regulation in mammalian cells," Biotechnol Bioeng, 2011, 108(7): 1651-1661.

Druz et al. "Stable inhibition of mmu-miR-466h-5p improves apoptosis resistance and protein production in CHO cells," Metab Eng. 2013, 16(1): 87-94.

Grieger et al., "Production of recombinant adeno-associated virus vectors using suspension HEK293 cells and continuous harvest of vector from the culture media for GMP FIX and FLT1 clinical vector", American Society of Gene & Cell Therapy. vol. 24, (2016), pp. 287-297.

(Continued)

*Primary Examiner* — Kimberly Chong
(74) *Attorney, Agent, or Firm* — Goodwin Procter LLP

(57) ABSTRACT

This application relates to recombinant adeno-associated virus (rAAV) packaging and/or producer cell lines which have been engineered to reduce expression and/or activity of one or more genes and/or proteins to increase rAAV titers. The methods of generating the engineered cell lines have also been described herein.

17 Claims, 13 Drawing Sheets
Specification includes a Sequence Listing.

(56) References Cited

OTHER PUBLICATIONS

Hermonat et al., "Human papillomavirus type 16 helper functions for adeno-associated virus type 2 replication", Molecular therapy. vol. 9,(2004), S289-290.

Martin et al., "Generation and Characterization of Adeno-Associated Virus Producer Cell Lines for Research and Preclinical Vector Production", Human Gene Therapy Methods. vol. 24, (2013), pp. 253-269.

Richards et al. "An RNAseq Directed Screening Method to Identify Genes Modulating Titer in rAAV Producing Cell Lines," ASGCT 22nd Annual Meeting. Washington. DC., Apr. 29, 2019.

Strobel et al., "Comparative Analysis of Cesium Chloride- and Iodixanol-Based Purification of Recombinant Adeno-Associated Viral Vectors for Preclinical Applications", Human Gene Therapy Methods. vol. 26, No. 4, (2015), pp. 147-157.

Tamosaitis et al., "Meta-Analysis of Publicly Available Chinese Hamster Ovary (CHO) Cell Transcriptomic Datasets for Identifying Engineering Targets to Enhance Recombinant Protein Yields", Biotechnology Journal. vol. 13, (2018), pp. 1-12.

Thorne et al., Characterizing clearance of helper adenovirus by a clinical rAAV1 manufacturing process. Biologicals, vol. 36, Issue 1, (2008), pp. 7-18.

Thorne et al., "Manufacturing recombinant adeno-associated viral vectors from producer cell clones", Human Gene Therapy. vol. 20, (2009), pp. 707-714.

Virag et al., "Producing Recombinant Adeno-Associated Virus in Foster Cells: Overcoming Production Limitations Using a Baculovirus-Insect Cell Expression Strategy", Human Gene Therapy. vol. 20, No. 8 (2009), pp. 807-817.

Wang et al., "Identification of an adeno-associated virus binding epitope for AVB sepharose affinity resin", Molecular Therapy—Methods and Clinical Development. vol. 2, (2015), pp. 1-6.

Weitzman et al., "Adeno-associated virus biology", Adeno-Associated Virus: Methods and Protocols, Methods in Molecular Biology, vol. 807, (2011), pp. 1-23.

Wright et al., "Identification of factors that contribute to recombinant AAV2 particle aggregation and methods to prevent its occurrence during vector purification and formulation", Molecular Therapy, vol. 12, No. 1, (2005), pp. 171-178.

Wright, "Review: Transient Transfection Methods for Clinical Adeno-Associated Viral Vector Production", Human Gene Therapy. vol. 20, (2009), pp. 698-706.

Xiao et al. "MiRNA mimic screen for improved expression of functional neurotensin receptor from HEK293 cells," Biotechnol Bioeng, 2015, 112(8): 1632-1643.

Xiao et al."Genome-scale RNA interference screen identifies antizyme 1 (OAZ1) as a target for improvement of recombinant protein production in mammalian cells," Biotechnol Bioeng. 2016, 113(11): 2403-2415.

Zhen et al., "Infectious titer assay for adeno-associated virus vectors with sensitivity sufficient to detect single infectious events", Human Gene Therapy. vol. 15, (2004), pp. 709-715.

Clark et al., "Highly purified recombinant adeno-associated virus vectors are biologically active and free of detectable helper and wild-type viruses," Hum Gene Ther. (1999) 10(6):1031-1039 (24 pages).

Gao et al. (2004) "Clades of Adeno-Associated Viruses Are Widely Disseminated in Human Tissues," Journal of Virology 78(12):6381-6388.

Han et al. (2015) "Advanced Applications of RNA Sequencing and Challenges," Bioinformatics and Biology Insights, 9:29-46.

International Search Report and Written Opinion for corresponding International Application No. PCT/US2020/027489 dated Aug. 12, 2020 (18 pages).

Lock et al. (2013) "Absolute Determination of Single-Stranded and Self-Complementary Adeno-Associated Viral Vector Genome Titers by Droplet Digital PCR," 25(2):115-125.

Ozsolak et al. (2011) "RNA sequencing: advances, challenges and opportunities," Nature Reviews Genetics 12(2):87-98 (20 pages).

Samulski et al. (1989) "Helper-Free Stocks of Recombinant Adeno-Associated Viruses: Normal Integration Does Not Require Viral Gene Expression," Journal of Virology 63(9):3822-3828.

Shangary et al. (2009) "Small-Molecule Inhibitors of the MDMS-p53 Protein-Protein Interaction to Reactivate p53 Function: A Novel Approach for Cancer Therapy," Annual Review of Pharmacology and Toxicology 49:223-241 (19 pages).

Sommer JM et al., "Quantification of adeno-associated virus particles and empty capsids by optical density measurement," Mol Ther. Jan. 2003;7(1):122-8.

Srivastava (2008) "Adeno-associated virus-mediated gene transfer," J. Cell Biochem. 105(1):17-24 (12 pages).

Stifani Satkunanathan et al. (2014) "Establishment of a Novel Cell Line for the Enhanced Production of Recombinant Adeno-Associated Virus Vectors for Gene Therapy," Human Gene Therapy 25(11):929-941 (14 pages).

Wright JF (2009) "Transient transfection methods for clinical adeno-associated viral vector production," Hum Gene Ther. Jul.;20(7):698-706.

De Vries, W. et al., "Increased virus replication in mammalian cells by blocking intracellular innate defense responses," Gene Ther 15:545-552 (2008).

Wang, Z. et al., "RNA-Seq: a revolutionary tool for transcriptomics," Nat Rev Genet 10, 57-63 (2009) (16 pages).

Shiloach, Presentation "Investigating the ability to improve expression of recombinant protein from mammalian cells by utilizing non-coding RNAs: microRNA and siRNA" Biotechnology Core Laboratory, National Institute of Diabetes and Digestive and Kidney Diseases (29 slides), 2022.

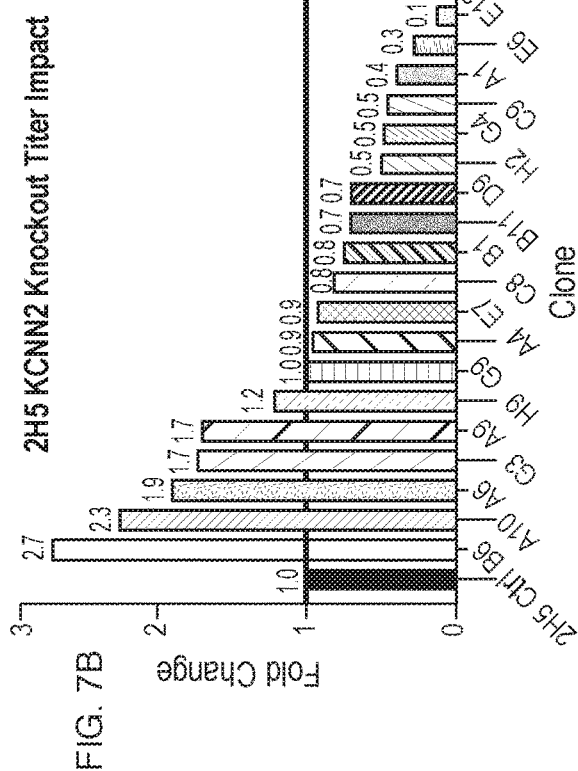
FIG. 7A
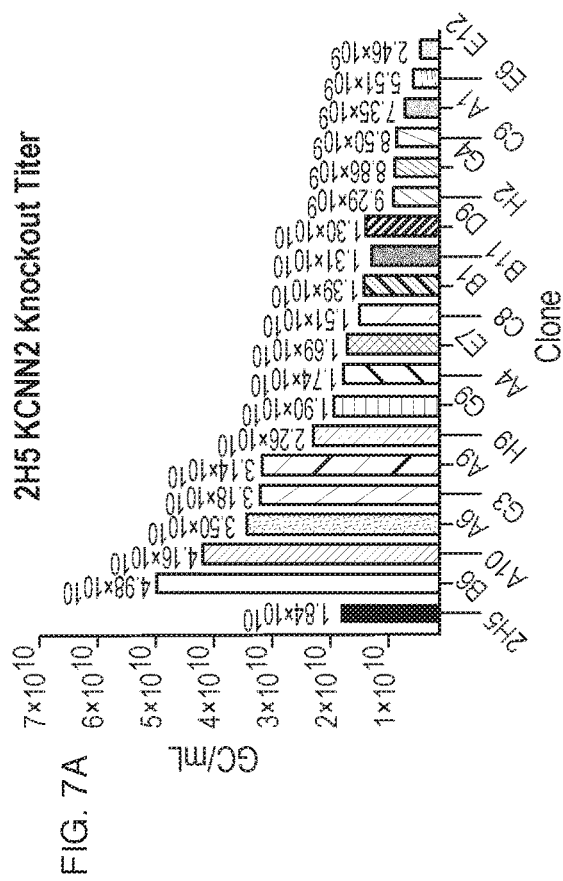
FIG. 7B
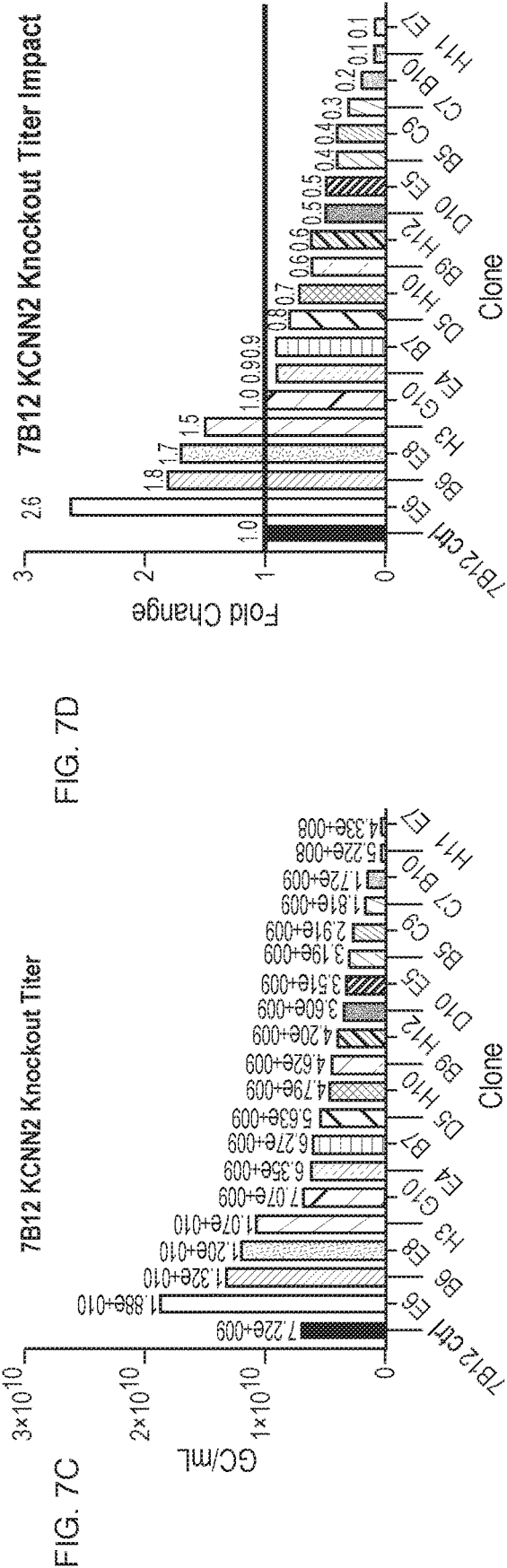
FIG. 7C
FIG. 7D

SEQUENCE LISTING

<160> NUMBER OF SEQ ID NOS: 59

<210> SEQ ID NO 1
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 1
gcaacagcgu aaaaauugut t                                              21

<210> SEQ ID NO 2
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 2
cgguguccac aguccuugat t                                              21

<210> SEQ ID NO 3
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 3
caagaaaagu uauaaguuut t                                              21

<210> SEQ ID NO 4
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 4
cggaggaagu uacagaugut t                                              21

<210> SEQ ID NO 5
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 5
agaugcaaga gguaccaaat t                                              21

<210> SEQ ID NO 6
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 6
ggugucggau gauuuaucat t                                              21

<210> SEQ ID NO 7
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 7
gaagcuagaa cuuaccaaat t                                              21

<210> SEQ ID NO 8
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 8
ggaugucuuu ccuaggagat t                                              21

<210> SEQ ID NO 9
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 9
cgcucaucga caauaauuat t                                              21

<210> SEQ ID NO 10
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 10
cacuuuagau guaucuaaut t                                              21

<210> SEQ ID NO 11
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 11
ggagcauaaa guagaccgat t                                              21

<210> SEQ ID NO 12
<211> LENGTH: 20
<212> TYPE: RNA
<213> ORGANISM: Artificial Sequence
<220> FEATURE:
<223> OTHER INFORMATION: Synthetic oligonucleotide

<400> SEQUENCE: 12
uugccacuac agcuaccacc                                                20

<210> SEQ ID NO 13
<211> LENGTH: 20
<212> TYPE: RNA
<213> ORGANISM: Artificial Sequence
<220> FEATURE:
<223> OTHER INFORMATION: Synthetic oligonucleotide

<400> SEQUENCE: 13
ccaauguacu cagggaaaca                                                20

```
<210> SEQ ID NO 14
<211> LENGTH: 20
<212> TYPE: RNA
<213> ORGANISM: Artificial Sequence
<220> FEATURE:
<223> OTHER INFORMATION: Synthetic oligonucleotide

<400> SEQUENCE: 14
aguccaccaa aguguuugcu                                                   20

<210> SEQ ID NO 15
<211> LENGTH: 20
<212> TYPE: RNA
<213> ORGANISM: Artificial Sequence
<220> FEATURE:
<223> OTHER INFORMATION: Synthetic oligonucleotide

<400> SEQUENCE: 15
aaaggagucu gcuuacuuac                                                   20

<210> SEQ ID NO 16
<211> LENGTH: 20
<212> TYPE: DNA
<213> ORGANISM: Homo sapiens

<400> SEQUENCE: 16
ttgccactac agctaccacc                                                   20

<210> SEQ ID NO 17
<211> LENGTH: 20
<212> TYPE: DNA
<213> ORGANISM: Homo sapiens

<400> SEQUENCE: 17
ccaatgtact cagggaaaca                                                   20

<210> SEQ ID NO 18
<211> LENGTH: 20
<212> TYPE: DNA
<213> ORGANISM: Homo sapiens

<400> SEQUENCE: 18
agtccaccaa agtgtttgct                                                   20

<210> SEQ ID NO 19
<211> LENGTH: 20
<212> TYPE: DNA
<213> ORGANISM: Homo sapiens

<400> SEQUENCE: 19
aaaggagtct gcttacttac                                                   20

<210> SEQ ID NO 20
<211> LENGTH: 20
<212> TYPE: DNA
<213> ORGANISM: Homo sapiens

<400> SEQUENCE: 20
cttctcgtaa tggcagatct                                                   20

<210> SEQ ID NO 21
<211> LENGTH: 20
<212> TYPE: DNA
<213> ORGANISM: Homo sapiens
```

```
<400> SEQUENCE: 21
gcacttgagg atcttgcacg                                              20

<210> SEQ ID NO 22
<211> LENGTH: 20
<212> TYPE: DNA
<213> ORGANISM: Homo sapiens

<400> SEQUENCE: 22
gaggtcctct atgccatgga                                              20

<210> SEQ ID NO 23
<211> LENGTH: 20
<212> TYPE: DNA
<213> ORGANISM: Homo sapiens

<400> SEQUENCE: 23
ccatacccat ccatccagct                                              20

<210> SEQ ID NO 24
<211> LENGTH: 20
<212> TYPE: DNA
<213> ORGANISM: Homo sapiens

<400> SEQUENCE: 24
cccatgtgaa ggaccttcaa                                              20

<210> SEQ ID NO 25
<211> LENGTH: 20
<212> TYPE: DNA
<213> ORGANISM: Homo sapiens

<400> SEQUENCE: 25
gttcttcaaa ctctgttcgg                                              20

<210> SEQ ID NO 26
<211> LENGTH: 20
<212> TYPE: DNA
<213> ORGANISM: Homo sapiens

<400> SEQUENCE: 26
gaaggcgtag acttatctga                                              20

<210> SEQ ID NO 27
<211> LENGTH: 20
<212> TYPE: DNA
<213> ORGANISM: Homo sapiens

<400> SEQUENCE: 27
agccaacttc cagcaccaat                                              20

<210> SEQ ID NO 28
<211> LENGTH: 20
<212> TYPE: DNA
<213> ORGANISM: Homo sapiens

<400> SEQUENCE: 28
gggcaatgga ccttctgcct                                              20

<210> SEQ ID NO 29
<211> LENGTH: 20
<212> TYPE: DNA
```

<213> ORGANISM: Homo sapiens

<400> SEQUENCE: 29
ggctgcgggg cagagggcaa                                           20

<210> SEQ ID NO 30
<211> LENGTH: 20
<212> TYPE: DNA
<213> ORGANISM: Homo sapiens

<400> SEQUENCE: 30
cgggcaggct gcggggcaga                                           20

<210> SEQ ID NO 31
<211> LENGTH: 20
<212> TYPE: DNA
<213> ORGANISM: Homo sapiens

<400> SEQUENCE: 31
acgggcaggc tgcggggcag                                           20

<210> SEQ ID NO 32
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 32
acaauuuuua cgcuguugcc a                                         21

<210> SEQ ID NO 33
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 33
ucaaggacug uggacaccgg t                                         21

<210> SEQ ID NO 34
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 34
aaacuuauaa cuuuucuugg a                                         21

<210> SEQ ID NO 35
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 35
acaucuguaa cuuccuccgc a                                         21

<210> SEQ ID NO 36
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 36
uuugguaccu cuugcaucuc a                                              21

<210> SEQ ID NO 37
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 37
ugauaaauca uccgacacct g                                              21

<210> SEQ ID NO 38
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 38
uuugguaagu ucuagcuucc t                                              21

<210> SEQ ID NO 39
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 39
ucuccuagga aagacaucca a                                              21

<210> SEQ ID NO 40
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 40
uaauuauugu cgaugagcgg c                                              21

<210> SEQ ID NO 41
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 41
auuagauaca ucuaaagugg g                                              21

<210> SEQ ID NO 42
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 42
ucggucuacu uuaugcucct t                                              21

<210> SEQ ID NO 43
<211> LENGTH: 3610
<212> TYPE: DNA
<213> ORGANISM: Homo sapiens

<400> SEQUENCE: 43

```
cttcctgcgg ctgaaccgcc cggctgagcc gacattgccg gcgtcttggc gattcggccc      60
gacgagctcc gctttcgcta cagcatggtg gcctactgga gacaggctgg actcagctac     120
atccgatact cccagatctg tgcaaaagca gtgagagatg cactgaagac agaattcaaa     180
gcaaatgctg agaagacttc tggcagcaac gtaaaaattg tgaaagtaaa gaaggaataa     240
tctaccctga ctaaagcttg aaatgctaca tttccaaggt gaagatgtgt gggcacatgt     300
tatggcagat tgaaaaggat ctcattccat gggaaaaaaa aaaatcctgt cttgttcata     360
aattgacaat gtcaataaat tgaaatatgg ttcactgtta ctcttgattt tagtttgtga     420
gactttttca ttttctttaa ggaactgtc tgcacagctg catgattatg ccatgtgaa      480
ccagggtttc ttaaaagcag gggaagccag atttaatatt tagtgaccaa agggatacag     540
aaagcatttt gaaatgtctc aaaatagtt gtttcatgac attaattggt gatcaaaatt      600
atctgctgtc attgaggctt cgtagtccct tatttttgaa ttgttgtcat gtcagaataa     660
tgacatggtt atcagtaaca aatggaaata attattaaat actaaaagtg tagattagaa     720
gaagaaatac taaattgtac ttgttttgta ttgtgcactt aaagcctata gataagaacg     780
gttacagaat ttaagcacaa agtgtttttc acattgtttt gtaaatgaat ctttatactc     840
tggtagcatt tctcatagga aatgaggcaa agctattgaa taacttgctc attgagttga     900
tggccaaact gaaattaaaa cctaggagtt ttgactgcaa gtctgggaca cggtgaccac     960
aacagcagtt tcgtggtatt tccatagtga ttcattcatt cattatttag ggatgaaaaa    1020
ttgttgcaag ttatgttttt atctttcttt gaaacttgaa agggcttggg caagtaaaac    1080
accattgcaa agttaactgc ctgatttaa ctgttttgg agactggaga ataaaatttg      1140
aactggaaat tttgaaacac cattctagga tcagttctca catggtactt aagctcacaa    1200
tgatttatca gggccactgt cagcaatgcc aggataagc cgaaaagaac atctttgttc     1260
tcggcttctg ggaatgactt attgtcccga cacttgacct gtaggtttta ctgaattctc    1320
agcacagagc gagcagggag gcagagccaa ttgagtggaa gagggtgcct ctggaaaaca    1380
gcaggttagg agcccttgga gtcctccgcc tcggagctgt catcctgctg ttggcaagtt    1440
agggcacctc agttcagtgc tgtggccccc aagattaagg tactaggaag tatcctccat    1500
tacagggaac aggaataaat gaatcaaaaa gctatcgggc cttttgaca tgggacgaat     1560
aaagtaacta ataggcaaag gggctaaatg atttccagtc aagtaattag agataagtca    1620
tttattaagg aggcagatgg ggtattattg gtatatagat ggcatagtag attgctagta    1680
tattggtaga ttattggtat atagatggta tgttaaggag gcagatgggg tattactggt    1740
atatagatgg tatggtagat tggtagtata ttggcagatt attggtatat ggtatgttga    1800
ggcagatggg gtattactgg tatatagatg gcatagtaga ttggtagtat attggtagat    1860
tattggtata gagatggtat attattaagg aggcagatgg ggtaattaga ggtgagactt    1920
agggacaggg cttgtgatat ggaaaggagt gaagtcactg agtaaaagac aagtttactg    1980
tcagcagaga ttcttagagg ctctttttctc cgtgattaaa aaaaaatcct aaaccagtag    2040
tataataaac ttcctgcctc cagcagtgct gggtagctgg caggatgact gtgcccagtg    2100
atgaggtgac cccagtcaga ccaacttaat gagtatccca ctaattagtt ggatgatgtt    2160
```

```
tgaagctgtc agttaatctc ttagttcaca tcgttcttgt gagcaaagtg aaggaatcgg    2220
ataagctcta aatttcggtg atgctgctgc tctgagagac caaggtcgct ggagcaaccg    2280
tactgctaaa ggataagctc ttcaaaatca aagggacag atttcttaag tttctagttt    2340
gttttgtgtt tttacatcta tttctaccat acgaaagagt aggatggtga gatgcatttc    2400
taaatatttt taactactca gtctggatgg ttaggcttca agaaaggaa tttatttagt    2460 ctgaaataaa gcaattttgc catttaaaat tgaattactt tgtagtttaa tgattactat    2520
tgagcaaaca aatctttaca gtaatataag tcagcaaaag tttttttaaaa ggtttaaatc    2580 cctccttcct tacatctatt tcattgcttt tttaggtttg ggaagtaaag caccagagga    2640
agcatgtgta aatccttgta taatcgcagg ctgtaagtct ttagcatctc aggaagttac    2700
taacttcaaa ctaagtatat aggtagagtt tcttactaaa tctagtgctt cttgaaccac    2760
aagtagaaag catttaaaac atgaatgttg ttttgtgttt tttgaagttt gtaaatagaa    2820
gacttgttga tgatccgatg gcaaggtatt tttctcttgg tatgtatttt agttatttcc    2880
tcgtgatgca taagtgaaaa gagtgaagtt tctcagaatg agcaactgtc atccatctac    2940
ctgctatttt attattgctg attacaaaag caaatcaaga gatgagaacc cagttgcctg    3000
caagtaaata tttactgcat tgagggtcgg agcattttcc cattaccggt tatccatgga    3060
tcaaatagtg tatctcagtg gtaattctag agggccatta aaaccctgat ggtgctggaa    3120
gagatggcag tgctgcatgt cagaaatagg taaactgtaa ttaagaagtt acagatgatt    3180
tgattacgct cttgtgtatt tggtcctgtt ataatgtgag cagattaaaa tcatgtagtg    3240
cttaaagcta tgtcattatg caaacattta tggcaacttc tgcaaattaa tttgaactgt    3300
aaaagttccc taatgagacg atgtcctcca taactgagaa ggacactgca gccattgctg    3360
cttaattcct gcatttgaat ggttgccgag cgcatggtgt gcccttctc aaagagcaga    3420 gaggctgcag agcattttgg ggggtgatga ctgaatgaaa gtgaaagac catttcaaaa    3480 tagcctttaa aaggaaagcc aaggatgatt attaatgaat tcctgggatc taacagtagt    3540
aagaaattta aactatataa acatatatgt taaaggctag ctcttcagaa ataaagatca    3600
gaagactgca                                                          3610
```

<210> SEQ ID NO 44
<211> LENGTH: 568
<212> TYPE: DNA
<213> ORGANISM: Homo sapiens

<400> SEQUENCE: 44

```
gaacccggga ggtggagggt gcagtgagcc aagatcacat cactgcactt cagcctgggc      60
aacaagagta aaactccgtc taaaaaaaaa gaaaaaaaag acattgcca gagtcttggc     120 gatttggccc gacgcgctcc gctttcgcta cagcatggtg gcctactgga gacaggctgg     180
actcagctac atccgatact cccagatctg tgcaaaagta gtgagagatg cactgaagac     240
agaattcaaa gcaaatgcca aaaagacttc tggcaacagc gtaaaaattg tgaaagtaaa     300
gaaggaataa tctaccctga ctaaagcttg aaatgctgca tttccaaggt gaagatgtat     360
gggcacatgt tatggcagat tgaaaggat ctcatttcat gggaaaaaaa aatcctgtct     420
tgttcataaa ttgacaatgt caataaattg aaatatggtt cactgttaaa aaaaaaaaaa     480
aaaaaggttg gaaagtgcaa ggcaaggaaa tggattctct cccagaaacc tccagaagga     540
accagccctg ccaacaccct tgattttag                                       568
```

<210> SEQ ID NO 45
<211> LENGTH: 3013
<212> TYPE: DNA
<213> ORGANISM: Homo sapiens

<400> SEQUENCE: 45

| | | | | | | |
|---|---|---|---|---|---|---|
| cattgccctc | tgccccgcag | cctgcccgtt | cccaggccag | cgagggcgct | cccaggccgg | 60 |
| tctgcagcca | gaacacagcc | cgttccatgt | gcttgtcctc | gggacacatt | aggaatgaac | 120 |
| ccaggcctca | gtcctggcct | cctcctcaag | gctgggtgct | cagacgtccc | cctcagcccc | 180 |
| tttctctaga | ccttccggct | gaacaaacga | gaacatctca | cagccctgca | acagccagga | 240 |
| gctgctcgtg | gagctccacg | cccggctgga | gagagaggag | gcaccctggg | cagcccgcca | 300 |
| gcacccaggc | tctcacagtg | gaagcccacg | tcttcttggg | ctctattttg | aaagctgttc | 360 |
| tttccacgac | ggctttgaca | gaatcgatt | tgagtgagcc | ggcgtgtcaa | tacaggccag | 420 |
| cacaggactg | gcctcagggc | cacattgggg | agggtggcga | ccaggccctg | gctgcagccc | 480 |
| acgtgggcaa | aagcatggcc | aggcaggagg | tgggcctgt | gagcttggct | acagcgaccg | 540 |
| tgggcgctgg | gcccggggct | cctcagcccct | gaggggagac | ccaggccag | gcaggctccc | 600 |
| aggcgggctc | ccgggctccc | agccttccga | tcttctccct | ttgagacctt | gccttctgca | 660 |
| cagtgacagg | aaagagccct | gagtcccact | ttgcagggat | gtattgcatt | tccagaaagt | 720 |
| tccttccggg | tgcagagtga | tacatgaacc | ctggggactc | actccaactt | ggtattgatt | 780 |
| ttctccacgg | aggacccagc | agtcacggcc | cgtgtctgca | cagccccttg | gatcctgcgg | 840 |
| aggaattcag | ccgcccctc | cccctgtgcc | gaaaaccacg | gaggcaaagc | caggccaggg | 900 |
| tacagtgaga | acacgggaga | ggactgagag | accgctggct | gccgagggag | gaagagcagg | 960 |
| attcgcaccc | ccgtcatcgc | tgggcccaca | cgccgccgac | agcttccgcg | tgtggccatc | 1020 |
| tgtcttttcag | aaactctctg | gcagagggac | ccagcagatg | acacgggggc | cgttcacact | 1080 |
| ctgaaacctg | cctggagtca | aaacactgct | ggcgagcctc | caccgcaaac | ccaatccaga | 1140 |
| tggtcttccc | tggtggccct | cggggtggcg | ggcaccctgc | ccactccctg | ccagcccctg | 1200 |
| cccgctggac | tccaggcccg | gtcgagcccc | cgaccggtct | cctgacccag | catgctgctc | 1260 |
| tcccctgggc | ccggcttcct | cgcccgctgg | gactcccagg | cccctccagc | ccagcccga | 1320 |
| gagcaggagc | cccaagggag | gcttggcggc | tgtggaggcg | agtgggccac | gtgtagctgg | 1380 |
| gaggccggca | ggaccaggag | cccctcacag | cgcagcaccc | acagcatcac | gagccacttc | 1440 |
| cactcctggg | tggcctgggg | gccccacccc | tgctctgagc | tgccccttgt | tgtgacctgg | 1500 |
| ggtccccgt | ggtgggcccg | ccccttgagc | ctgggatcca | gcctcagcga | ggctccagaa | 1560 |
| gtgtcgtctc | cgccggccag | gcgtcagcgc | ctccacccag | gatcacacac | tcctatctct | 1620 |
| gcacttctgc | cctccatcct | gctccacgcc | gcctctgctt | gttattccag | cacattccag | 1680 |
| ggtgatgcct | gctgaagcca | cgcagccagt | gcctccaccc | taccccccat | ctgacccacc | 1740 |
| ggccccttcc | gcacgctgga | agcctgcccg | gcctgaagtg | tcctcacctg | tcgccctatc | 1800 |
| ctcccctcca | ctccagccca | ccggtgactc | agccctcaca | gctctctcct | cccgaggga | 1860 |
| gccggtgact | tggctctgat | ggtgccggga | cccagccccg | gcatgttcag | aatccttgtc | 1920 |
| ctttaacctg | cgtccacatg | tagtcgcctc | cacctccctg | cctgaacctc | caggccctgc | 1980 |
| agagcaaaca | ctgctgcctg | caggagaccc | ctggggcctt | ctccgtcccc | tcatcctcct | 2040 |
| aaggagcctc | ccctgccacc | gtgccagaat | gtgccggagg | aacagaggcc | cgagcctccc | 2100 |
| gtggccccag | cgaggcttcc | tctggggaag | acagtgagcc | caacgccctg | gctctcgagg | 2160 |

-continued

```
ggtggacgga gtccagctgg catcaaccgg gtgcccctct tcaccggtgt ccacagtcct    2220
tgagagcaaa gggttcccag aggcgacctc cctcctgcac aggcatttgt catccttacc    2280
ctctaggaca gctttgccat gtgcagtgaa cccctggaca gtgttgcgtg ccactttgcc    2340
ggatttggac tgtatacaga ccgaagcatg tggcatgaag ccttctgctg tcagcaagtt    2400
ccttgtccct cgacagtatg tgcccaggct gcccttcaag gtggcagtga tggcagttgt    2460
ctcttgcacg ctgcgtacag ttctgtcact gactcttaca cacagccctg agacgggag     2520 agtgccggga gcattctatg caagtgtcct ggcctttgcg ggcgtctcca gcacaaac      2580 acgagtcagg gaccacccct cttctgcttc catgattcca ccaactgggt ggggcagagc    2640
agtgccaggg ccggaggcac gccccaggtg agggcaggtg ccatgccag tgagtgcact     2700 gcgttctcag ttaattcatc cgaaatattt ctaagtttct tgattattgc agttgcatcc    2760
ccaagataat gccgccctca ccaagtagaa ggcacatgtg ctctgatggc ccctcccaca    2820
ctggggtcag ggcacagcaa cttagcgagg cgacgtgggg gctcagagga cctcggacca    2880
ggctcggcac atggggcttc tccagccagc caggggaag caccctgcag actgctaact      2940
tttgcaaaat agagtaaaaa agatcagcta gaaaaataaa acaaaaaagg aaagatatac    3000
aaaatacaag gcc                                                       3013
```

<210> SEQ ID NO 46
<211> LENGTH: 3015
<212> TYPE: DNA
<213> ORGANISM: Homo sapiens

<400> SEQUENCE: 46

```
cattgccctc tgccccgcag cctgcccgtt cccaggccag cgagggcgct cccaggccgg      60
tctgcagcca gaacacagcc cgttccatgt gcttgtcctc gggacacatt aggaatgaac     120
ccaggcctca gtcctggcct cctcctcaag gctgggtgct cagacgtccc cctcagcccc    180
tttctctaga ccttccggct gaacaaacga gaacatctca cagccctgca acagccagga    240
gctgctcgtg gagctccacg cccggctgga gagagaggag gcaccctggg cagcccgcca    300
gcacccaggc tctcacagtg gaagcccacg tcttcttggg ctctattttg aaagctgttc    360
tttccacgac ggctttgaca agaatcgatt tgagtgagcc ggcgtgtcaa tacaggccag    420
cacaggactg gcctcagggc cacattgggg agggtggcga ccaggccctg gctgcagccc    480
acgtgggcaa aagcatggcc aggcaggagg tggggcctgt gagcttggct acagcgaccg    540
tgggcgctgg gccggggct cctcagccct gaggggagac ccaggccag gcaggctccc     600 aggcgggctc ccgggctccc agccttccga tcttctccct ttgagacctt gccttctgca    660
cagtgacagg aaagagccct gagtccact ttgcagggat gtattgcatt tccagaaagt     720
tccttccggg tgcagagtga tacatgaacc ctggggactc actccaactt ggtattgatt    780
ttctccacgg aggacccagc agtcacggcc cgtgtctgca cagcccctg gatcctgcgg     840 aggaattcag ccggcccctc ccctgtgcc gaaaaccacg gaggcaaagc caggccaggg     900
tacagtgaga acacgggaga ggactgagag accgctggct gccgagggag gaagagcagg    960
attcgcaccc ccgtcatcgc tgggcccaca cgccgccgac agcttccgcg tgtggccatc    1020
tgtctttcag aaaccctctg gcagagggac ccagcagatg acacgggggc cgttcacact    1080
ctgaaacctg cctggagtca aaacactgct ggcgagcctc caccgcaaac ccaatccaga    1140
tggtcttccc tggtggccct cggggtggcg ggcaccctgc ccactccctg ccagcccctg    1200
```

| | |
|---|---|
| cccgctggac tccaggcccg gccgagcccc cgaccggtct cctgacccag catgctgctc | 1260 |
| tcccctgggc ccggctttct cgcccgctgg gactcccagg cccctccagc ccagccccga | 1320 |
| gagcaggagc cccaagggag gcttggcggc tgtggaggcg agtgggccac gtgtagctgg | 1380 |
| gaggccggca ggaccaggag cccctcacag cgcagcaccc acagcatcac gagccacttc | 1440 |
| cactcctggg tggcctgggg gccccaccc tgctctgagc tgcccctttgt tgtgacctgg | 1500 |
| ggtccccgt ggtgggcccg cccccttgagc ctgggatcca gcctcagcga ggctccagaa | 1560 |
| gtgtcgtctc cgccggccag gcgtcagcgc ctccacccag gatcacacac tcctatctct | 1620 |
| gcacttctgc cctccatcct gctccacgcc gcctctgctt gttattccag cacattccag | 1680 |
| ggtgatgcct gctgaagcca cgcagccagt gcctccaccc tacccccat ctgacccacc | 1740 |
| ggccccttcc gcacgctgga agcctgcccg gcctgaagtg tcctcacctg tcgccctatc | 1800 |
| ctcccctcca ctccagccca ccggtgactc agccctcaca gctctctcct ccccgaggga | 1860 |
| gccggtgact tggctctgat ggtgccggga cccagccccg gcatgttcag aatccttgtc | 1920 |
| ctttaacctg cgtccacatg tagtcgcctc cacctccctg cctgaacctc caggccctgc | 1980 |
| agagcaaaca ctgctgcctg caggagaccc ctggggcctt ctccgtcccc tcatcctcct | 2040 |
| aaggagcctc ccctgccacc gtgccagaat gtgccgagg aacagaggcc cgagcctccc | 2100 |
| gtggccccag cgaggcttcc tctggggaag acagtgagcc caacgccctg gctctcgagg | 2160 |
| ggtggacgga gtccagctgg catcgaccgg gtgccctct tcaccggtgt ccacagtcct | 2220 |
| tgagagcaaa gggttcccag aggcgacctc cctcctgcac aggcatttgt catccttacc | 2280 |
| ctctaggaca gcttttgccat gtgcagtgaa ccctggaca gtgttgcgtg ccactttgcc | 2340 |
| ggatttggac tgtatacaga ccgaagcatg tggcatgaag ccttctgctg tcagcaagtt | 2400 |
| ccttgtccct cgacagtatg tgcccaggct gcccttcaag gtggcagtga tggcagttgt | 2460 |
| ctcttgcacg ctgcgtacag ttctgtcact gactcttaca cacagccctg gagacgggag | 2520 |
| agtgccggga gcattctatg caagtgtcct ggcctttgcg ggcgtctcca cagcacaaac | 2580 |
| acgagtcagg gaccacccct cttctgcttc catgattcca ccaactgggt ggggcagagc | 2640 |
| agtgccaggg ccggaggcac gccccaggtg agggcaggtg gccatgccag tgagtgcact | 2700 |
| gcgttctcag ttaattcatc cgaaatattt ctaagttctt tgattattgc agttgcatcc | 2760 |
| ccaagataat gccgccctca ccaagtagaa ggcacatgtg ctctgatggc ccctcccaca | 2820 |
| ctgggtcag ggcacagcaa cttagcgagg cgacgtgggg gctcagagga cctcggacca | 2880 |
| ggctcggcac atggggcttc tccagccagc caggggaag caccctgcag actgctaact | 2940 |
| tttgcaaaat agagtaaaaa agatcagcta gaaaaataaa acaaaaaagg aaagatatac | 3000 |
| aaaaaaaaaa aaaaa | 3015 |

<210> SEQ ID NO 47
<211> LENGTH: 2079
<212> TYPE: DNA
<213> ORGANISM: Homo sapiens

<400> SEQUENCE: 47

| | |
|---|---|
| actgctgtgc agggcaggaa agctccacac acacagccca gcaaacagca gcacgctgct | 60 |
| gaaaaaaaga ctcagaggag agagataagg aaggaaagta gtgatggatc tcatcccaaa | 120 |
| cttggccgtg gaaacctggc ttctcctggc tgtcagcctg atactcctct atctatatgg | 180 |
| aacccgtaca catggacttt ttaagaagct tggaattcca gggcccacac ctctgccttt | 240 |
| tttgggaaat gctttgtcct tccgtaaggg ctattggacg tttgacatgg aatgttataa | 300 |

| | |
|---|---|
| aaagtataga aaagtctggg gtatttatga ctgtcaacag cctatgctgg ctatcacaga | 360 |
| tcccgacatg atcaaaacag tgctagtgaa agaatgttat tctgtcttca caaaccggag | 420 |
| gcctttcggg ccagtgggat ttatgaaaaa tgccatctct atagctgagg atgaagaatg | 480 |
| gaagagaata cgatcattgc tgtctccaac attcaccagc ggaaaactca aggagatggt | 540 |
| ccctatcatt gcccagtatg gagatgtgtt ggtgagaaat ctgaggcggg aagcagagac | 600 |
| aggcaagcct gtcaccttga aacacgtctt tggggcctac agcatggatg tgatcactag | 660 |
| cacatcattt ggagtgagca tcgactctct caacaatcca caagacccct tgtggaaaa | 720 |
| caccaagaag cttttaagat ttaatccatt agatccattc gttctctcaa taaaagtctt | 780 |
| tccattcctt accccaattc ttgaagcatt aaatatcact gtgtttccaa gaaaagttat | 840 |
| aagttttcta acaaaatctg taaaacagat aaaagaaggt cgcctcaaag agacacaaaa | 900 |
| gcaccgagtg gatttccttc agctgatgat tgactctcag aattcaaaag actctgagac | 960 |
| ccacaaagct ctgtctgatc tggagctcat ggcccaatca attatcttta tttttgctgg | 1020 |
| ctatgaaacc acgagcagtg ttctctcctt cattatatat gaactggcca ctcaccctga | 1080 |
| tgtccagcag aaagtgcaga aggaaattga tacagtttta cccaataagg caccacccac | 1140 |
| ctatgatact gtgctacagt tggagtatct tgacatggtg gtgaatgaaa cactcagatt | 1200 |
| attcccagtt gctatgagac ttgagagggt ctgcaaaaaa gatgttgaaa tcaatgggat | 1260 |
| gtttattccc aaaggggtgg tggtgatgat tccaagctat gttcttcatc atgacccaaa | 1320 |
| gtactggaca gagcctgaga agttcctccc tgaaaggttc agtaaaaaga caaggacaa | 1380 |
| catagatcct tacatataca cacccttggg aagtggaccc agaaactgca ttggcatgag | 1440 |
| gtttgctctc gtgaacatga aacttgctct agtcagagtc cttcagaact tctccttcaa | 1500 |
| accttgtaaa gaaacacaga tccccctgaa attacgcttt ggaggacttc ttctaacaga | 1560 |
| aaaacccatt gttctaaagg ctgagtcaag ggatgagacc gtaagtggag cctgatttcc | 1620 |
| ctaaggactt ctggtttgct cttaagaaa gctgtgcccc agaacaccag agacctcaaa | 1680 |
| ttactttaca aatagaaccc tgaaatgaag acgggcttca tccaatgtgc tgcataaata | 1740 |
| atcagggatt ctgtacgtgc attgtgctct ctcatggtct gtatagagtg ttatacttgg | 1800 |
| taatatagag gagatgacca aatcagtgct ggggaagtag atttggcttc tctgcttctc | 1860 |
| ataggactat ctccaccacc cccagttagc accattaact cctcctgagc tctgataaca | 1920 |
| taattaacat ttctcaataa tttcaaccac aatcattaat aaaaatagga attattttga | 1980 |
| tggctctaac agtgacattt atatcatgtg ttatatctgt agtattctat agtaagcttt | 2040 |
| atattaagca aatcaataaa aacctcttta caaaagtat | 2079 |

<210> SEQ ID NO 48
<211> LENGTH: 6348
<212> TYPE: DNA
<213> ORGANISM: Homo sapiens

<400> SEQUENCE: 48

| | |
|---|---|
| aattaatttt acttaggata agtgttgtta ttattgtttt tattgttgtt ctgttagtta | 60 |
| ctcaaaactt cattctaatt gtgccctgag tttgttaaaa taccatactg tattttgtg | 120 |
| taacatgtaa ataggcatta attttgaga aatagaaatg tttatcctta atgtattttt | 180 |
| aatttgctaa cattgatttt ttattttctt tcctgaaata gcttatttcc taaaatgaaa | 240 |
| gaatttattc tcagatgaat aatttttata tcagctattc ttatcagagc aataaacaaa | 300 |

-continued

```
taccaatgat gcgctcagcc aacaattcat tacactctct gaagagtaac tggacaagga      360
gaaaaacata gggaaaaaac caacagaatt tgttggcatg ttctacacac agaccatggc      420
ttttcagaag ccaagctgaa tcaaaacagt tttaaaagag gcaaccattt gtagaggagt      480
ccttgaagga ttcttcattg ttttcttgga caaaaagaga ccagtggatc caagtgcttc      540
aaatacttct ctcttatttt cttaactcta ttgctctgca atatttactt taccctgtta      600
atgaacagga caaaatggtt aaaaagagaa taagcgtgcg tcaacaaatt caggctcttc      660
tgtacaagaa ttttcttaaa aaatggagaa taaaagagaa gtttattgga atggacaata      720
acattgtttc tagggctata tttgtgcatc ttttcggaac acttcagagc tacccgtttt      780
cctgaacaac ctcctaaagt cctgggaagc gtggatcagt ttaatgactc tggcctggta      840
gtggcatata caccagtcag taacataaca caaaggataa tgaataagat ggccttggct      900
tcctttatga aggaagaac agtcattggg acaccagatg aagagaccat ggatatagaa       960
cttccaaaaa ataccatga aatggtggga gttatattta gtgatacttt ctcatatcgc      1020
ctgaagttta ttggggata tagaatccca gttataaagg agcactctga atacacagaa      1080
cactgttggg ccatgcatgg tgaaattttt tgttacttgg caaagtactg gctaaaaggg      1140
tttgtagctt ttcaagctgc aattaatgct gcaattatag aagtcacaac aaatcattct      1200
gtaatggagg agttgacatc agttattgga ataaatatga agataccacc tttcatttct      1260
aagggagaaa ttatgaatga atggtttcat tttacttgct tagtttcttt ctcttctttt      1320
atatactttg catcattaaa tgttgcaagg gaaagaggaa aatttaagaa actgatgaca      1380
gtgatgggtc tccgagagtc agcattctgg ctctcctggg gattgacata catttgcttc      1440
atcttcatta tgtccatttt tatggctctg gtcataacat caatcccaat tgtatttcat      1500
actggcttca tggtgatatt cacactctat agcttatatg gcctttcttt gatagcattg      1560
gctttcctca tgagtgtttt aataaggaaa cctatgctcg ctggtttggc tggatttctc      1620
ttcactgtat tttggggatg tctgggattc actgtgttat atagacaact tcctttatct      1680
ttgggatggg tattaagtct tcttagccct tttgccttca ctgctggaat ggcccagatt      1740
acacacctgg ataattactt aagtggtgtt atttttcctg atccctctgg ggattcatac      1800
aaaatgatag ccacttttt cattttggca tttgatactc ttttctattt gatattcaca      1860
ttatattttg agcgagtttt acctgataaa gatggccatg gggattctcc attattttc      1920 cttaagtcct cattttggtc caaacatcaa aatactcatc atgaaatctt tgagaatgaa      1980
ataaatcctg agcattcctc tgatgattct tttgaaccgg tgtctccaga attccatgga      2040
aaagaagcca taagaatcag aaatgttata aaagaatata atggaaagac tggaaaagta      2100
gaagcattgc aagcatatt ttttgacata tatgaaggac agatcactgc aatacttggg      2160
cataatggag ctggtaaatc aacactgcta aacattctta gtggattgtc tgtttctaca      2220
gaaggatcag ccactatta taatactcaa ctctctgaaa taactgacat ggaagaaatt      2280
agaaagaata ttggattttg tccacagttc aatttttcaat ttgacttcct cactgtgaga      2340
gaaaacctca gggtatttgc taaaataaaa gggattcagc caaaggaagt ggaacaagag      2400
gtaaaaagaa ttataatgga attagacatg caaagcattc aagacattat tgctaaaaaa      2460
ttaagtggtg ggcagaagag aaaactaaca ctagggattg ccatcttagg agatcctcag      2520
gttttgctgc tagatgaacc aactgctgga ttggatccct tttcaagaca ccgagtgtgg      2580
agcctcctga aggagcataa agtagaccga cttatcctct tcagtaccca attcatggat      2640
gaggctgaca tcttggctga taggaaagta tttctgtcta atgggaagtt gaaatgtgca      2700
```

```
ggatcatctt tgtttctgaa gcgaaagtgg ggtattggat atcatttaag tttacacagg    2760
aatgaaatgt gtgacacaga aaaaatcaca tcccttatta agcagcacat tcctgatgcc    2820
aagttaacaa cagaaagtga agaaaaactt gtatatagtt tgcctttgga aaaaacgaac    2880
aaatttccag atctttacag tgaccttgat aagtgttctg accagggcat aaggaattat    2940
gctgtttcag tgacatctct gaatgaagta ttcttgaacc tagaaggaaa atcagcaatt    3000
gatgaaccag attttgacat tgggaaacaa gagaaaatac atgtgacaag aaatactgga    3060
gatgagtctg aaatggaaca ggttcttttgt tctcttcctg aaacaagaaa ggctgtcagt    3120
agtgcagctc tctggagacg acaaatctat gcagtggcaa cacttcgctt cttaaagtta    3180
aggcgtgaaa ggagagctct tttgtgtttg ttactagtac ttggaattgc ttttatcccc    3240
atcattctag agaagataat gtataaagta actcgtgaaa ctcattgttg ggagttttca    3300
cccagtatgt atttcctttc tctggaacaa atcccgaaga cgcctcttac cagcctgtta    3360
atcgttaata atacaggatc aaatattgaa gacctcgtgc attcactgaa gtgtcaggat    3420
atagttttgg aaatagatga ctttagaaac agaaatggct cagatgatcc ctcctacaat    3480
ggagccatca tagtgtctgg tgaccagaag gattacagat tttctgttgc gtgtaatacc    3540
aagaaattga attgttttcc tgttcttatg ggaattgtta gcaatgccct tatgggaatt    3600
tttaacttca cggagcttat tcaaatgaag agcacttcat tttctcgtga tgacatagtg    3660
ctggatcttg gttttataga tgggtccata tttttgttgt tgatcacaaa ctgcgtttct    3720
ccttttatcg gcatgagcag catcagcgat tataaaaaaa atgttcaatc ccagttatgg    3780
atttcaggcc tctggccttc agcatactgg tgtggacagg ctctggtgga cattccatta    3840
tacttcttga ttctcttttc aatacattta atttactact tcatatttct gggattccag    3900
cttttcatgg gaactcatgtt tgttttggtg gtatgcataa ttggttgtgc agtttctctt    3960
atattcctca catatgtgct ttcattcatc tttcgcaagt ggagaaaaaa taatggcttt    4020
tggtcttttg gctttttttat tatcttaata tgtgtatcca caattatggt atcaactcaa    4080
tatgaaaaac tcaacttaat tttgtgcatg attttcatac cttccttcac tttgctgggg    4140
tatgtcatgt tattgatcca gctcgacttt atgagaaact tggacagtct ggacaataga    4200
ataaatgaag tcaataaaac cattctttta acaaccttaa taccatacct tcagagtgtt    4260
attttccttt ttgtcataag gtgtctgaa atgaagtatg gaaatgaaat aatgaataaa    4320
gacccagttt tcagaatctc tccacggagt agagaaactc atcccaatcc ggaagagccc    4380
gaagaagaag atgaagatgt tcaagctgaa agagtccaag cagcaaatgc actcactgct    4440
ccaaacttgg aggaggaacc agtcataact gcaagctgtt tacacaagga atattatgag    4500
acaagaaaaa gttgcttttc aacaagaaag aagaaaatag ccatcagaaa tgtttccttt    4560
tgtgttaaaa aaggtgaagt tttgggatta ctaggacaca atggagctgg taaaagtact    4620
tccattaaaa tgataactgg ggtgcacaaag ccaactgcag gagtggtggt gttacaaggc    4680
agcagagcat cagtaaggca acagcatgac aacagcctca agttcttggg gtactgccct    4740
caggagaact cactgtggcc caagcttaca atgaaagagc acttggagtt gtatgcagct    4800
gtgaaaggac tgggcaaaga agatgctgct ctcagtattt cacgattggt ggaagctctt    4860
aagctccagg aacaacttaa ggctcctgtg aaaactctat cagagggaat aaagagaaag    4920
ctgtgctttg tgctgagcat cctggggaac ccatcagtgg tgcttctaga tgagccgttc    4980
accgggatgg accccgaggg gcagcagcaa atgtggcaga tacttcaggc taccgttaaa    5040
```

```
aacaaggaga gggcacccct cttgaccacc cattacatgt cagaggctga ggctgtgtgt      5100
gaccgtatgg ccatgatggt gtcaggaacg ctaaggtgta ttggttccat tcaacatctg      5160
aaaaacaagt ttggtagaga ttatttacta gaaataaaaa tgaaagaacc tacccaggtg      5220
gaagctctcc acacagagat tttgaagctt ttcccacagg ctgcttggca ggaaagatat      5280
tcctctttaa tggcgtataa gttacctgtg gaggatgtcc accctctatc tcgggccttt      5340
ttcaagttag aggcgatgaa acagaccttc aacctggagg aatacagcct ctctcaggct      5400
accttggagc aggtattctt agaactctgt aaagagcagg agctgggaaa tgttgatgat      5460
aaaattgata caacgttga atggaaactt ctcccacagg aagacccctta aaatgaagaa      5520 cctcctaaca ttcaatttta ggtcctacta cattgttagt ttccataatt ctacaagaat      5580
gtttcctttt acttcagtta acaaaagaaa acatttaata aacattcaat aatgattaca      5640
gttttcattt ttaaaaattt aggatgaagg aaacaaggaa atatagggaa aagtagtaga      5700
caaaattaac aaaatcagac atgttattca tccccaacat gggtctattt tgtgcttaaa      5760
aataatttaa aaatcataca atattaggtt ggttatcggt tattatcaat aaagctaaca      5820
ctgagaacat tttacaaata aaaatatgag gttttttagcc tgaacttcaa atgtatcagc      5880
tatttttaaa cattatttac tcggattcta atttaatgtg acattgacta taagaaggtc      5940
tgataaactg atgaaatggc acagcataac atttaattat aatgacattc tgattataaa      6000
ataaatgcat gtgaattta gtacatattg aagttatatg gaagaagata gccataatct      6060
gtaagaaagt accgcagtta atattttctt tagccaactt atattcaatg tatttttat       6120 ggatcctttt tcaaaggtag tatcagtagg catagtcatt ttctgtatct tttcacctca      6180
cagttcatga acatttccca tgtcattata gcacttttgt gttatataat tgctgcatta      6240
atgttatagc tgtattgatg taataccaga gttgttacgt tcgggttata tgcaagttta      6300
tttcttagaa ataaaacttt gatggacttt taaaaaaaaa aaaaaaa                    6348

<210> SEQ ID NO 49
<211> LENGTH: 1892
<212> TYPE: DNA
<213> ORGANISM: Homo sapiens

<400> SEQUENCE: 49
aaaccggtgc caacgtgcgc ggacgccgcc gccgccgccg ccgctggagt ccgccgggca        60
gagccggccg cggagcccgg agcaggcgga gggaagtgcc cctagaacca gctcagccag       120
cggcgcttgc acagagcggc cggacgaaga gcagcgagag gaggagggga gagcggctcg       180
tccacgcgcc ctgcgccgcc gccggcccgg gaaggcagcg aggagccggc gcctcccgcg       240
ccccgcggtc gccctggagt aatttcggat gcccagccgc ggccgccttc cccagtagac       300
ccgggagagg agttgcggcc aacttgtgtg cctttcttcc gccccggtgg gagccggcgc       360
tgcgcgaagg gctctcccgg cggctcatgc tgccggccct cgcctgcc agcctcgggt        420 gagccgcctc cggagagacg ggggagcgcg gcggcgccgc gggctcggcg tgctctcctc       480
cggggacgcg ggacgaagca gcagccccgg gcgcgcgcca gaggcatgga gcgctgcccc       540
agcctagggg tcaccctcta cgccctggtg gtggtcctgg ggctgcgggc gacaccggcc       600
ggcggccagc actatctcca catccgcccg gcacccagcg acaacctgcc cctggtggac       660
ctcatcgaac acccagaccc tatctttgac cccaaggaaa aggatctgaa cgagacgctg       720
ctgcgctcgc tgctcgggg ccactacgac ccaggcttca tggccacctc gccccccgag       780
gaccggcccg gcggggcgg gggtgcagct gggggcgcgg aggacctggc ggagctggac       840
```

```
cagctgctgc ggcagcggcc gtcgggggcc atgccgagcg agatcaaagg gctagagttc      900
tccgagggct tggcccaggg caagaagcag cgcctaagca agaagctgcg gaggaagtta      960
cagatgtggc tgtggtcgca gacattctgc cccgtgctgt acgcgtggaa cgacctgggc     1020
agccgctttt ggccgcgcta cgtgaaggtg ggcagctgct tcagtaagcg ctcgtgctcc     1080
gtgcccgagg gcatggtgtg caagccgtcc aagtccgtgc acctcacggt gctgcggtgg     1140
cgctgtcagc ggcgcggggg ccagcgctgc ggctggattc ccatccagta ccccatcatt     1200
tccgagtgca agtgctcgtg ctagaactcg ggggccccct gcccgcaccc ggacacttga     1260
tcgatcccca ccgacgcccc ctgcaccgcc tccaaccagt tccaccaccc tctagcgagg     1320
gttttcaatg aactttttt tttttttttt ttttttttc tgggctacag agacctagct     1380
ttctggttcc tgtaatgcac tgtttaactg tgtaggaatg tatatgtgtg tgtatatacg     1440
gtcccagttt taatttactt attaaaaggt cagtattata cgttaaaagt taccggcttc     1500
tactgtattt ttaaaaaaaa gtaagcaaaa gaaaaaaaaa agaacagaga aaagagagac     1560
ttattctggt tgttgctaat aatgttaacc tgctatttat attccagtgc ccttcgcatg     1620
gcgaagcagg ggggaaaagt tattttttc ttgaagtaca aagagacggg ggaacttttg     1680
tagaggactt tttaaaagct attttccatt cttcggaaag tgttttggtt ttccttggac     1740
ctcgaagaag ctatagagtt caatgttatt ttacagttat tgtaaatata gagaacaaat     1800
ggaatgacta atcattgtaa attaagagta tctgctattt attctttata atatcccgtg     1860
tagtaaatga gaaagaagtg cagagcagga tt                                  1892
```

<210> SEQ ID NO 50
<211> LENGTH: 3227
<212> TYPE: DNA
<213> ORGANISM: Homo sapiens

<400> SEQUENCE: 50

```
cccactctgc agttgtctcc cgagcgctgg ctgcgccgcc cgagccgctg ggccggggaa       60
gcactggccg ttcgctcccg ggccggctcc gccaggcgct cgcaggcatg cagcccggga      120
gcaggaggcg ctccccgggc cgctgctgag ccggccgggg cggcggggac cagcgccagc      180
ggagcccctc ccaccttgcc ccggggcaga cgagcggcgc cccgacaccc cctcttctcc      240
cgcagccccg ccagcgccac cccccgcggg ccgcaggggc tcatgcagcc gccaagggag      300
aggctagtgg taacaggccg agctggatgg atgggtatgg ggagaggggc aggacgttca      360
gccctgggat tctggccgac cctcgccttc cttctctgca gcttcccgc agccacctcc      420 ccgtgcaaga tcctcaagtg caactctgag ttctggagcg ccacgtcggg cagccacgcc      480
ccagcctcag acgacacccc cgagttctgt gcagccttgc gcagctacgc cctgtgcacg      540
cggcggacgg cccgcacctg ccggggtgac ctggcctacc actcggccgt ccatggcata      600
gaggacctca tgagccagca caactgctcc aaggatggcc ccacctcgca gccacgcctg      660
cgcacgctcc caccggccgg agacagccag gagcgctcgg acagcccga tctgccat      720 tacgagaaga gctttcacaa gcactcggcc accccaact acacgcactg tggcctcttc      780
ggggacccac acctcaggac tttcaccgac cgcttccaga cctgcaaggt gcagggcgcc      840
tggccgctca tcgacaataa ttacctgaac gtgcaggtca ccaacacgcc tgtgctgccc      900
ggctcagcgg ccactgccac cagcaagctc accatcatct tcaagaactt ccaggagtgt      960
gtggaccaga aggtgtacca ggctgagatg gacgagctcc cggccgcctt cgtggatggc     1020
```

```
tctaagaacg gtggggacaa gcacggggcc aacagcctga agatcactga gaaggtgtca    1080
ggccagcacg tggagatcca ggccaagtac atcggcacca ccatcgtggt gcgccaggtg    1140
ggccgctacc tgacctttgc cgtccgcatg ccagaggaag tggtcaatgc tgtggaggac    1200
tgggacagcc agggtctcta cctctgcctg cggggctgcc ccctcaacca gcagatcgac    1260
ttccaggcct ccacaccaa tgctgagggc accggtgccc gcaggctggc agccgccagc    1320
cctgcaccca cagcccccga gaccttccca tacgagacag ccgtggccaa gtgcaaggag    1380
aagctgccgg tggaggacct gtactaccag gcctgcgtct tcgacctcct caccacgggc    1440
gacgtgaact tcacactggc cgcctactac gcgttggagg atgtcaagat gctccactcc    1500
aacaaagaca aactgcacct gtatgagagg actcgggacc tgccaggcag ggcggctgcg    1560
gggctgcccc tggcccccg gcccctcctg ggcgccctcg tcccgctcct ggccctgctc    1620
cctgtgttct gctagacgcg tagatgtgga gggaggcgcg ggctccgtcc tctcggcttc    1680
cccatgtgtg ggctgggacc gcccacgggg tgcagatctc ctggcgtgtc caccatggcc    1740
ccgcagaacg ccagggaccg cctgctgcca agggctcagg cacggacccc tccccttcta    1800
gtgcacgtga caaggttgtg gtgactggtg ccatgatgtt tgacagtaga gctgtgtgag    1860
agggagagca gctcccctcg ccccgcccct gcagtgtgaa tgtgtgaaac atcccctcag    1920
gctgaagccc ccaccccca ccagagacac actgggaacc gtcagagtca gctccttccc    1980
cctcgcaatg cactgaaagg cccggccgac tgctgctcgc cgatccgtgg ggcccctgt    2040 gcccgccaca cgcacgcaca cactcttaca cgagagcaca ctcgatcccc ctaggccagc    2100
ggggacaccc cagccacaca gggaggcatc cttggggctt ggccccaggc agggcaaccc    2160
cggggcgctg cttggcacct tagcagactg ctggaacctt ttggccagta ggtcgtgccc    2220
gcctggtgcc ttctggcctg tggcctccct gcccatgttc acctggctgc tgtgggtacc    2280
agtgcaggtc ccggttttca ggcacctgct cagctgcccg tctctggcct gggcccctgc    2340
cccttccacc ctgtgcttag aaagtcgaag tgcttggttc taaatgtcta aacagagaag    2400
agatccttga cttctgttcc tctctctcct gcagatgcaa gagctcctgg gcaggggtgc    2460
ctgggcccca gggtgtggca ggagaccag tggatggggc cagctggcct gccctgatcc    2520
tctgcttcct cctcacaacc ccaagagccc ccagcccggt ccatccacgt ctggagtctg    2580
gggagaggag cagggtctta ggactctcag ctctgagcat ccctggcagg gtcttcaacc    2640
tctaatctct tcccttaagc cctgtggcca cacagccagg agagacttgc cgctggctcc    2700
cgcctcattt cagcccaggg tgctcatcca ggggcccaga acagtcccac ctgtgctgct    2760
gtgcccacag cacaaagcca ggcttcactc ccaaaagtgc agccaggccc tggagggtga    2820
tcctgccagc agcccctacag ctccacaccc tacccaccca tcggcagccc ctctgctgtt    2880
ccccagggac ctctcataca ctggccagga ggctgcagaa cgtgtgtctc cccctccctc    2940
caagaggtcc tgctccctct gccagaaccg tgtgtgggcg ggtgggaggg cgctcggggc    3000
ccggcccctc cctctccctg ctggttttag ttggtcccta tgttggaagt aaaaagtgaa    3060
gcactttatt ttggttgtgt ttgctcacgt tctgcttgga agtggggacc cctcactgcg    3120
tccacgtgtc tgcgacctgt gtggagtgtc accgcgtgta catactgtaa attatttatt    3180
aatggctaaa tgcaagtaaa gtttggtttt tttgttattt tcttttta                 3227
```

<210> SEQ ID NO 51
<211> LENGTH: 3200
<212> TYPE: DNA
<213> ORGANISM: Homo sapiens

```
<400> SEQUENCE: 51
ccatactgaa gccctcccaa gtgcagcctt gcgggcctcg cagagagcgc caaaccatcc      60
ggccctgcgc gccacgcgga ccggcatagc catctctctg gagtggcagc tgtgccaagg     120
tggcaaggtt aggcccgcag gccctcagca cgggggcgca gccggggcaa gtcttcagga    180
agcagcgagg tgcttgaagg gggtgctgga ggcaggccaa acccagtcag gatgggtggc    240
ctggggccac gacgggcggg aacctcgagg gagaggctag tggtaacagg ccagctgga     300
tggatgggta tggggagagg ggcaggacgt tcagccctgg gattctggcc gaccctcgcc    360
ttccttctct gcagcttccc cgcagccacc tccccgtgca agatcctcaa gtgcaactct    420
gagttctgga gcgccacgtc gggcagccac gccccagcct cagacgacac ccccgagttc    480
tgtgcagcct tgcgcagcta cgccctgtgc acgcggcgga cggcccgcac ctgccggggt    540
gacctggcct accactcggc cgtccatggc atagaggacc tcatgagcca gcacaactgc    600
tccaaggatg gccccacctc gcagccacgc ctgcgcacgc tcccaccggc cggagacagc    660
caggagcgct cggacagccc cgagatctgc cattacgaga agagctttca caagcactcg    720
gccaccccca actacacgca ctgtggcctc ttcggggacc cacacctcag gactttcacc    780
gaccgcttcc agacctgcaa ggtgcagggc gcctggccgc tcatcgacaa taattacctg    840
aacgtgcagg tcaccaacac gcctgtgctg cccggctcag cggccactgc caccagcaag    900
ctcaccatca tcttcaagaa cttccaggag tgtgtggacc agaaggtgta ccaggctgag    960
atggacgagc tcccggccgc cttcgtggat ggctctaaga acggtgggga caagcacggg   1020
gccaacagcc tgaagatcac tgagaaggtg tcaggccagc acgtggagat ccaggccaag   1080
tacatcggca ccaccatcgt ggtgcgccag gtgggccgct acctgacctt gccgtccgc    1140
atgccagagg aagtggtcaa tgctgtggag gactgggaca gccagggtct ctacctctgc   1200
ctgcggggct gcccccctcaa ccagcagatc gacttccagg ccttccacac caatgctgag   1260
ggcaccggtg cccgcaggct ggcagccgcc agccctgcac ccacagcccc cgagaccttc   1320
ccatacgaga cagccgtggc caagtgcaag gagaagctgc cggtggagga cctgtactac   1380
caggcctgcg tcttcgacct cctcaccacg ggcgacgtga acttcacact ggccgcctac   1440
tacgcgttgg aggatgtcaa gatgctccac tccaacaaag acaaactgca cctgtatgag   1500
aggactcggg acctgccagg cagggcggct gcggggctgc ccctggcccc ccggccccctc   1560
ctgggcgccc tcgtcccgct cctggccctg ctccctgtgt tctgctagac gcgtagatgt   1620
ggagggaggc gcgggctccg tcctctcggc ttccccatgt gtgggctggg accgccacg    1680
gggtgcagat ctcctggcgt gtccaccatg gccccgcaga acgcagggca ccgcctgctg   1740
ccaagggctc aggcacggac ccctcccctt ctagtgcacg tgacaaggtt gtggtgactg   1800
gtgccatgat gtttgacagt agagctgtgt gagagggaga gcagctcccc tcgccccgcc   1860
cctgcagtgt gaatgtgtga acatcccct caggctgaag ccccccaccc ccaccagaga    1920
cacactggga accgtcagag tcagctcctt cccctcgca atgcactgaa aggcccggcc    1980
gactgctgct cgccgatccg tggggccccc tgtgcccgcc acgcacgc acacactctt     2040
acacgagagc acactcgatc cccctaggcc agcggggaca ccccagccac acaggaggc     2100
atccttgggg cttggcccca ggcagggcaa ccccggggcg ctgcttggca ccttagcaga   2160
ctgctggaac cttttggcca gtaggtcgtg cccgcctggt gccttctggc ctgtggcctc   2220
cctgcccatg ttcacctggc tgctgtgggt accagtgcag gtcccggttt tcaggcacct   2280
```

| | | |
|---|---|---|
| gctcagctgc cgtctctgg cctgggcccc tgcccttcc accctgtgct tagaaagtcg | 2340 | |
| aagtgcttgg ttctaaatgt ctaaacagag aagagatcct tgacttctgt tcctctctct | 2400 | |
| cctgcagatg caagagctcc tgggcagggg tgcctgggcc ccagggtgtg gcaggagacc | 2460 | |
| cagtggatgg ggccagctgg cctgccctga tcctctgctt cctcctcaca accccaagag | 2520 | |
| cccccagccc ggtccatcca cgtctggagt ctggggagag gagcagggtc ttaggactct | 2580 | |
| cagctctgag catccctggc agggtcttca acctctaatc tcttccctta agccctgtgg | 2640 | |
| ccacacagcc aggagagact tgccgctggc tcccgcctca tttcagccca gggtgctcat | 2700 | |
| ccaggggccc agaacagtcc cacctgtgct gctgtgccca cagcacaaag ccaggcttca | 2760 | |
| ctcccaaaag tgcagccagg ccctggaggg tgatcctgcc agcagcccta cagctccaca | 2820 | |
| ccctacccac ccatcggcag cccctctgct gttccccagg acctctcat acactggcca | 2880 | |
| ggaggctgca gaacgtgtgt ctccccctcc ctccaagagg tcctgctccc tctgccagaa | 2940 | |
| ccgtgtgtgg gcgggtggga gggcgctcgg ggcccggccc ctccctctcc ctgctggttt | 3000 | |
| tagttggtcc ctatgttgga agtaaaaagt gaagcacttt attttggttg tgtttgctca | 3060 | |
| cgttctgctt ggaagtgggg acccctcact gcgtccacgt gtctgcgacc tgtgtggagt | 3120 | |
| gtcaccgcgt gtacatactg taaattattt attaatggct aaatgcaagt aaagtttggt | 3180 | |
| tttttgtta tttctttta | 3200 | |

<210> SEQ ID NO 52
<211> LENGTH: 590
<212> TYPE: DNA
<213> ORGANISM: Homo sapiens

<400> SEQUENCE: 52

| | | |
|---|---|---|
| atcccactgg gaagcttcaa catagctgtg gaagtctgca gtctacagga gcctactata | 60 | |
| gacattctac aaccaaccag aatcatggaa cagccaactt ccagcaccaa tggggagaag | 120 | |
| acgaagagcc cctgtgaatc caataacaaa aaaaatgatg agatgcaaga ggtaccaaac | 180 | |
| agagtcttag cccccgaaca gagtttgaag aacacaaaaa catcagaata tccaataata | 240 | |
| tttgtgtatt acctcaggaa gggtaagaaa ataaattcaa atcaactgga gaatgaacag | 300 | |
| tcccaagaga actccatcaa tccaatccaa aaggaggagg acgaaggcgt agacttatct | 360 | |
| gaaggatctt caaatgagga tgaagaccta ggcccatgtg aaggaccttc aaaggaggac | 420 | |
| aaagatctag actcatctga aggatcctca caggaggatg aagacctagg cttatctgaa | 480 | |
| ggatcttcac aggacagtgg ggaggattag tcacacatgg agaaaccaaa ttggacaaat | 540 | |
| catcaccact gatggcgatg attacaataa aatcaagttt aaggagctga | 590 | |

<210> SEQ ID NO 53
<211> LENGTH: 1408
<212> TYPE: DNA
<213> ORGANISM: Homo sapiens

<400> SEQUENCE: 53

| | | |
|---|---|---|
| caccttcctc ccatcttgcc ttctccctcg agttgggacc cgggaagaac catgaagtgg | 60 | |
| ctgctgctgc tgggtctggt ggcgctctct gagtgcatca tgtacaaggt ccccctcatc | 120 | |
| agaaagaagt ccttgaggcg caccctgtcc gagcgtggcc tgctgaagga cttcctgaag | 180 | |
| aagcacaacc tcaacccagc cagaaagtac ttccccagt gggaggctcc caccctggta | 240 | |
| gatgaacagc ccctgagaa ctacctggat atggagtact cggcactat ggcatcgga | 300 | |
| actcctgccc aggatttcac cgtcgtcttt gacaccggct cctccaacct gtgggtgccc | 360 | |

-continued

| | |
|---|---|
| tcagtctact gctccagtct tgcctgcacc aaccacaacc gcttcaaccc tgaggattct | 420 |
| tccacctacc agtccaccag cgagacagtc tccatcacct acggcaccgg cagcatgaca | 480 |
| ggcatcctcg gatacgacac tgtccaggtt ggaggcatct ctgacaccaa tcagatcttc | 540 |
| ggcctgagcg agacggaacc tggctccttc ctgtattatg ctcccttcga tggcatcctg | 600 |
| gggctggcct accccagcat ttcctcctcc ggggccacac cgtctttga caacatctgg | 660 |
| aaccagggcc tggtttctca ggacctcttc tctgtctacc tcagcgccga tgacaagagt | 720 |
| ggcagcgtgg tgatctttgg tggcattgac tcttcttact acactggaag tctgaactgg | 780 |
| gtgcctgtta ccgtcgaggg ttactggcag atcaccgtgg acagcatcac catgaacgga | 840 |
| gagaccatcg cctgtgctga gggctgccag gccattgttg acaccggcac ctctctgctg | 900 |
| accggcccaa ccagccccat tgccaacatc cagagcgaca tcggagccag cgagaactca | 960 |
| gatggcgaca tggtggtcag ctgctcagcc atcagcagcc tgcccgacat cgtcttcacc | 1020 |
| atcaatggag tccagtaccc cgtgccaccc agtgcctaca tcctgcagag cgaggggagc | 1080 |
| tgcatcagtg gcttccaggg catgaacgtc cccaccgaat ctggagagct ttggatcctg | 1140 |
| ggtgatgtct tcatccgcca gtactttacc gtcttgaca gggcaaacaa ccaggtcggc | 1200 |
| ctggcccctg tggcttaagc ctaagtctct tcagccacct cccaggaaga tctggcctcc | 1260 |
| gtcctatgcc cactttagat gtatctaatt ctcctgactg ttcttcccag gggagtgtga | 1320 |
| aggtcttggc cctgttccct gtcctaccaa taacgtagaa taaaaacata acccactgaa | 1380 |
| aaaaaaaaaa aaaaaaaaaa aaaaaaaa | 1408 |

<210> SEQ ID NO 54
<211> LENGTH: 5073
<212> TYPE: DNA
<213> ORGANISM: Homo sapiens

<400> SEQUENCE: 54

| | |
|---|---|
| aggctggccc tggctgcctg cggcgcgggc gcctccctcg cagccgctgc tgccgacgcc | 60 |
| gctgcgctcc cgcctcctgt cggttcccgg gttcccgctg cggctgcggt tctggcagcc | 120 |
| gagcccccgc ggtgctgcag cccagcttta gcgcgcagac cgaccgcgc ccttcttcg | 180 |
| ccgccggcag cctctaatcc acgcggcgcg ttgcggcagg tgcctgggc gtactgaggc | 240 |
| gcggtggcct gagcccggcc gccatcgatg acccccgtcg cggacttgct tcaggctggc | 300 |
| caccccccgt cttgtttcat catctgtgtt gagtaaccat ggggaggaag ctggacctgt | 360 |
| ctggtttgac tgatgatgaa acagagcatg ttcttcaggt ggttcaaaga gacttcaatc | 420 |
| ttcgcaaaaa agaagaagaa cgactaagtg agctgaagca aagctggat gaggaaggca | 480 |
| gcaagtgcag catcctctcg aagcaccagc agtttgtgga gcactgctgc atgcgctgct | 540 |
| gctcgcccctt caccttcctc gtcaacacca gcgccagtg tggagattgc aaattcaatg | 600 |
| tctgcaagag ctgctgctcc taccagaagc acgaaaaggc ctgggtctgc tgcgtctgcc | 660 |
| agcaagcgag gcttctgagg gcccaatctc tggaatggtt ctacaataat gtgaagagcc | 720 |
| gcttcaagcg ctttggcagt gccaaggttc tgaagaacct gtacaggaag caccggctgg | 780 |
| agagtggcgc gtgcttcgac attctaggag gaagccttt tgagtcaaac ctggagaatg | 840 |
| aaggaagcat ttctggcagt gattcaacat tttataggca gtcagaagga catagtgtga | 900 |
| tggacaccctt ggctgtggcc ctacgggtgg ctgaagaggc cattgaggaa gcaatttcca | 960 |
| aagcagaggc atatggggac agcctggaca agcaaaatga ggccagttac ctgcgggacc | 1020 |

```
acaaggagga gctaactgag gaactggcca cgacaatcct gcagaagatt atacgaaaac    1080
agaagagcaa aagtgagcag caagtggaag aagagccagg atggccacat ccccagagtt    1140
gcagcacaaa ggtggcagat gaggggacct cagcatcccc tggaggctac cgtgctcccg    1200
ctgccctctg gaggtccag tctgccttct caatcactgg agaagaagcc ctgaagaccc     1260
ctccagtgga ggctccatcg aggcagccaa gggaccaagg ccaacacccg agagcagagt    1320
ctgctctgcc cagctggaag agtgtggaca ggctggatga acaaacctg gccccagttt     1380
tgcagagccc cgacgggaac tgggtggccc tgaaggatgg cgctccaccc ccacccgac    1440
tactggccaa acctaagagc gggacgtttc aggccctgga ggtggcctcc agtgtggcat    1500
ctgcctacga tgagatgggc tccgatagcg aggaagactt tgactggagt gaggccttga    1560
gcaagctgtg tccaggtcc cgggccctgc ccaggaaccc ccagcctcag cccacacagg     1620
cccagagctc tgaccaaggc cccatagctg cctccccatc ctctgcactc tcccccaacc    1680
ctgaggccat gtgctctgac tcggagacct cctccgcagg ctcttcccga gaagttgggc    1740
accaggccag actgtcctgg ttgcagagga aggcccccag gaaccctgca gctgagaaga    1800
tgcgcttgca tggagagctg gacgtgaact tcaaccccca gttggccagc agggagacct    1860
cggacagcag cgagccggag gaggccccc acaccacaga ccggcgggcc aggaggtgga    1920
gaagagcccg actgggctca gaagagccaa gcaaagaacc atcttccccc agcgcccagc    1980
tccgggatct agacacacat caggtgtcgg atgatttatc agagacagac atcagcaatg    2040
aggctcggga tccccagact ctcacagaca ccacagagga gaaacggaga acaggctgt    2100
acgagttagc aatgaaaatg agtgaaaagg agacttcttc aggggaggat caggagtctg    2160
agcccaagac agaatctgag aaccagaagg aaagtctgtc ctctgaagac aacagccaga    2220
gtgtccagga gagctgaag aagaagtttt ctgctgtttc tctctgcaac atctccacag     2280
aagtcctgaa agtcatcaat gccacagagg agttgatagc aggatctaca gggccctggg    2340
agtccccaca agtccctcct gacagacaga aggggatgtt tcctcgtggg acagaccaag    2400
tgagactgga tgagcagctg acttccctgg aagaaaatgt ataccctggca gcaggcactg    2460
tgtatggact ggagacccag ctgactgagc tagaagatgc cgcccgctgc atccacagtg    2520
gcactgatga gacccatctg gcggatctgg aggaccaggt ggccacggct gcagcccaag    2580
tccaccatgc tgaactccag atttcagata ttgagagccg gatttcagcc ctgaccattg    2640
caggattaaa catagcacca tgtgtgcgct tcacaagaag acgggatcag aagcaaagga    2700
cccaggtaca aaccatagat acatcaaggc agcaaaggag gaaactgcct gctccaccgg    2760
tgaaagctga aaaaattgag acatcttcag tgactaccat taaaacatttt aaccacaact    2820
tcattctcca aggctcctca acaaacagga ctaaggaaag gaaaggcacc accaaggatt    2880
tgatggagcc tgctctggag tcagctgtga tgtactgaca ccatggaatt ccactgccag    2940
tgacccactg cctccggccg tacacgacag tgccttgacc caacagccat cgagtactgt    3000
atgtatttcc acctgaggag aaggcctggg gaggccacag tgcaccattg cacagggctg    3060
tcctgatacc tcatccagaa agccgtctca gacttcagca ctgcggtctt gcccactctc    3120
tgccttaggc tccagggga atccaagaca gaaaatgaag acactggctt caacagcag    3180
cgctccatgt ttaagataca tattttccct gtttgctttg ctactgtatg ttgactttaa    3240
gatcttttt taaatacatt tgattcagct agtattccat gtcaacaatt tgtccaaagg    3300
aaaactgctg gagggaggtg gagggaggaa ggtgggaatt attatttaat acatcattaa    3360
tgcttattaa tctctcacaa gcatctttgt cttgcaaatc ctaagggaaa agcaagtccc    3420
```

| | |
|---|---:|
| tgcagtgagc actagggaca gtctaatttg gggattgctc aaccatcaag actgcaggtc | 3480 |
| tcccttcagc cacctccttc ctgctaaaag cttagcctac cacactacca gtcattccca | 3540 |
| tcgctttgca atcacaagcc acaggatgag aagttctgac tcactcatgc catgcccagg | 3600 |
| gctatctgaa acaatgtctc attaagaatt tagggttctt ccatgggctt actgacagtt | 3660 |
| gcccagatct gaaggggaaa gggtcttgag aaagaccatc actggctcaa ctttagggca | 3720 |
| ctgtccagag tcaacatgat gtggtttagc agtgatcaca tctaaacaaa gtttaggtaa | 3780 |
| atgaattatc gcagagaaaa accacatgag aaaattttg tactccaaat ttacttccca | 3840 |
| ataaatattc agcaaagtag taaaatgacc ttaaagataa aaatgattag ggaatagcct | 3900 |
| tagaaaattt ataggtataa aaaattcaag acaaactgt gcatttaatg gacacaagaa | 3960 |
| ttgactctaa ctccatgtct gtggtttctt tgaacccata tcaaatgtat gactatttag | 4020 |
| agtgtttata agagataatg gaactgaact ttcactcaat taattgggca ttaacaacct | 4080 |
| tcttttatgt ttgttcctga tatagtctga atcttaggaa gaaggtaaaa gaaaggaggc | 4140 |
| aagagaatag ttatgatgaa tatgtgttaa gtgcctgctc tgaaggaggc aatgttcttc | 4200 |
| tcatttgaat ccttatggca accttattca ataggttttc ccatatttca gatttaataa | 4260 |
| ctgaaggcca gagagattaa tttgccaaag ccacacccttt atgctaatta tgattggaat | 4320 |
| gcatcacaaa agcctaactc tgttgttttc aacctctacg ttattttgct gctatgtgca | 4380 |
| tttccagatc tgattttctg ctaacttgtg tgctatgatc cactcctgat ggggtctac | 4440 |
| attaatcttc cagtactcct tgctgatgct gtgttatgtg tcatctaaca gaaatgactc | 4500 |
| ctttgaaata agtaaatctt tggcttttg ttctgttggt gtgattcaaa gcaaacaaa | 4560 |
| caaacaaaaa caaattttaa gaacacaaca aaaagattt gacttccgaa tagaatgttt | 4620 |
| tctttaagag gcatgaaaag caactattgt tgtgttacag tgttaaaaat attcagtttt | 4680 |
| ctttgacaaa aatgtgtact gtgtaagcct tgcaaacaaa aaacaacaaa aaagaagcag | 4740 |
| cagcagcagc ctgctgtgtg gcatctgaac ttttataaag gtttccttgt gccaaataag | 4800 |
| tgcaaagatt taatttacta ttaaaaacca taagcatatg ttatagttcc agaagaatta | 4860 |
| ttttgtcatc aagtgatttt gatctttagt gtcaatattt atatttagat taattttat | 4920 |
| aaatgaaaat attttaatgg tttaagaaaa tgaggacaac aggataatat ctttgatgac | 4980 |
| ttctgaaagt tatgcttccc ttcatgttat atgcacattg ccaagaatta ctgtcaagag | 5040 |
| aaatgataag taaaagtcat ttatgaaaat aaa | 5073 |

<210> SEQ ID NO 55
<211> LENGTH: 4857
<212> TYPE: DNA
<213> ORGANISM: Homo sapiens

<400> SEQUENCE: 55

| | |
|---|---:|
| aacccggcgg ttccgcagct gtgtttggga gacttggggg cgcattagcc tggacagctc | 60 |
| cctgatcggt cttgtttcat catctgtgtt gagtaaccat ggggaggaag ctggacctgt | 120 |
| ctggtttgac tgatgatgaa acagagcatg ttcttcaggt ggttcaaaga gacttcaatc | 180 |
| ttcgcaaaaa agaagaagaa cgactaagtg agctgaagca gaagctggat gaggaaggca | 240 |
| gcaagtgcag catcctctcg aagcaccagc agtttgtgga gcactgctgc atgcgctgct | 300 |
| gctcgccctt caccttcctc gtcaacacca agcgccagtg tggagattgc aaattcaatg | 360 |
| tctgcaagag ctgctgctcc taccagaagc acgaaaaggc ctgggtctgc tgcgtctgcc | 420 |

-continued

```
agcaagcgag gcttctgagg gcccaatctc tggaatggtt ctacaataat gtgaagagcc    480
gcttcaagcg ctttggcagt gccaaggttc tgaagaacct gtacaggaag caccggctgg    540
agagtggcgc gtgcttcgac attctaggag gaagcctttt tgagtcaaac ctggagaatg    600
aaggaagcat ttctggcagt gattcaacat tttataggca gtcagaagga catagtgtga    660
tggacacctt ggctgtggcc ctacgggtgg ctgaagaggc cattgaggaa gcaatttcca    720
aagcagaggc atatggggac agcctggaca agcaaaatga ggccagttac ctgcgggacc    780
acaaggagga gctaactgag gaactggcca cgacaatcct gcagaagatt atacgaaaac    840
agaagagcaa aagtgagcag caagtggaag aagagccagg atggccacat ccccagagtt    900
gcagcacaaa ggtggcagat gaggggacct cagcatcccc tggaggctac cgtgctcccg    960
ctgccctctg gaggtcccag tctgccttct caatcactgg agaagaagcc tgaagaccc    1020 ctccagtgga ggctccatcg aggcagccaa gggaccaagg ccaacacccg agagcagagt   1080
ctgctctgcc cagctggaag agtgtggaca ggctggatga acaaacctg gccccagttt    1140 tgcagagccc cgacgggaac tgggtggccc tgaaggatgc cgctccaccc cccacccgac   1200
tactggccaa acctaagagc gggacgtttc aggccctgga ggtggcctcc agtgtggcat   1260
ctgcctacga tgagatgggc tccgatacga aggaagactt tgactggagt gaggccttga   1320
gcaagctgtg tcccaggtcc cgggccctgc ccaggaaccc ccagcctcag cccacacagg   1380
cccagagctc tgaccaaggc cccatagctg cctccccatc ctctgcactc tccccccaacc  1440 ctgaggccat gtgctctgac tcggagacct cctccgcagg ctcttcccga gaagttgggc   1500
accaggccag actgtcctgg ttgcagagga aggcccccag gaaccctgca gctgagaaga   1560
tgcgcttgca tggagagctg gacgtgaact tcaaccccca gttggccagc agggagacct   1620
cggacagcag cgagccggag gaggcccccc acaccacaga ccggcgggcc aggaggtgga   1680
gaagagcccg actgggctca gaagagccaa gcaaagaacc atcttccccc agcgcccagc   1740
tccgggatct agacacacat caggtgtcgg atgatttatc agagacagac atcagcaatg   1800
aggctcggga tccccagact ctcacagaca ccacagagga gaaacggaga acaggctgt    1860 acgagttagc aatgaaaatg agtgaaaagg agacttcttc aggggaggat caggagtctg   1920
agcccaagac agaatctgag aaccagaagg aaagtctgtc ctctgaagac aacagccaga   1980
gtgtccagga gagctgaag aagaagtttt ctgctgtttc tctctgcaac atctccacag   2040
aagtcctgaa agtcatcaat gccacagagg agttgatagc aggatctaca gggccctggg   2100
agtccccaca gtccctcct gacagacaga aggggatgtt tcctcgtggg acagaccaag    2160
tgagactgga tgagcagctg acttccctgg aagaaaatgt ataccctggca gcaggcactg   2220 tgtatggact ggagacccag ctgactgagc tagaagatgc cgcccgctgc atccacagtg    2280
gcactgatga gacccatctg gcggatctgg aggaccaggt ggccacggct gcagcccaag   2340
tccaccatgc tgaactccag atttcagata ttgagagccg gatttcagcc ctgaccattg    2400
caggattaaa catagcacca tgtgtgcgct tcacaagaag acgggatcag aagcaaagga    2460
cccaggtaca aaccatagat acatcaaggc agcaaaggag gaaactgcct gctccaccgg    2520
tgaaagctga aaaattgag acatcttcag tgactaccat taaacatttt aaccacaact    2580
tcattctcca aggctcctca acaaacagga ctaaggaaag gaaaggcacc accaaggatt    2640
tgatggagcc tgctctggag tcagctgtga tgtactgaca ccatggaatt ccactgccag    2700 tgaccccactg cctccggccg tacacgcacag tgccttgacc caacagccat cgagtactgt    2760
atgtatttcc acctgaggag aaggcctggg gaggccacag tgcaccattg cacagggctg   2820
```

```
tcctgatacc tcatccagaa agccgtctca gacttcagca ctgcggtctt gcccactctc    2880
tgccttaggc tcccagggga atccaagaca gaaaatgaag acactggctt ccaacagcag    2940
cgctccatgt ttaagataca tattttccct gtttgctttg ctactgtatg ttgactttaa    3000
gatctttttt taaatacatt tgattcagct agtattccat gtcaacaatt tgtccaaagg    3060
aaaactgctg gagggaggtg gagggaggaa ggtgggaatt attatttaat acatcattaa    3120
tgcttattaa tctctcacaa gcatctttgt cttgcaaatc ctaagggaaa agcaagtccc    3180
tgcagtgagc actagggaca gtctaatttg gggattgctc aaccatcaag actgcaggtc    3240
tcccttcagc cacctccttc ctgctaaaag cttagcctac cacactacca gtcattccca    3300
tcgctttgca atcacaagcc acaggatgag aagttctgac tcactcatgc catgcccagg    3360
gctatctgaa acaatgtctc attaagaatt tagggttctt ccatgggctt actgacagtt    3420
gcccagatct gaaggggaaa gggtcttgag aaagaccatc actggctcaa ctttagggca    3480
ctgtccagag tcaacatgat gtggtttagc agtgatcaca tctaaacaaa gtttaggtaa    3540
atgaattatc gcagagaaaa accacatgag aaaattttg tactccaaat ttacttccca    3600
ataaatattc agcaaagtag taaaatgacc ttaaagataa aaatgattag ggaatagcct    3660
tagaaaattt ataggtataa aaaattcaag gacaaactgt gcatttaatg gacacaagaa    3720
ttgactctaa ctccatgtct gtggtttctt tgaacccata tcaaatgtat gactatttag    3780
agtgtttata agagataatg gaactgaact ttcactcaat taattgggca ttaacaacct    3840 tctttttatgt ttgttcctga tatagtctga atcttaggaa gaaggtaaaa gaaaggaggc    3900
aagagaatag ttatgatgaa tatgtgttaa gtgcctgctc tgaaggaggc aatgttcttc    3960
tcatttgaat ccttatggca accttattca ataggttttc ccatatttca gatttaataa    4020
ctgaaggcca gagagattaa tttgccaaag ccacacccttt atgctaatta tgattggaat    4080
gcatcacaaa agcctaactc tgttgttttc aacctctacg ttattttgct gctatgtgca    4140
tttccagatc tgattttctg ctaacttgtg tgctatgatc cactcctgat gggggtctac    4200
attaatcttc cagtactcct tgctgatgct gtgttatgtg tcatctaaca gaaatgactc    4260 cttttgaaata agtaaatctt tggcttttg ttctgttggt gtgattcaaa gcaaaacaaa    4320
caaacaaaaa caaattttaa gaacacaaca aaaagatttt gacttccgaa tagaatgttt    4380
tctttaagag gcatgaaaag caactattgt tgtgttacag tgttaaaaat attcagtttt    4440
ctttgacaaa aatgtgtact gtgtaagcct tgcaaacaaa aacaacaaa aagaagcag    4500 cagcagcagc ctgctgtgtg gcatctgaac ttttataaag gtttccttgt gccaaataag    4560
tgcaaagatt taatttacta ttaaaaacca taagcatatg ttatagttcc agaagaatta    4620
ttttgtcatc aagtgatttt gatctttagt gtcaatattt atatttagat taattttat    4680 aaatgaaaat atttaatgg tttaagaaaa tgaggacaac aggataatat ctttgatgac    4740
ttctgaaagt tatgcttccc ttcatgttat atgcacattg ccaagaatta ctgtcaagag    4800
aaatgataag taaaagtcat ttatgaaaat aaaaaaaaaa aaaaaaaaaa aaaaaaa      4857
```

<210> SEQ ID NO 56
<211> LENGTH: 1473
<212> TYPE: DNA
<213> ORGANISM: Homo sapiens

<400> SEQUENCE: 56

```
cttcaacact gtggaagctt tgttctttcg ctcttttgca ataaatcttg ctactgctca       60
```

-continued

| | |
|---|---|
| ctctttgggt ccacactgcc tttatgagct gtaacactca ccgcgaaagg tctgcagctt | 120 |
| cactcctgaa gccagcgagc ccacgagccc acagggagga atgaacaact ccagatgcac | 180 |
| cgccttaaga gctgtaacac tcacggcgaa ggtctgcagc ttcactcctg agccagcgag | 240 |
| accaggaacc caccgaaagg aagaaactcc gaacacatcc gaacatcaga aggaacaaac | 300 |
| tccagacggc gccaccttaa gagctgtaac actcaccgcc agggtccggg gcttcgttct | 360 |
| tgaagtcagt gagaccaaga acccaccaat tccggacgca gtaccatgat caacaggatg | 420 |
| ttactagcaa cttccttgga gcgatgtggt tgatatcaat aacttttctc tccattggtt | 480 |
| atggtgacat ggtacctaac acatactgtg gaaaaggagt ctgcttactt actggaatta | 540 |
| tgggtgctgg ttgcacagcc ctggtggtag ctgtagtggc aaggaagcta gaacttacca | 600 |
| aagcagaaaa acacgtgcac aatttcatga tggatactca gctgactaaa agagtaaaaa | 660 |
| atgcagctgc caatgtactc agggaaacat ggctaattta caaaaataca aagctagtga | 720 |
| aaaagataga tcatgcaaaa gtaagaaaac atcaacgaaa attcctgcaa gctattcatc | 780 |
| aattaagaag tgtaaaaatg gagcagagga aactgaatga ccaagcaaac actttggtgg | 840 |
| acttggcaaa gacccagaac atcatgtatg atatgatttc tgacttaaac gaaaggagtg | 900 |
| aagacttcga gaagaggatt gttaccctgg aaacaaaact agagactttg attggtagca | 960 |
| tccacgccct ccctgggctc ataagccaga ccatcaggca gcagcagaga gatttcattg | 1020 |
| aggctcagat ggagagctac gacaagcacg tcacttacaa tgctgagcgg tcccggtcct | 1080 |
| cgtccaggag gcggcggtcc tcttccacag caccaccaac ttcatcagag agtagctaga | 1140 |
| agagaataag ttaccacaa aataagactt tttgccatca tatggtcaat attttagctt | 1200 |
| ttattgtaaa gcccctatgg ttctaatcag cgttatccgg gttctgatgt cagaatcctg | 1260 |
| ggaacctgaa cactaagttt taggccaaaa tgagtgaaaa ctcttttttt ttctttcaga | 1320 |
| tgcacaggga atgcacctat tattgctata tagattgttc ctcctgtaat ttcactaact | 1380 |
| ttttattcat gcacttcaaa caaactttac tactacatta tatgatatat aataaaaaaa | 1440 |
| gttaatttct gcacataaaa aaaaaaaaaa aaa | 1473 |

<210> SEQ ID NO 57
<211> LENGTH: 2112
<212> TYPE: DNA
<213> ORGANISM: Homo sapiens

<400> SEQUENCE: 57

| | |
|---|---|
| cggcggcagc agcccatgcc tccggtgcaa cagctgcgcc tcctccggtg ccccggcggc | 60 |
| ggggggcggga gataacctgt ccctgctgct ccgcacctcc tcgcccggcg gcgccttccg | 120 |
| gacccgcacc tcctcgccgc tgtcgggctc gtcctgctgc tgctgctgct gctcgtcgcg | 180 |
| ccggggcagc cagctcaatg tgagcgagct gacgccgtcc agccatgcca gtgcgctccg | 240 |
| gcagcagtac gcgcagcagt ccgcgcagca gtcggcgtcc gcctcccagt accaccagtg | 300 |
| ccacagcctg cagcccgccg ccagccccac gggcagcctc ggcagtctgg gctccgggcc | 360 |
| cccgctctcg caccaccacc accacccgca cccggcgcac caccagcacc accagcccca | 420 |
| ggcgcgccgc gagagcaacc ccttcaccga aatagccatg agcagctgca ggtacaacgg | 480 |
| gggcgtcatg cggccgctca gcaacttgag cgcgtcccgc cggaacctgc acgagatgga | 540 |
| ctcagaggcg cagcccctgc agcccccgc gtcgtcgga ggaggtggcg gcgcgtcctc | 600 |
| cccgtctgca gccgctgccg ccgccgccgc tgtttcgtcc tcagccccg agatcgtggt | 660 |
| gtctaagccc gagcacaaca actccaacaa cctggcgctc tatggaaccg gcggcggagg | 720 |

```
cagcactgga ggaggcggcg gcggtggcgg gagcgggcac ggcagcagca gtggcaccaa      780
gtccagcaaa aagaaaaacc agaacatcgg ctacaagctg ggccaccggc gcgccctgtt      840
cgaaaagcgc aagcggctca gcgactacgc gctcatcttc ggcatgttcg gcatcgtggt      900
catggtcatc gagaccgagc tgtcgtgggg cgcctacgac aaggcgtcgc tgtattcctt      960
agctctgaaa tgccttatca gtctctccac gatcatcctg ctcggtctga tcatcgtgta     1020
ccacgccagg gaaatacagg taccatgatc aacaggatgt tactagcaac ttccttggag     1080
cgatgtggtt gatatcaata acttttctct ccattggtta tggtgacatg gtacctaaca     1140
catactgtgg aaaaggagtc tgcttactta ctggaattat gggtgctggt tgcacagccc     1200
tggtggtagc tgtagtggca aggaagctag aacttaccaa agcagaaaaa cacgtgcaca     1260
atttcatgat ggatactcag ctgactaaaa gagtaaaaaa tgcagctgcc aatgtactca     1320
gggaaacatg gctaatttac aaaaatacaa agctagtgaa aagatagat catgcaaaag      1380 taagaaaaca tcaacgaaaa ttcctgcaag ctattcatca attaagaagt gtaaaaatgg     1440
agcagaggaa actgaatgac caagcaaaca ctttggtgga cttggcaaag acccagaaca     1500
tcatgtatga tatgatttct gacttaaacg aaaggagtga agacttcgag aagaggattg     1560
ttaccctgga aacaaaacta gagactttga ttggtagcat ccacgccctc cctgggctca     1620
taagccagac catcaggcag cagcagagag atttcattga ggctcagatg gagagctacg     1680
acaagcacgt cacttacaat gctgagcggt cccggtcctc gtccaggagg cggcggtcct     1740
cttccacagc accaccaact tcatcagaga gtagctagaa gagaataagt taaccacaaa     1800
ataagacttt ttgccatcat atggtcaata ttttagcttt tattgtaaag cccctatggt     1860
tctaatcagc gttatccggg ttctgatgtc agaatcctgg gaacctgaac actaagtttt     1920
aggccaaaat gagtgaaaac tctttttttt tctttcagat gcacagggaa tgcacctatt     1980
attgctatat agattgttcc tcctgtaatt tcactaactt tttattcatg cacttcaaac     2040
aaactttact actacattat atgatatata ataaaaaaag ttaatttctg cacataaaaa     2100 aaaaaaaaa aa                                                          2112
```

<210> SEQ ID NO 58
<211> LENGTH: 36151
<212> TYPE: DNA
<213> ORGANISM: Homo sapiens

<400> SEQUENCE: 58

```
caagctgact tctcaagctc tgggatgcc tcagtgatct ctgatgtgga attagtggag        60
gctggccgtt gctcacctct acacagcctg ctggtcgtta gcgagcagga gttctgatgt      120
tcctctcatc ttgatggta agaaatttat gaaaatgcta agtcctgagg attaatagag       180
gaaatgagga ctaaatatac aaaatagtcc agaaggtggc aggtggaaca cagcaataat      240
atatgatgtt agtcatcagt cattagtgcc acagggatcc taggcgatgg ctgggaaatg      300
gcttttgcag gctgagatgg tggtagcgct tcaccctcta aggcaagtgc ctatgattca      360
atgggtgaac tcactgccac cccagcaggg tggggtgggg gttggcttgg tgagaaggga     420
gatgtcatct tgcccaagga ggcttatccc ttgtgaaagt ctggacaac acacaaaaca      480 ccaggaggaa ctgtttcgga gtgctgtctt gaatgcaagc aggcagcctc catttagatc      540
tcactgattc ttctaggata ttacaaagca ctttcttacc ccaaatcctt cagtgccacc     600
ctgccactaa atacaaagaa gaagctctgc ttcccaccgt gcagaggagc cacagggatt     660
```

-continued

```
gcatggtccc catgactgcc tctttggccc agggaaaggg cccaatcaga cagcacccca    720
gatcttaaga gaagaacttc cagtcaaaac aacagggcac ccccgtgtgc tggaaggtcc    780
aactctctcc agtcccaaga gtgttaagca tctggctaag gctttgctaa atttcccata    840
agagctgcat tgttttcttc tgtctgttag acctaggaag ttttctgggt gtggacgtag    900
ggcttttgca agtttcaaag cttccagggg attagaaacc atcattccca agcatttaca    960
agaaaatctt ttgtcccac tgcttgatat cgaaaaacaa gggtcactct tcttttcccc    1020
taaggaggga aatgggaaca ccccgctgac catctccttc tgcctcaggc actttcatgg    1080
agacagtcga gggctttggg gcctgtccta cctggtggtc tactcagtag agccatcggg    1140
ctgaaaagga gacatctgtt aaggtaactg gtgatcccat gtaaaagctt tgactaaacc    1200
acaggagctg gaaccacttt tcagtaaag catgccagga agcacaaata aagtcatgtg     1260
ctgcataagg acgttttggt caatgaggga ctgcataaat gatggaggtc ccataaaatt    1320
ataatatcat attttactg tccctttct atgtttagat aaacaaatat taccattgca     1380
ttacaactgc tcacagtatt tcagcaggaa agggcccttc ggggaggggct ccagcttgcc   1440 tctccaggtc taggtcttat cgttcttccc cttgaagttg accctacaac cttattaaat    1500
cttctgcagt taccaaaagt gataatgtgc ttggcctttg tttaagctgt gctctctgcc    1560
ttgagctgtc ctccttccct ctgctcaagt gccccatttt tcatgtccct tgggaacaag    1620
ctcaggtgtc atcactgaat tcaggtagat gcccctctta tctgtcccca gagcatgctg    1680
cacttatccc catcacagca cttctcatgc tctgttataa tttccttcct attccattag    1740
catatgagga accaagggcc atgtgtcatt catcctagta catgttactt agtggagttg    1800
cataaatact tatggaatga ataaattgac taagaggtga gctgggctca gcttgtggat    1860
gatcctgaaa gatagattgg cagactctta ccttttttgg gagtgtgcaa ccggaaactg    1920
tttattgtgt ttttgaggtg ggagataatt tatgggact gtccttttggc atgatagctc    1980 tagaatgagt gctaaggttg aatgggatgg aagagagagc cagttagtaa gccattgcag    2040
ggtgcaggtg agacagaata aactgaagtt aaataggagt aatgcgggaa cattcaaaat    2100
agggtcagta agaagtgatc acaaataacg caagggagac ggaggaatca agggtgatgt    2160
ggaggtttcc agcgtctact gaagtgagtg aatgaggatg cctcttccc actagaggaa     2220 gataggtatg ggggtggcca cagctgcccg gttgcatgga taggaactcc ttgacttacc    2280
ttttattaga agatgggtaa tgatgactcc atcactgtaa ctgcaatcta ttctgggtga    2340
agagtgccca tacggtaaat gttttaaaat attctgaata ttgcccctgg tcccaaggga    2400
tgaaggcatt gtgaggagt tttcccttaa gcatagttga aataggagaa aaaaaaaga    2460 aaaggaaaaa tcagaagtta tgtcttagaa gggtgttgat gtggattggt ttaccagggt    2520
tgctgtaacg aagcagcatg gcctgggtgg cttgaacaac agaggtttat tttctcacag    2580
ttctggaggc tagaagtctg agatcaggct gtcagtgggt ttgcatcctc ctcaggcctc    2640
tctccgggca tgtaggtggc tgtcatctcc ctgcgtcctc acagggtctt tcctgtgtgg    2700
gtgtctgtgt cctcatctct tcttctaagg acacaagttt gttttttggat tgggatccac   2760 cctaattact tcacttaact ttaatcacct cttaaagac ctacctccaa ataggggtcac    2820 ggtgtgagat actgggaagt taggacttca atatatgcat tttggtggca ggaggcgcac    2880
aattcagccc gcaacatgag gcatgagcaa aatataaat ttaaacaatg ttggcaaaaa     2940
cagattcaaa agcaaaatgc aacgccaaag catgaggaaa gggaagaagt tttgatagt     3000 aggcatggat gaggtggtcc cgagggagag aagaggctgg ggcaccacgc ggaggggttt    3060
```

```
ggtagaccct gagtggtttc tctcattgta gagggtcagg aacaatttga acacagaaca    3120
actgaagagc caggcttgat ggctctgtta aggaaaagac acttttagga cgtgcagttg    3180
gaccttttca agaagctgtt ggaggtcagg gtctgagttg agaaaggagc ttggtcctgt    3240
aagtcatcga cactcagttg cttctggatc ccatcctcac ccctgcacc gcggggtcct     3300 tctcagggaa cgggccactt cccgatgctc cctgggctgc catcagctgc catgaacact    3360
ctgcttagtg gaggctccgt ggcctgtgaa ttagcatcaa cctgaaataa caagcagggg    3420
cttcctatga gtcagccata gtctgttcag agatgctgcc taaagggtct aaatccaaag    3480
gcattaatta atttgttccc agggtccaca gcatggggag ctcaagccct tccatttccg    3540
ctcattgata ccggctgggt aatattatgt gggttccatt tttaatgtag aatgccttat    3600
ttgacaaaca tccagacagc acccccaact ttgttttctt gagcagaaga gagaaaacaa    3660
gagatgaagg cattgatgca tcagccctgc agaaaaatgg caaaggttac aatatgttat    3720
atttagatcc gcaatttgcc gaaggaagat aattgggaaa ttaagttgcc tggttgggaa    3780
atcagccgtc cttttgtttt tgtccggttg tgtagtctca taaatgttca gggcttcaat    3840
acctttaggc acttataatt aatttttttaa aaattggaag attcagtata taagctgcct    3900
gatttaatga aataagtcaa aaggagaaaa aagaagggag tttcttgcag taattggttg    3960
ttacattttt ccacattgcc attctaattc attcctttga aaagagttcg tttttcagat    4020
tctataagta cccatggcaa taagtgctat ttataataaa gagacataat gagtctcagc    4080
tgcacccagg gaggttgcag caggtcagga gcctctctgt ctgctccatt gttgctggga    4140
gagagggtct tgttccaagg gttgggtggg aaacaggaat tccccacact gtccctgaaa    4200
ttgtggagtg atgaactagg gagggaagtc ttaactggaa ttttcaata ttagattttc     4260 cagagacttc attcagccca ctcttcagta gggaaataaa tcctttatgt agaaaaaaaa    4320
tcaaaccatt tccttttgaa taaggtaatc tctgaatctg aggaaccccg agataagatg    4380
atgtattagc ctgctcaggc tgtcataaca atgtaccgca gactgggtgg cttcaacgtc    4440
ggagatttat ttccttgcag ttccggaggc cgggagttct agaatacatc aaggcatcca    4500
cagggttggt gtcttctgag tcctctctcc cgggcatgca gggggctgtc atctccctgt    4560
gtcctcacat ggtcttcacc ctgtgtatgt gtgccttact ctttgcttaa aaggacatca    4620
gtcatattgg gttagggtag agcctcattt taccttcact accattttaa ataccctatc    4680
tccaaacaca gtcacattct gaggtactgg ctctgcatat aaatttgggg ggacacattt    4740
cagctcataa tagatgtgca tcttattttt gaaaataaaa ttacagaggt ctttcctctt    4800
attccctttt cctctttcac cattcctgcc tttcctgtat tagctgagac agtaattcat    4860
attgtcagag cacacactgt ctctctctct cacacacaaa cacacatacc tccacacact    4920
ttatctttcc tgcctccaaa ttattttctt gttattggaa gcaaaatgc attttttcctt    4980 cataggcacc ttcttaccca gtcctcaatg ggtgctgtga tcaaggagg ccaccacagc     5040 tctattagct catgcccaaa taaagccaaa tctcacacct tccacaagtg acctgtgttg    5100 ctccttcct gaggttgttt cacagagaag agacccaagg ttaggctggc tgttggcctc     5160
catcagtgat agtgatggct gggtcacagg ttgctgaagg agtcaaggga ctcattcaat    5220
actggatgct tctgttcctc tttcctctgg ggctggacta attaaggaaa atgtttcct    5280 ggctgttcag gttcctccca tgctaattca ggcctattct tgcagatgca tacagttatg    5340
acttcattat gcttgttggt atggaaatag aggtaagatc aggtgcccag tggtctgaaa    5400
```

```
aatgttgaca tgcattttttg agcctgtcca cagttgtcgt taaagccttg tcagacttcc    5460
ctggaggac atttagagtg agaaaaaaga gaacctagga aaaattcctg ggaaacatca      5520
gcatttccag ttcagctgca tgcttgcaga tgcgaaaaag tcagggaagt ggaagccagg     5580
aaggtgagag gaaaaccggg atgggaggag ctgtggagat caagggtggg gcaagagttt    5640
catcggggag gggcagcagt ctgcagtggc cagggttgtg gatacatgaa gcatatgatt    5700
cctgactaag tgaggatttc tggagtgcgt catctaattt tctctgaact cattttgcaa    5760
gaatttccta gggattccat tggggcgggc gaggttcccc ttgatgcttt catgtagtag    5820
ttggctcaga gggaatggtg gaggtaggag gcatatagct cctcttcaag tgccacttca    5880
aatccactag gtgttatctc tcattttggc tactgagcta catgttgtgc ccccgttcca    5940
gcaccttcca gcaggtgtaa ctgacaatac tcaccccagg ctcacacaca tagcctttgc    6000
tttgtgctgc tgtcttctcc attggtatgg catggagcat ggccattagc acctgctcag    6060
tgctcatgag tgcaccagag ttatttccct gtgggcagct tgtgaccaga gtaggtcaga    6120
agctaatgga gaaatgcttc ctcctttcct cctctgggaa aaaggtctgc agaattgagc    6180
aactggttgc ctgtggtgat ggccaaattt ctgaacacat cattagaatg ttagggtgac    6240
tctctcctcc tctgctttgc tttctctcac ccttggtcca tggaccaccc tccctactga    6300
agtacttgca actcaacttt gggggaaact gtggataaga gaattagtct gggaagagtt    6360
ggattactta aaagtcaaag aggaatacgg accccattgc tggtgataag aggagtggtg    6420
ataatccttg gtatgcaaca gcttcctgtt actatggctc ttgcctgtgg tagagtgatg    6480
tgtggcacag gtgaaggta atgcattaac ttaggtcagc agctggcaag ccatcgtccg     6540
tcgcctattt ttgtatggcc tgtgagtata aaatggcttt tgcattttta gaggattgga    6600
accacacaca cacacacaca catacacaca cacacacaca cacacacaga atatgcaaca    6660
gagactgtgt gtagcctaca aagcctaaaa tattttctgt cttccattta ctgacgaagt    6720
ttgctgaact ctggtgtaag tgatagggta ccatgtgaac aatgagaaca tgaagaatgg    6780
ccatggcagc tgacagctaa cggctagata gtactagtga acatgagtaa cactcacaga    6840
atataagcaa taattagaca aggccactgt gtcaccacca tggaacaaga cagacaagac    6900
cacttcatga ctgtgagtga aacaagatag agacaaggac accctgcaac tcccccctcca    6960
aataacttaa catgccactc ttctaacaag aataagagac tatcacttcg tgctgattgc    7020
aactctatct gtgattcaat cctcctgcct cctaattaaa aattaccaag gaaccaaatc    7080
actgaattgt tcacataccc taacagcatt cagtctagaa ctgtctttgt ttccttcaac    7140
tctccctcca atcacctggc acaaggtcaa attctacaaa aatcctatct taattcctag    7200
tttccaagac atcccacagc cctacagaaa taaagaccac ccaactgaga acaaggatgg    7260
tgatttattc ggagcttgct gtagtgaaag agtcggccac catcactggt gtttggcaga    7320
gactcaaagg caggcagagg ggtgggagag ctttacagtg ggcaaaaaag acgtcttcag    7380
gtgtgcccca attggaggct gttggcctag agaagctgga ggtggccaag taggagcagg    7440
gcaggctatg tgattggttg gggacatatt tgaccttctc tggtttgtcc tgaattggaa    7500
gtggggacaa aaatcaagaa atatgtcagc tattaatcat gtgctggtca ttttgggctg    7560
attgctacag aagttgtggc tcagagtctt attgccacct ctggtccagc cactggccat    7620
gggtgtgttc agttttcagt tctctggaat gccttctttt ctctgcagta agctcaatga    7680
acttggaagc agattctccc ccacagcctc tagggaagag cccagctatg tcaatgctga    7740
tttgggcctg tgagacccta agctgagaac acagttaagg cccccagac ttctgatctc     7800
```

```
cagagttaga aataaatgag cactctttca agctgctgag tttatgctaa tttgtttgac    7860
aacaggtgat tcctgagggt cactggttac tggacttgga aaactgtgtg agtgcaagca    7920
taattattag gatcacagtg tatgctgggt tttgttaact gcattgacag ccttaaagaa    7980
aatggtaccc tcagatcagc caactgtcaa ctcaaggtgt gctgtgaaag ctggaggcct    8040
gtagaaagag tttaaagaac catgacctcc tttagccaga ggaagactag atatctacaa    8100
agacctcact tgaggctgat ccttcctcac aagatggtgt tcatcctcct gagggtcttt    8160
gctgtgaccc cttaccatct ccagaccaat gaccaggatc aggcctcata gccctgcctg    8220
ccctgaaaac ataggggataa aacagatccc agtggttatt tagcaaatgt tctgcatcct   8280
ctatgtctgc atcagttact acctcaaaac agctggcatt ttgcctttt tcccccacta    8340 atttaaagcg cattctgaga gcaggggtca gcacactctt tctttaaggg tcagattgta    8400
aatattttca tttctgcaaa ccatttggtc tttgttgtta tcctccactt tgccactagt    8460
agacatagat aatacacaag cgaatgggca tggcttttgt tccaatataa cttggtttac    8520
aaaaacagaa acaggccaga tttggcccac aggctatagt gttccagctt cagtcttgga    8580
aaatcattta atctctctgg gtttcatttc tacacctgta aaattagagt attgttctaa    8640
gacaatgcct ctcacactcc agctagcgtt agaatcatgt ggagagctac tgaaagcaca    8700
gattcttgca ccttactccc agtgattcca gttgaatagg tctggagtgg gatctgcatt    8760
tttaacatgc tcccaggtaa aactagtgcc gctggtccag ggaccatgct ttgagtagca    8820
gaagtcttgg gcagtacttc tcatccctgg cttcagagga gactcgtgct gagaactttt    8880
aaaaagatac tgatccctct gttccaccta agaccaatta aattacaagc agaatccagg    8940
cttctgagca ttttaaaatt tccccccaagg gatcatgtac aatcagggtt gagatccact    9000
ggtggaggtg agctccacag ccctgccctc caagtatgat tcttgatgag tggccttggc    9060
atcagcacaa cgtaggaact tcccagtaac acacagtctc gggctccacc ttgacctact    9120
gaatcagaat ccacattata acaagatccc ttggtgatgc atgaacacat taaagttggg    9180 gaaatgggt tctacaggaa ggaatggatg aatattttca caggttcctc ttctcctact     9240
acacaccagg cactgggtgg gctatactta agtcacttaa acttgcctgt gtaggttttc    9300
tactgctgtc ctgacagatt aacataaact tagtaactta aagcaacact catttatttt    9360
ctcacagttc tgtggattgg cagtctgggg aggctcaagt gggttctctg ctcaggatct    9420
cacaggccca gagcagggta ttgctgtgtt aggttcttaa ctcaggcttg gggaaggaat    9480
ccacttctaa gctcaattac gttttttggca gaatcaagct tcttgcagtt gtaggactga   9540
ggttgctgtt ttcttgtgag ctgttggcca ggggttgcct tctgcttcta gatgtctctt    9600
tgagttcctt ttaactttta cattatgttc aaagatagca accattcatc atatcctcct    9660
catgcttcca acctctctga ctcctccttc cgctactagc tagtgaaaac ttgcttttaa    9720
agagctcgtg tgattatatt aaactcacct ccataatcgc caattttact aattcaaggt    9780
tgatggatta gtaaccttaa taacatctgt aaaattcctt tttccataaa tgtgttatct    9840
cgtatattcc cagtcactgg cattagggct gaaggtcttg ggggacattt aagaattctg    9900
tctacctcaa tgtaccatgc cacttacacg tcagtcttag agtcagattt tgaatctagg    9960
tgtgtctgat cctaaggctt atatgaacat tatttaccca atttgtttct ctgtggtaag    10020
aacaaaggtg ttctttgttc agagaaattt atagttatca aagagctttc acatttattt    10080
tattgtttgg tctcataaaa gacctttatt aggtattatt attctttta tgggggattg     10140
```

```
agaatgttta attatttgtt caagggccta taagcagaat atagaaaatt caggactgaa   10200
gaatgggtct cctgattcca aatttcatac ttttccttt atattaccac aatttttataa  10260 tttcttattt agatcattct tgttgtctaa ttagaaaaca aatttaccag gatagaataa   10320
aagaaactag cagagtagtt gtagatagga tgcaaatgtc tgaatcctgc agtgggccct   10380
gcacagaaaa atagacccac ctgttacgct aattgaagga aaaactctgc tgaaattcag   10440
agaagtactc cattcaggtc ttaaaaatta ttgttcttaa agaagacagt cattcaattt   10500
ttaaatgtaa tttagaaaac aaccaattca caaaacaaac acttttact gaattacaag    10560 tcaatcatga ccttactttg gagaaatgac aggaaatatt ggcaaatcat gtggatgcaa   10620
ctcacatttg tgataagaaa gttagcctgc tcccatggat gaagcttaag gagaatcata   10680
aaaccatcct ccttctagtg actatctttc agttcattct ctttttgttt caaaagcaaa   10740
gaaaccaatg tgacctgaat gaactataat tacaaagcta agattctttc agagggcagg   10800
atgatatcta ctggttgggg ttttcttggc atggccaact aggattctgg tatatagggc   10860
atgtctctca tgagtcccct aataatgtaa tcattttttc ttctccatat ggtgcaaaag   10920
tcatatctag tgagaaagta tccttacatt gccagtttag aagttatttt atgcttaaaa   10980
aatggcccag tcagttgttc aaataaaaaa cagctgaaaa ttcaatatct tgggctgttt   11040
ccttgtcatc atttatagat gtaaggggtt tcattacaat ctgagaggca gtctatgatt   11100
taaacaaatt atcaaaaaaa ttaggccttg gtcagctcaa ttttattaaa agccttcaga   11160
tcttaaagga tcaatgacta caagagaaag gttaacccc agggctcctg gttggtgaac    11220
aaacacatca aagtgaaatc agagttaaaa gctattgttc ccttggctaa cttttgcctc   11280
tgtcatattc agttgatttg aagagatgag gaatgataaa caggaccagg ttacaaacat   11340
agaactgtta cattttgttc atttagccag gagctttatt cttttgtttt tcatgagatg   11400
ggtcatttta atagtcaacg tgttgacga cagtcaccat tcaatctgtc atttctaata    11460 cagtcttcc taggagaata tttctcacgt gtttgacaga aaacattatc tgtccatcat    11520
ttccatggat tcctgggtct cacgggcaga aggacaaggc agatatgagg cggatctggt   11580
aaagtaagtc attgtgtact cttgtatt gtttgaagat atttggtctt tttcagtcat     11640
atatgtgatg gagaaccagt tgttagaaca atgtgtatat tgatggagaa acaggtgggc   11700
cagagtggtc ggtagtctgt gtgacaaaca gtgatgccac tttcactatc tgaaaatgaa   11760
tgaatatatt catagtagtg ggcatgcaaa ggtaataaag acctgacccc caacatcaat   11820
aatataataa tgatgaattc atattctaaa tctgatcatt taaggaaggc catccatatc   11880
tccatcacaa tcacttaaac aaatgcaaaa atggatattc tttctagaat atttctgatg   11940
aaattgcttc tgaaggctgc aaattagtgc tcaagaccct gttgaaaagc agtttcctgt   12000
attcacttat gaagtcaaat gcagaaatta tatttatttg gatttatttt atagcagaga   12060
gaataactta aaaactgaca tagcattctt ttcaaatctg aactcaatgt ctgattttg    12120 gaagattcat atcagctcta ctcttataaa tcagaaaaca aaacaaaac aaacaaacaa    12180 aaacaacaa caaaaaaga aaaacaggcc cagacaccag cagtgaccca gtcaaccact     12240
ggccagtcaa tatgagagcc agctggttct tctagtgaaa ccttcacctt tctaatcaga   12300
gggtttcagg ttttgctctc tattgagtca attgcttgag ggtagaaaaa gaaaatcttc   12360
gaattgcatt acataccact cctttcccctt tctatagatt tcccctctc tcctttccag   12420 gaatattgat tttcttccct gggttctga aaaagctttt ctcccaggc atctttattt     12480 ggtttgctga ccaaagcatt attcacactt ctcctgcggc cacgccaatg ccacacccgc   12540
```

```
tgcaaggtgc tcccggtctc ctacctctga acaacagtgg tctgaatctc tgacttgagc    12600
cgtgcagccc tttgaaagaa aagtcattta ggagctcagc cctctgagga tgtaaagccc    12660
gtcgcaggtg cttgttttgt ctgtctccgt gtgtggaaga tgccttctgt gaggtcctgc    12720
gcctctccgt aagcagctga gtagttcctt gggctgacaa atactttgt tgtggctcca     12780 ttacacaccc agggcaacct ctttagctgg attttgcaga ccgggaaatg ggctctgagg    12840
ggaagtcacg cctcatctca aggtttactg aggagccacg aggaggcccc accgctgcca    12900
cagctaactc atggcctccg gccaggaagt ctggagattt taagaccata atgtcagcca    12960
gggtgacctc tggaacctgt tcaccccttc acccgttgtg aacaagagag ctgaatagcc    13020
actatcacag ataataacaa cagctgacat tattaatagg atgccttaca ggctgtaaaa    13080
tactttcaca aacaggatct catttgatcc tcataatctc aacatgaggt gcgtaaagca    13140
agcaattatt actaatctcc ttttacagaa gagaaaagga agtcctgaga gatgaatcca    13200
cttctgggag gtctgacaac gttcagcttt acctaagcca tggtcaggaa acttttctgc    13260
gttccaggaa atggccggcc acaacgactg gcccttccct ataaaaactt acaaaaccct    13320
cacaggtgac ctccttgttt acctatgaca gaaccagaca cagtgccaga tcctccaaac    13380
tcccattctt tgccttatat gtaatcagtt gaactgtttg tatctactga ctaatctaga    13440
caaggtactt gctaacttga cctgtttaaa agttcgaaat gccaaactttt cttcttttt    13500 ttttttttc ccatcccacc ccacccagat ggagtttcac tcttgtcacc caggctggag    13560
tgagtgcagt ggtgccatct gggctcagtg caacctctgc ctcccgggtt caagcaattc    13620
tcctgcctca gcctctagaa tagctgggat tacaggcatg tgccaccaca cccggctaat    13680
tttgtttgtt tagtagagac agggtttcat catgttggcc aggcttgtta caaactcctg    13740
acctgaggtg atctgctgcc tcagcctccc acagtgctgg gattacaagt gtgagccaca    13800
gtgcctggcc cgaaatgcta aactttcatc aagatattgc aatagtcttt tctaagaaag    13860
ctcttcctta cttaacttgt gcctggcccc aaatgctaaa ctttcatcaa atattgcaat    13920
agtcttttct aagaaagctc ttccttactt aacttgggat tgttttatc tgacacaggg    13980 cacagggtaa agatcagagg tggcttcctg tcactcatcc agccagccac ccagctatgg    14040
ttacccacag ggcctgatag ccatccctgc cagcggtcag ggttgcattg tggcccccac    14100
tccaggcctt gcttattgca ggcttggttc ccatggctgc tctctgtgtt cttgcaacct    14160
tgcatcctgc cagaatctct ggaagaaagc tcttggcga gaaatgaaga acaatcccaa     14220
aggtgctcca ggaaagttca ttattttgtg tactctggtg tcttaccttta atcagagaac   14280 agttgtctgt gatcctcaaa gagggaatta aagggaggaa tggaaccaga attcagtgac    14340
aactggaatg agtgactgag gtgtagcgtc aatcatcaag gttattaaaa ctacttaggg   14400
tgcgtctgga aaaacatga gccacaaata catctggggt tgttttttcca aagaggtttt    14460 tgggagattt agtatttata catttcctta gagggaaaag gcatgtggaa agaggggcag    14520
gtaggcagtt ggcaaatact acattttaca taagataagg caaatgaaga gagaaagaga    14580
gtaaaggaat agtccatttt acttatgtct ttgttctgca cctgggagga agttcttcat    14640
gacatcagtg tggaatcaac aaactttagt tttaggagct aggcttagtt tgtagaccta    14700
cagttataac tggtggttct gttgatggga tgccagtgaa gaatgtactt aggaatgatc    14760
tgtgaggact gtccttcct gatgcctgag tccttttct tggggtgagc gggggtaca      14820 aaataggagc atatatttat ggagtacatg agatgttttg atacgggcat gcaatgtgta    14880
```

| | | | | | |
|---|---|---|---|---|---|
| ataatcatgt | catggacaat | gaggtatcca | tccccctcaag | catttatcct | ttcttttatg | 14940 |
| aacaatctga | ttacactttt | ttacttattt | taaaatgaac | aattaagtta | ttattgacta | 15000 |
| taatcacctt | attgccaatg | tttgtcattc | tgtgcctggc | ttatttcact | tgatagaatg | 15060 |
| ttcaccagtt | ccatccatgt | tgctgcaaat | gtcaggatct | cattctcttt | taagactgaa | 15120 |
| tagtgctcca | ttgtgtatat | gtagcacatt | ttctttatcc | attcatgtgt | tgatggacac | 15180 |
| aggttgcttc | caaatcttag | ctattgtgaa | cagggctgca | acaaacatga | gagtgcagaa | 15240 |
| atctcttgca | tatactgatt | tcctttgttt | tgggtgtata | cccaacagtg | ggattgctgg | 15300 |
| accatatggt | agctctattt | ttagttttt | gaggaactttt | caaactgttc | tccattgtgg | 15360 |
| ttgtactaat | ttatattcca | actaacagtg | taggagtgtt | ccctttcctc | cacatcctcg | 15420 |
| ccagcatttg | ttactgcctg | tcttttggat | ataagccatt | ttaactgggg | tgagatgata | 15480 |
| tctcatggta | gttttgtttt | gcatttctct | gatgatcaat | gatgttgagc | acttttttgt | 15540 |
| atgcctgttt | gccatttgca | tgtcttcttc | tgagaaacct | ctattcaaat | cttatgtcca | 15600 |
| gtttttgat | cagattatta | gactttttcc | tatagagttg | tttgagttct | ttatatatgg | 15660 |
| cgcttataaa | tcccttgtca | gatcggtagt | ttgcaaatat | tttctcccat | tatgtaggtt | 15720 |
| gcctcctcac | tttgttgatt | gtttccttg | ctgtgcagaa | ggttttacc | ttaatgtaat | 15780 |
| cccatttgtc | cacttctgct | ttggttgcct | tgcttgctgg | gtattactca | agaaattttt | 15840 |
| acccaaacca | atgtcctgga | gagtttttc | tatgttttct | tgtagtaatt | tcatagtttg | 15900 |
| aggtcttaga | tttaagtctt | taattcattt | tgatttaatt | tttgtatatg | accagagata | 15960 |
| gggggtctagt | ttttcctgc | atatgaatat | ccagtttccc | cagaaccatt | tattgaagaa | 16020 |
| actgtctttt | ccccagtgta | tgttcttggc | accttttattg | aaaattcaca | tattgtaggt | 16080 |
| gtgtggattt | atttctgtgt | tttctattct | gtttcattgg | tctatgtgtc | tgttttaatg | 16140 |
| ccagtaccat | gctatttgg | ttactatggt | tctgcagtat | aatttgaagt | caggtaatgt | 16200 |
| gattcttcca | gttttgttct | atttgcttag | gacagctttg | gctattctgg | gtgttttgtg | 16260 |
| gttccacata | aatttagga | ttgttttttc | tatttctcta | aagaagttca | gtggtatttt | 16320 |
| gacaggtatt | gcattgaatc | tgtagattga | tttgggtagt | atggacagtt | taataatatt | 16380 |
| gattcttcca | atttatgaac | atggaatatc | tttccgtttt | tttggtgttg | tcttcagttt | 16440 |
| ctttcatcag | tgtttgttg | tttcattata | gagatctgtt | gcttcttag | gttaattcct | 16500 |
| aggttttaa | ttttacttttt | ggcttttgta | aatgggattt | acaaaaattt | cttttcagg | 16560 |
| ttgttcactg | ttggtataca | ggaatgctaa | tgatttctgt | acgttgattt | tatatcctgc | 16620 |
| aactttacta | aatttgttta | tcagttttaa | tagttttttg | gtggagtctt | taggtttttc | 16680 |
| caaatataag | atcatatcat | ttgcaaacaa | ggagaatttc | acttcttct | ttccaatttg | 16740 |
| gatgccattt | atttctttct | tctgattgct | ttagctagga | attccagtag | tatgtttgat | 16800 |
| aatactagtg | aaagtgggca | tccttgtcat | ggtcatgttc | catatcttag | aaaaaagctt | 16860 |
| tcagttttc | cccattcaat | atgatacaag | ctgtgggtct | gtcatatatg | gcttttatta | 16920 |
| tgttgaggtg | tgtttcttct | acacccagtt | tttttagggt | ttcttatcat | gaaatgatgt | 16980 |
| tgaatttat | tgaatgcttt | tttggcatca | attcaaaaga | tccttatatc | ctttattctg | 17040 |
| ttttatcctt | tatcctttat | tctgttgaca | tgatgtatca | tgttgattaa | tatacatatg | 17100 |
| ttgaaaaatt | cttgcctccc | agggataaat | cccacttggt | tatgatgaat | gatctttcta | 17160 |
| atgtgttgtt | gaattcagtt | tgctagtatt | ttgttgagga | cttaaaggcc | agagattttg | 17220 |
| gcctgtggtt | ttcttttttt | gagtgtcttt | gtctggttttt | gcattataga | atgaatttgg | 17280 |

```
aagtattcac ttctcctcta tttttcaaaa tggtttgagt aggattagta ttagttcttc   17340
cttaaatgtt tggtagaatt cagcagtaaa gccattgggt cctgggcttt tctttactga   17400
gagaattttt atttgatctc attacttgtt attggtttgt ttaggttttg aatttcttac   17460
tggcacaagc ttggtaggtt ttatgtgtct agaaatttgt ccatttcttg gagaaattcc   17520
aatttattgg cctatagttg cttatagtag ccactaatga tcctttgaat ttttgcagta   17580
tcagttgtga agtctcctat ttcatttctg attttatgtt tttgtacctc tattttttaa   17640
attagtttga ctaaaaggtt tgtcaattgt gtttaactat aaaaagaacc ttttgtttt    17700 attgatcctt tttattattt tttttcattt caatttcact tatttctgct ctgatcttta   17760
ttacttttct tttactaatt ttgagtttgg tgtgctcttg ttttctatt tctttaagat    17820 gcatcattag atcacttatt tgaaggattt ccccttttt gatgtaagca tttgtagata    17880
taaacttcat cttagtactg cttttgctgt atcccatagg ttttggtatg ttgtttccat   17940
taacatctgt ttcaagacat ttttcaattt ccctcttaat ttctccattg atccactagt   18000
cattcaggag catattgctt aatttccatg tgtttgtgta cttcccaaaa ttcctcatgt    18060
tattgatttc tagttttatt ccattgtggt cagagaagat gctggaatt atttaattt     18120 tttgaatgtt ttaagatttg ttttcacct aatgtatggt ctacgcttga gaatgatcct    18180
tgcactgagg aaaagaatgt atattctgca gccattggat gaaatgttct ataaatatct   18240
attagatcca tttggcctat agtgaagatt aagtcggatg attcttggtt gattttctgt   18300 ctaaagatc tgtccaatgc tgaaagtggg gtgttgaagt ctccagctat tctcgtatta    18360
gagtctatct ttctctttag ctctgacatt tgccttatac atctggatgc tccagtgttg   18420
gggacatata tatctaaaat tgttattcat atattatctt gctgaattgg ccctttaatc   18480
attatatagt gaccttgttt gtcatttctt atagattttg tctcaaaaat ctatttttgtc   18540 tgaaaatata gtgactcctg cttatatcag acaaatttga tatttttcca tcccttatt    18600 ttcagtctgt gtgtgtctttt ataggtggtg tgtttcctat aggcaagata tcagcaggtc   18660 ttgcttttttt cattcattta gccaggctat gccttttaat ttgggagttt agtccattta   18720
tattcaatgt tattattgat aagtaaagac ttcctcctgc cattttgtta ttgttttctg   18780
gttgttttgt ggtcttctct tccttctctc tttttcttcc tgtattcaat taactgaagg   18840
tgattttctc tggtgatatg atttagtttc ttgcttttcc tttttttgtgt atccattgta   18900 tgtttttttgg tttgaagtta ccatgaggcc tgcaaatact agcttataac ccgtgattgt   18960
aacccaatag caacttaacc actgtttgca taaataaaca agcaaaaaga taactaataa   19020
acactctaca cattttttt tttttttgag acagtgtctt tgctctgttg cccaggctgg    19080
agtgcagtgg tgcaatctca gctcacggct ctttctgcct ccatattcaa gtgattctca   19140
tacttcagtc tcccaagtag tggagattat agtcatgtgc cagcatgccc agctgatttt   19200
tgtgttttta gtagagatgg ggtttcacca tattggccag tctggtctcg aactcctgac   19260
ctcaagtgat ccgcctgcct cagcctccca aagtgctggg tttataggca taagccacaa   19320
tacctggcca acattctaca tcttaacttc atcccccac ttttaacgt tttgtttat     19380 ctatttacat tttcttatac tgtctatgtc ttgaaaagtt gttctagtta ctattttga    19440 ctggttcatc atttagtctt tctacttaga ataaagtag tttacacacc acagttacag    19500
tgttgtaata gtctgtgttt gtatacttac cattaacagt gagttttgta tcttcaggtg   19560
attacttatt gttcattaac acccttttct ttctgattga agtactccct ttagcatttc   19620
```

```
ttgtaggaca ggtctagtgt tgatgaaatc ctcagctttt gtttgtctgg gaaagtcttt   19680
atttctcttt catgtttgag gggtattttt tgccagatat actgttctgg ggtgtacatt   19740
ttcttctttc agcactttaa atatgtcatg ctactctctc ctggcctgta agatttccat   19800
tgaaaagtct gctgccagaa gcattggtgc ttcgttgtat gttaattgtt cctttttctct  19860 tgttgctttt aggatccttt atccttgatc tttatcctga atttgattat taaatgcctt   19920
gaagtggtct tcttcgggtt aaatctgctt ggtgttctat aactttcttg tacttggata   19980
ttgatatctc tctctaggtt tgggaaattc tctgatatcc ctttaaataa actttctgcc   20040
cctatgtctt tctctgcctc ttctttaagg tcaataactc tcagatgttc ccttttgagg   20100
ctattttata aatcctgtag gtgtgcttaa ttgtatttta ttcttttttc ttttgtctcc   20160
tctggctgtg tattttcaaa cagcctatct tcaggctcac taattctttc ttctgcttga   20220
tcagttctgc tattaaaaga ctctgatgca ttcttcagta tgccagttgc atttttcagc   20280
tccagaattt ctgcttgatt cttttttaatt acttcagtct ctgttaaatt tccctgatag   20340
aattctgaat tccttctctg tgttatcttg aatttctttg agtttcctca atatagctat   20400
tttgaattct ctgtctaaaa ggtcacatat ctctgtttca ttaggattgg tccctggtgc   20460
cttatttagt tcatttgata aggtcatgat ttcctggatg gtgctgatgc tagatgttct   20520
tcggtgtctg ggcattgaag agttaggtat ttattgttgt cttcactgtc tgggcttgtt   20580
tgtacccatc cttcttggga aggctccaga tacttaaaga actagcgtgt tgtgatataa   20640
gctgtatctg ctttaggggg cacccaagcc cagtaacact gtggttcttg cagactagca   20700
gagatatacc atctggtatc tcttggtatt gatggtcgtg acaagatcg aggagaattc    20760 tctagattac caggcagaga ctcttgttct cttcccttac ttcctcccaa acaaacaggg   20820
tctctctatc tctgttctga gccacctaaa gctggaggtg aagtgacaca agcacccctg   20880
tggctaccat cattatgacg gcacttggtt gaactgaagc cagcacagca ctgggtctca   20940
cccaaggtct gctgtaacct ctctctggcc actgcctatg ttcactcaag gcccttgggc   21000
tttagagtaa gcagatggca aagccaacca ggcctttgtc ttttccttca gggcagcaag   21060
tttgcccagg cccctggagg gtctagaggt gccatctggg agtcagggac tacagtcaaa   21120
aaccttagaa gtctacttgg tgttctactg tattgcagct gagctggcac tcaaaccaca   21180
agacacagtc cttcctgctc ttccttcccc tttccaaagg caaggagcc tcaccctgaa    21240 gtccctgcca ccacaggtca cagggagtac tgccagacta ctgccgatga tcccttaaga   21300
cccaagagct cttcagtcag cttgtggtga atgctgcctg gcctgggact cacccttcag   21360
ggtagtgggc tcccttctgg acacaggcag gtccagaaat gccatccaag agtcaagttc   21420
tggaataagg gaccccagga gcccacttgg tgctctaccc ttctgtggcc aaaccagcac   21480
ctaaggtgaa ggacaaagtc cccttactt ttccttctgc ttttctcaag cagaaggact    21540
ctcttactag agctaccata gctgggaatg tgccgagtct cacctgaagc cagcaagtct   21600
cagaggctca ccaaggccct caacatagtt cctgggtatt gctgctgttt attcagggcc   21660
cacgggctct tcagttagaa ggtgttgagt gctggcagga ctgagttctt cccttcaaga   21720
cagcaggttc ccttctggcc cgggatgtgt ctagaaatgt catccaggcg ccaggtcctg   21780
gatcaaagcc ctcacaactg tgactggtat cctatcctgc tgtggcttag ccggtatcca   21840
agatacaaga caaagtcctc cccaccctc cctctcctct cctcaagcag aaggaagggg    21900
tctcttttgg agccacaagc tgtgcagcct ggggttaggg gaggggcgat gccagtactc   21960
ccttgtcttc cccagcttgt gtctcagtat gtcgcccatc cccagtccac tgtctctggg   22020
```

```
cctggttcag cagtagctct tgcctaagag ttgcagttcc tgtggcctag actgcttttc  22080
aagtttactt ggagatacag agcgctgtag ccctcagtgg tgaggtttgc agaaactcaa  22140
gtttgcacgg ctgggatctg tgatcctttc tggctagggc tggtttaaat gttccctctg  22200
tgggtgagag tgagctgagt taggtccttt cggttttcct ttctgctcta acaggacagc  22260
actgagttca gtgcttcaca attgctgtgc tctccctcct ctagtgccta gagatgctct  22320
ccacaccaca tcacaacggt ttttcctgcc tctgaagtta aaaccaggta ctatgagggc  22380
tcacctgatt tttggttctg atgaaggttg tgtgtgtgtg tgtgtgtgtg tgtgtgtgtg  22440
tgtgtgtgtg tgtaaattgg tgtccttgaa gggaggatga tgggtggagt cttctatttt  22500
gccatcttgc tccacctcca cctcacctga ggccttttac ctctctctga ggacccgcct  22560
aatgcgtaat gctggtaaca ggtattcatt tgggagaagg tgttgcagtg atcttccctt  22620
ttgcataaga attttggagg ggtcctgaga tactttaatt aattgaagaa taatcccaaa  22680
tgttctccag gaaagtttat gttgttttgt ttatgctggt ggtttacctt aacccagaaa  22740
agttgctgtg atccaaaaag gagcaagtta aaggggaggaa tgaaacagga attcaggatg  22800
aaaaaatgag aaatctttcc aatggttgtt gttttgttta tgatgaatgc cacggatatc  22860
agacattctt atgcagaagt gagtttaaaa gatccaaagc atttccaccg ttttctgttt  22920
aaagagcagc aacaagaatc acacatgttc caacatgcag tttagagagg ctagaggcac  22980
agatatggac agacgtccct gctcctaaca gctctctaag gtctggtgga ggattcagac  23040
acatgacctg gcctggagga ttgagcttct ggattgtctg taagctaggc aatccactat  23100
ttagtcttta gtactgtaat agaggtctca gtaagtgtgt accttgtttg cctactttat  23160
atatttttat tttgtgcgat accaaatatt gtggaaggat ttcaggtagg aattttgagt  23220 gttgttttg catcaattta taaagatgac ggtctctgag ctttgcaggc agtatgtcta  23280
taccgtgttg attcatgtgc ctggctacag gtcaccacac actatacact cttgagtttg  23340
ctctggagaa atctcaatga gccacctgca acataacctg ctttgtggct gggttcctta  23400
aaatccaata tattctgaag gatgtgatca ataagcagat ggctcaagcc catacacatg  23460
ccaagaaatg aggcatctaa ttaacagtta gacaagggtg tgagggaatt gcagagggt  23520 gtggaggccc tgcctgggct gggagacctc gggatgggag aatcagggct ggttgtgtga  23580
cgtgtcgaca catagtggct gttggaagtg tgaacacagt cgggaccttc aggctgtgct  23640
cattagggct ttgcaaaatt cccaattatc tcttgacctg gccctaagca aggcccttt  23700 ccattgccct ggaaaaaaaa aatgagtgag tcaaaaagga cacctgattt gacacgctac  23760
atgggtttgg ttctgaagct aggctagtag aacacagaaa tgaggcattc ttgtgcaacc  23820
agtgatgact acaggaagga taagtaccag gagcatccgg tgtcacagag gcaagggcgg  23880 gcttttgag atggctgtat ggtgccccaa acaaaggcca gaaagagacg atttgtgaga  23940
agagaccaac gcgccccttg caagaattc ataagcagtg tttcagttaa actgcaaatc  24000
tcatggatgg tgtcaaaaga gtgaggactc cttccgtac acgtctcaca gctcaaacag  24060
gaacagaaag aggctttctc tctgtgtctt ggagaaccca ccactaagtg ctccctggtg  24120
tcagagaagg gaattgggct cagtgtgaca gctttccctg ctatatgtga aatacattat  24180
caatctgttg tcagcctgat gctccctagc tgactgtttt gttgttgcgc ttccagtgtt  24240
accctgggtt ggtccctgcg tgatgttct aatataaaat atgcagattg tgaaagagaa  24300
gacaatgctt cgagtctgat ctatcctaag atgaatgtgc taatgctccc aagacccata  24360
```

```
agacagagga ggtcaagaag gtgccttgtg gtaggcgatg catcttcaaa ttcgttgaca    24420
caggctcgtg aattcagatt agcacttgac cacaaataca catgttaaaa caaagtcaca    24480
ttaaacatct ctcttcctca atctcctttc ccagcttcct tgcagagaag aaatgcaaga    24540
aggtgagtga ataaaatcag aattatttgc ttttattct gaggacaaaa gacaactggt     24600
tggattccat gggcacacag tgatctaagg ttatagtaac caacaactat gactaagaaa    24660
gtgatagtca ttgtgatagt taattttaca tgtccatttg gctaggctat ggtgcccaat    24720
tgttttatca aatgctagct ggatgttgct gtgaaggtga ttaacattta aatccataag    24780
ctttgagtaa agttgattac cgtccataat gtgagtggcc ctcatccagt tagctgaagg    24840
acttacgaga atgattgagg tttctggaag aagaaattct gcctcaagac ttttaacata    24900
gagactctca gcctgcagat tttggactca agactgcaac atcatcttgt gcctgaaatt    24960
ccagtaggct gccttgccct acagattttg gacttgtcat catccccat aatgacatga     25020 gtcaattcct taacataaat ctctcctata tatcctactg gctctgtttt tctggataac    25080
cctgattaac acaatcattc tgtctattgt agatgatctg tcctccttga ccacactcat    25140
tggccaacac tagccttatt acctgcaaac atgagatagc atgatctatt gcccagaaaa    25200
gaggatagaa tagaggctat ttttttcctc ccatctccct gttcccctgt cctctatcct    25260
tatcttaatc tttccaacct actattatgc tccaagagtg ttacctactt ttattatttt    25320
ctgtcttcaa agttaaagag tgcctgaaag tatgcagata attcaaacaa aaaagcaaca    25380
cttccctgtg taattattcg ctcaactctt tgccttggtg taatttatgt gctcaacact    25440
tttccttgga atcttagcta aagaagactt ttctggggac tgggcgtggt ggctgaagcc    25500
tgtaatccca gcactttggg aggccgaggt gggcggatca cgaggtcagg agatcaagac    25560
catcctggct aacacggtga aaccccatct ctactaaaaa tacaaaaaaa ttagccaggt    25620
gtggtggcgg acacctgtag tcccagctat tcaggaggct gaggcaggag aatggcgtga    25680
acccaggagg cagaacttgc agtgagccaa gatcgcatca ttgcactcca gcctgggcga    25740
cagagcaaga ctctgtctca aaaaaaaaa aaaaagaac acttctggaa actgttttc       25800 ctggcagtcc ttggtcaagt tgctaattta atattttaga tggttttgac atggtttaga    25860
atgcaaaatt atcatctttt aatatgtatt tgtttgcaga gaacccatgg gccttagttc    25920
atttctgcac ccacagagag gtttaatctc atttaaatgc taaacatcgc agtggtcagg    25980
cattaggaac actgctagga aggctgcaac aaaacaagtg ttttccactta gtgttatttg    26040 ggggttacca tccacatcat acaggaaatg gagtgacaaa taccaatttg agaaaggaac    26100
acaatgaaac tacataattc ctcttgtagg ttagttgatc tgtaaccaag ccttaaaaat    26160
tgacattgac attgaaccac tgcctgtgaa gggagaatga gaaataacct caaatctgcc    26220
tctaaataaa ccatccatag cttaattcaa gagttgggat accagctctc tagcattcaa    26280
atggaattta ggtatttact aggcatactg tgggggattt ttaagttgaa tgggtaacat    26340
agagcattgg ggcaaaataa tagaatacgg ttgctggttt caatgacagc atgggtcttt    26400
tccaccaaga gactacagta caaaatttaa atcaggtaaa ctggtccaat gtagaaagca    26460
ggcagtcagg gaagcatagt ttaagggtgg cattgaaata gttttgccac ttcaatttgg    26520
tcactagctt ttgggatcag agtatagtgt caatgaagag agtcaaattc tgtaaaatat    26580
ttgaagagat ttattctgag ccaaatatga gtgaccatgg ctcatgacag ccctcaggag    26640
accctgaaga catgtaccca aggtagttgg ggcacagctt ggttttatac actttaggga    26700
gacacaagac atcaatcaaa tacatttaag atatacattg gttcgattca gaaaggtggt    26760
```

```
acaacctgaa gtggcagggg ggtggtggcg gggcagcttc caagttatag gtagatttaa    26820
acattttctg attggcaatt ggttgaaaga cttactatca atagaaagaa atgtctgagt    26880
tatgataaaa tgttgctgag accaaagttt tatcatgcag atgaagcctc caggtagcag    26940
gctctagaga gaatagattg taaatatttc ttatcagact taaggtctgt gttgatgtta    27000
catgctggtc agctcttcct gaattccaaa agggaggtgg tataacgagg tatgtctaac    27060
ctctctaaga gctccctctt agaaacaaac agacaaaaca cacaacaaaa accacacttg    27120
taaacccatc gtcccatctc tccacagctt gacttctttt cataatccag atttggctta    27180
gggatccaag agtcttgaaa atatttccca tgcatttatt ctgaaatttg ccaagggtaa    27240
tttgactcct cccttttgggt tttgtgttta tggtgcctga gatttcaaat ttgacattgt    27300
taattttgtt ccccacctcc aatcagcctt gcccacctca acaaatgtcc acttcattct    27360
ttcggtgggg gtcactctgg actttgttct ttctctcaaa ttgtcagtca acaactctgt    27420
cggccctgcc tttgaaataa attcatctag gatcctgccc ctcttcacca ctgccaccac    27480
catgctggct aaagccactg ttatttctcg taggttagga caacaccttc tgtctggtgt    27540
tgcctctact gtctagtctc cacacatagc cagaatactc ttaaaacata catcagatac    27600
catcatttct tagcttgcca ttctctaatg atgtcccaca attcttagag taacatctca    27660
aaatgtgacc atgccctgtg tattagtcgt cctcatcctc ctcctcctcc tccccttctt    27720
cttcttcttc ttctttatca tcattaaact ttaagttctg ggatagatgt gcagaatatg    27780
caggtttatt acataggtat acatgtgcca tgtggttttc tgcacccgtc aacccattgt    27840
ctaggatttg agtgctgcat gcattaggta tttgtcctaa tgctctccct cccctttgtcc    27900 cccatcccct gagaggcccc agtgtgtgat gttcccttct ctgtgtccat gtgttctcat    27960
tgttcaactc tcacttatga gtgaaaacat gtggtgtttg gttttctgtt cctgtgttag    28020
tttgctgaga ataatggttt ccagattcat ccatgtccct gcaaaggaca tgaattcatt    28080
cttttttatg gctgcatagt attccatggt gtatatgtgc catattttct atatccagtc    28140
tatcattgat gggcatttgg gttggttcca agcctttgcg attgtgaata gcactgcaat    28200
aaacatacat gtgcatgtat cttacagta gaatgattta tcatcctttg ggtgtttata    28260
cccagtaatg ggattgttgg gtcaaatggt atttctggtt ctagatcttg aggaatcgcc    28320
acactgtctt ccaaatggc tgaactaatt tacactgaca cagtgtaaaa gctttcctat    28380
ttctcgacat cctctccagc atctgttgtt tcctgacttt ttaatatttg ccattctaac    28440
tggcatgaga tggtatctca ctgcggtttt gatttgcatt tctctaacga ccagtgatga    28500
gctttttttt tcatgtttgt aggctgcata aatgccttct ttagagaagt gtctgttcat    28560
atccttcacc cacttttga tggggttgtt ttttttcttgt aaatttgttt aagttccttg    28620
tagattctgg atgttagacc tttgtcagat ggagagattg caaaaaattt ctcccattct    28680
gtaggttgcc tgttcactct gatgatagtt tcttttacta tgcagaagct ccttagttta    28740
agtagatccc atctgtcaat tttggctttt gttgccattg cttttggtgt ttttgtcatg    28800
aagtctttgc ccatgcctat gtcctgaggg gtattgccta ggttttcttc tagggttttt    28860
atggttttag gttttatgtt taaatcttta ggcaatcttg tgttaatttt tgtataaggt    28920
gtaaggaagg ggtccagttt cagttttctg catatgctta gccagtgtcc ccagcaccac    28980
ttattaaata gggaatcctc tccccattgc ttatttttgt caggtttgtt gaagatcaga    29040
tggttgtaga tgtgtggtgt tatttctgtg gcctttgttc tgttccattg gtctatatat    29100
```

```
ctgttttggt accagtacca tgctgttttg gttgctgtag ccttgtagta tagtttgaag    29160
ccagggagtg tgatgcctcc agctttgttc tttttgctta ggattgtcat ggctatacag    29220
gctcttttct ggttccacat aaaatttaaa gtagtttttt ctagttctgt gaagaaaatc    29280
aatggtagct tgatgggaat agcactgaat ctataaatta cttgggcag tatggccatt     29340 ttcacaatat cgattcttcc tatccatgag gatggaatgt ttttccattt gtttgtgtcc    29400
tctcttattt ccttgagcag tggttttgtag ttcttgaaga ggttcttcgc gtcccttgta   29460
agttgtattc ctaggtattt tatttccttt gtagcaattg tgaatgagag ttcactcatg    29520
atttggctct cttttcatct gttattggtg tttaggaatg cttgtgggtt ttgcacattg    29580
attttgtatc ctgagacttt gctgaaggtt cttatcagct taaggagatt ttgggcagag    29640
atgatggggt tttctaaata tataatcaca tcatctggaa atagacaatt tgacttcccc    29700
tcttcctatc tgaatactct ttctttctct tgcctgattg ccctagccag aacttccaat    29760
actatgttga ataggagtgg tgagagaggg catccttgtc ttgtgccagt tttcaaaggg    29820
aatgcttcca gcttttgccc attcagtatg atattggctg tgggtttgtc ataaataggc    29880
ctcattattt tgacatatgt tccataaatc cctagtttat tgagtgtttt tagcatgaag    29940
ggatgttgaa ttttattgaa ggcctttcct gcatctattg agataatcat gtggtttttg    30000
tcattggttc tgtttatgtg atggattatg tttattgatt tgcatatgtt tgaaccagct    30060
ttgtatccca gggatgaagc cgacttgatc gtggtggata agccttttga tgtgctcttg    30120
gattcgcttt gccagtattt tattgaggat tttcgcagcg atgttcatca gggatattgg    30180
cttgaaattt tattttttg ttgtgtctct gctaggtttt ggtatcagga tgatgctggc     30240
cttataaaat tagggaggat tccctctttt cctattgttt ggagtagctt caggaggaat    30300
ggaaccaact cctctttgta cctctggtag aatttggctg tgaatccatc tggtcctggg    30360
ctttttttgg ttcgtaggct attaattact gcctcaattt cagaacttgt tattagtgta    30420 tatgggatt caacttcttc ctgggttagt cttgggaggg tgtatgtatc caagaattta    30480
tccatttctt ctacattttc tagtttactt gcatagaggt tttcatagca gtctctgatg    30540
gtagttttta tttctgtggg atcagtggtg atattcccct tatcattttt ttattgtgtc    30600
tatttgattc ttctctcttt tcttctttat tagtctggct agcagtctat ctattttgtt    30660
aatcttttca aaaaccagc tcctggattc attgattttt tgaagggttt ttcatgtctc     30720
tgtctccttc agttctgctg ttagtgtgtt ggttttagat ctttcctgct ttctgatgtg    30780
ggcattatag tgctataaat ttccctctta acactgcttt agctgtgtcc cacagattct    30840
ggcatgttgt gtctttattc tcattggttt caaagaactt atttatttct gcctcaattt    30900
tgttatttac ccagtagtca ttcaggagca ggttgttcag tttccatgta gttgtgtggt    30960
tttgaatgag tttcttaatc ctgagttcta atttgattgc actatggtct gagagactgt    31020
ttgttacgat ttccattctt ttgcaattgc tgaggagtgt tttactttca attacgtggt    31080 caatttaga ataactgcta cgtggtgaag agaagaatg atattctatt gatttggggt      31140
agagagttct gtagatgtct attaggtctg cttggtccag agctgagttt aagtcctgaa    31200
tatccttgtt aattttctgt ctcattgttc tgcctaatac tgacagtggg gtgttaaagt    31260
ctcctactat tattgtgttg gagactaagt ctctttgtag gtctctaaga acttgcttta    31320
tgaatctggg tgctcccgta ctgggtacat atatatttag gaaagttagc tcttcttgtt    31380
gcattgatcc ctttaccatt atgtaatgcc cttcttgtc ttttttcat ctttgttggt      31440 ttaaagtctg ttttatcaga gactaggatt gcaacacctg ctgtttttat ttatttattt    31500
```

```
atttatttat ttttattttt ttagctttcc atttgcttgg taactattcc tccatctctt   31560
tattttgagc gtatgtgtgt ctttgcatgt gagttgggtc tcctaaatac agcacaccaa   31620
tgggtcttga ctctatccaa tttgccagtc tgtgtctttt aattggggca tttagtccat   31680
ttacttaaag gtaatatcat tatgtgtgaa tttgttcctg tcatcatgac gctagctgtt   31740
tattttgcac attagttgat gcagtttctt catagtgtca atggtctttta catttcggtt   31800 tgttttgca gtggctggta ccagtttttt ctttccatgt ttagtgcttc cttcaggaac   31860
tcttgtaagg caggcctggt gttgacaaaa tccctcagca tttgcttgtc tataaaggat   31920
ttttttctcc ttaacttatg aagcttagtt tggctggata taaaattatg ggtcgaaaat   31980
tcttttcttt aagaatgttg aatattggcc cccactctct tctggcttgt agggtttctg   32040
cagagagatc cactgttagt ctaatgggct tccctttgta ggtaacctga cctttctctc   32100
tggctgtgct taacactttt tccttgtttt caaccttgga aaatctgatg attatgtgtc   32160
ttggggttgc tcttctcgag gagtatcttt tggtgttct ctatatttcc tgaatttgaa   32220
tgttgacctg tcttgttagg ctgtggaagt tctcttggaa aatatcctga agtatgtttc   32280
ttggaaaata tcctgaagta tgtttggaaa atatcctgaa gtatactttc caacttggtt   32340
ccgttctccc catcactttc aggtacacta atcaatcata ggtcttttca catagtccca   32400
tatttcttgg aggctttatt tgttccttt cattctttttt tctctaatct tgtcttcacg   32460
ctttatttca ttaagctgat cttcaatctc tgatatcctt tcttctgctt gatcgatttg   32520
gctattgata cttgtgtatg ccttacgaag ttctcatgct gtgttttca gctccatcag   32580 atcatttatg ttcttctcta aactgcttat tctagttagc aattcctcta accttttatc   32640
aaggttctta gcttccttgc attggttag aacatgctcc tttagctcag tggagtttga   32700
tattacccac cttctgaagc ctacttctgt cgatttgtca aactcattct ccatccagtt   32760 ttgtgcccctt gctggagagg agttgcaatc atttggagga gaagaggcat tctgtttttt   32820
ggaattttca acatttttgc actgtttttt cctcatcttc gtggatttat ctacctttga   32880
tttttgatac taatgacctt tgggtggggt ttttctgtgg gcatcttttt tgttgatgtt   32940
gatgttattg ctttctgttt gttagttttc cttctaacag tcaggcccct cttctgcagg   33000
tctgctggag tttgctggag gtccactcca gaccctgttt gcctgggtat caccagtgga   33060
ggctgcagaa cagcaaatat tgctgcctgc tccttccttt agtagcttcg tcccagagtg   33120
gcatctgcca gaagtcagct ggagctcttc tgtatgaggt gtctgttgaa ccctgctgga   33180
aggtgtctcc ctgtcaggag gcatgagggt cagggacccc cttaaggaga cagtctgtct   33240
cttagcagag cttggacact gtgctggag atccgctgct ctcttcagag ctgacaggca   33300
gaacgtttaa gtctgctgaa gctggatcca cagccgcccc ttcccccagg tgctctgtcc   33360
caggcagatg ggaattttac ctatcagccc ctggctgggg ctgctgcctt tctttcagag   33420
atgccctgcc cagagaggag gaatctggag aggcagtctg gccccaggta ctttgccatg   33480
ctgcggtgag ttctgcagtc agagttaaca ctgtaagggg aaaagcacct actcaagcct   33540
cagtaatggt ggacgcccct cccccaacaa gctcaattgt cccaggttga cttcatactg   33600
ctgtgctggc agcgagaatt tcaagccagt ggattttagc ttgctggact ttgtgggaat   33660
gggacccgct gtgcgagaag acttggcttc ctggcttcag ccccctttcc aggggagtga   33720
gtggttctgt ctcactgggg ttccaggcac tgctggtgta tgaaaaaaaa ctcctgcagc   33780
tgtttatctg cccagagagt tgcctagttt tgtgcttgaa acccagggcc ctggtagtgt   33840
```

```
aggcacacga gggaatctcc tggtctgtgg gtggcaaaaa ccatggaaaa agcatagtat    33900
ctgggctgga tagcacagtc cctcacagta gagtccctca gggcttccct tggctaggag    33960
agggaggtcc atgacccctt gcacttcctg ggtgaggcga taccccaccc tgcttctgtt    34020
cccctccat gggctgcacc cactgtctaa ccagtcccag tgagataaac cgggcacctc     34080
agttggaaat gcaataatca cccaccttct gcgttggtct tgctgggagc tgcagactga    34140
agctgttcct attcagccat cttgccaact ctcttgtatt agttttctat tgctgccata    34200
acgaatagtc tccatcttag cagctaaaaa caacacccat ttatcaactc acagttctgc    34260
aggtcagagt ctcgtaggct tggctagttt ctctgtcctg agtctcatca gattgacagc    34320
aagggctga caaggctgta ttcccttttg aaaattttgg agatggatgt gtgtctttgt     34380
tcattcaggt tattcactga attcagttcc tgtggttgta gcaatgagat ctccgtttcc    34440
tttctggcgg tcagcccagg gtagccttgg ctcctagatg ctgcttgcat ccctcaatct    34500
ttccaggtgg cccctccacc cacagcaggt agggtccagg tccctctctt gctttagatc    34560
tttcctcctt actcttctca ctccagccac atttctctca ctccagccag agacatttct    34620
ctaattttag atgggttcca ctccctggtt taaggtctgc tatcttaatt gcatctgcca    34680
aatctcatca tagcagtacc caggttaata tttgattgaa ttactgggag ataggaatag    34740
tgagggacta ccacagccta ggaagtcttg aatgatatga ttcctgtgac ttctctgact    34800
tcatgtcatc cctcttttcc ttttaatatc tagactccaa gtcagtatgg cctccttgct    34860
gttttctcca attgaccaaa cctatatcca cttgagggcc ttgacacctc acatttcctc    34920
tgccagaaca cccttgcccg aggcctttcc atggcccact ctctcactaa gttggatgag    34980
tcctctggga agcagactcc aaggcagtat taggagagct caagatttat tgggggtaag    35040
gcctgtgaaa gataaaggag agaagggaca ggagtgggaa ggctgggcct tcagaccaca    35100
gtgcaggtct gacatccttg cagggatagg aggggatagg aggattggat gaagagcctc    35160
agatttccat gcatactgca ctgagaaagt gtcagccagc ccagcaggga gcttttgcca    35220
cagagattgc ctgtggaagg gttccacgct gcccgggaaa tggcaagcct ttgtatcatt    35280
gtgctccgtc attggctgag gattatccag gaagcatgtg acctccactc aaaagctgag    35340
ggagaaacaa ccaaatgtcc atcaacagat gagtggatgg acaaaacgta gtatgcacat    35400
tcagtggaat attatccagc catgaaaagg aatgaagtat tgacacacac taccacatgg    35460
atgaacattg aaaacactgt gctcagtgaa ataaaacagt cacaaaagga caaatattgt    35520
atgcttctac ttatggtaaa tatttagaac aggtaaatcc atagacaaa aatatagatt      35580
agaaggtcca aggcttgcag aaggaagaaa tgaggagtta tcatttaacg ggtacagttt    35640
ctgtttgagg tgttaacaat ttttgaaact ggatagtggt ggtgatagtt gcacagaatt    35700
gtgaatataa ttaacaccac tttaaaatct taaaaatggt tgaagtggca aatttttatgc   35760
taaatacatt ttactacagt aaaaaacaaa acaaaacaaa aaaacagacc gaggcagatc    35820
ctgaaagcac cagcagctag aagctgtcag caaatagcac cttttgtggg aagcacatct    35880
ccatggctgc catgctcact gcctcgggtc tctgccgaaa tggcaactga gcagtgagtc    35940
ccttaatgac taaattacat ccaagaggaa ggcctatcct tctcagtcaa gttaattttt    36000
ctccattaca cttaaagcct tctgacttat atatttacct gtttattttc tgcttcccca    36060
atagaccata aacaccatga gatcagagca tccatctgta gactcacaga gcaagaagcg    36120
tgactgcccc aatcttgaat ggatgagtaa g                                    36151
```

-continued

```
<210> SEQ ID NO 59
<211> LENGTH: 2861
<212> TYPE: DNA
<213> ORGANISM: Homo sapiens

<400> SEQUENCE: 59
ctcgcaagac ctggttgttt aaaagtgggc ggcaccttcc ccttcgctct tcctcctgct      60
cctgccctga tgtgtctgga tggtgacaga tgggaatctt ctccagtgac cagaatccat     120
gccttacctt gggagcccaa gctgacttct caagctctgg ggatgcctca gtgatctctg     180
atgtggaatt agtggaggct ggccgttgct cacctctaca cagcctgctg gtcgttagcg     240
agcaggagtt ctgatgttcc tctcatcttg gatgtctttc ctaggagaat atttctcacg     300
tgtttgacag aaaacattat ctgtccatca tttccatgga ttcctgggtc tcacgggcag     360
aaggacaagg cagatatgag gcggatctgg taaaaccata acaccatgag atcagagca     420 tccatctgta gactcacaga gcaagaagcg tgactgcccc aatcttgaat ggatgagtaa     480
gatgaaaatc aatttataaa catcttgtga caagctggaa ttcagttata gatcaattac     540
agattgctca ctggacaatc aaggacatta ttagaaaacg gtttccacca ctagaaattc     600
atctacattg acatccacct aaatatccag aaggtcatcc ccactttcgt cgctctccac     660
agtcagctgc cgggtccacc acttcttaac ttcagaaccg caggaagccg cgtcagtcat     720
ggggttcatt ttgcacacga cagatttcat ggttgtcctt cctccaaacc gaggaaccta     780
gatcttctct gatctctgaa aaataagttc ctggatatga aaggggatac tttccttggt     840
ggtagtccca gtgaagaccc actgaacatc gtcagcctca aaatgtaagc tgtgctgtca     900
tctgctttgt ggaacacata tgctacacat cttctccttt caattgggct gaagttgggg     960
cacagttaaa gagcattata aagctcctgc tttagcatga acttagttat ctatagaaaa    1020
aaacatgtac aaggacactg ggctgtgggg agcattgctc tccctccatt cctgagtgct    1080
cttaatggga ttatcctggc tttccaaaac cctatagaga agaagctcat agaagaaaat    1140
tctcttactg aatcagtaaa atatggaaaa taatgggact gtttattaaa ggattgaatg    1200
agagaacaca gtaatgcac ttagaagagt gactggcata cagtgagtac tacgtgctgg    1260
cttctcaacc atgatagcct gaaatgtacc cggaaaatgg gggctaatgt aagtcatatt    1320
tagagaagtt attttggggg acaatgtttt tgacaagact acattttca ttatgttgct     1380 gtctgtaaac aactgtagat gcagacttgc attttgaaag gcaagaccca aaacacacaa    1440
acagagtaaa tacctttaaa atgcctcgat cgctggagaa atgcctggat ggacctacct    1500
gagggcagac gccactgccc aaatttcctc tggggtttcc ctgcgtcggc tgcatcttgc    1560
cgacttcctc ctcgatccga cagcgtgggg ctcaggagct gctgctggct gcttgtctgc    1620
atgggaggag aagcacacag ttaccgtctt tttaaccctg cgctctcctc ctttactat    1680 aagaaaggaa aacacatggc aggaggacaa gtgggaagaa caacatggac tcagagtgtc    1740
cacaatgggg aaaagtgaaa atgggtataa agggtcacag aagaaaaaga gccaccactg    1800
cacgccctgc tgaaggagac accactcttc ctgggacatc ttgtcctggg taaccccac    1860 tgcttcgttc ccctccatgc ctgagaatgt cattgtttcc cttcatatct tcgctggcaa    1920 accaggggt aaggaagggg aactgcagga aggaaggtgg ggcagtgggg acgggctggg    1980 cggggggcagt ctactgtcac cagcctggag atccacactt agagcttcag ggaaagagtt    2040
ctctgcaggc aaagctgtat gatgggccct ggtggaggat ggagctgata acaatctaag    2100
ctacagtgaa agaaagagag atgccaagac ttcccacaca tttcacctgt tctcaggttc    2160
```

```
acctgtcacc tctcccttcc ctaacaaaag ccttggtctt cacatctctt tagtatcctt    2220
tttttttttt ttttgtcacc tctttctttc ttaggctttt tcatctaaaa acagagggct    2280
ctgaaatcat cactttcccc aacctcatta gccctgtctc actgtctgtc ctgacttcag    2340
cctgcctccc tctcccatgc gagacattgc caaccatctt cagggtgacc agtggcaagg    2400
ccactgcaga tgcctcccct tgcccctggg ttgactaact ccgcagaagt ccctgcagtc    2460
ggtggcagat gatttctaaa ggctggggag cccaaaacat gagatctact gaaaactgag    2520
ctatggcacc agtgggcctc ctggagcacc ctgctgggcc gtggagcctt aggcttccaa    2580
aggtactctg gccctggct gcgttgctgc acaccatgga gcctggtgct gctgggggct     2640
ctgcacagag cacgggatca gctccacgtt gttaacctca aatcgtaatt gctgcctcat    2700
aaaggggcag gtcctcccag ccagctgctt ctcacagcac aggactctcc aggacgctga    2760
taactccttg tactttttta tatagacaca tacatagagt ttgaaaatga aaatatgctg    2820
tgacttaata aatagaaact cctcaaaaaa aaaaaaaaa a                        2861
```

ENGINEERED PRODUCER CELL LINES AND METHODS OF MAKING AND USING THE SAME

CROSS-REFERENCE TO RELATED APPLICATIONS

This application claims the benefit of and priority to U.S. Provisional Patent Application No. 62/833,548, filed Apr. 12, 2019; to U.S. Provisional Patent Application No. 62/839,207, filed Apr. 26, 2019; and to U.S. Provisional Patent Application No. 62/979,483, filed Feb. 21, 2020, the disclosures of which are hereby incorporated by reference in their entireties for all purposes.

SEQUENCE LISTING

The instant application contains a Sequence Listing which has been submitted electronically in ASCII format and is hereby incorporated by reference in its entirety. Said ASCII copy, created on Apr. 9, 2020, is named ULP-005US_SL.txt and is 113 kb bytes in size.

FIELD OF THE DISCLOSURE

This application relates generally to engineered producer and/or packaging cell lines and methods of generating the engineered producer and/or packaging cell lines for increasing recombinant adeno-associated virus (rAAV) titer.

BACKGROUND rAAV-based vectors are one of the most promising vehicles for human gene therapy. rAAV vectors are under consideration for a wide variety of gene therapy applications. In particular, rAAV vectors can deliver therapeutic genes to dividing and nondividing cells, and these genes can persist for extended periods without integrating into the genome of the targeted cell. Although systems for producing rAAV have evolved over the last two decades, several issues remain to be solved. One limitation of rAAV production systems is the low titer yield of rAAV particles. Pharmaceutical development of rAAV-based gene products at preclinical stage require large amounts of rAAV vectors for studies in larger species to enable complete toxicology and biodistribution studies that are helpful in predicting dosages in humans. Furthermore, because current rAAV production systems result in low titer yields, manufacturing sufficient levels of rAAV for use in human trials and commercial applications is challenging. Researchers have explored numerous ways to generate adequately high titers of rAAV particles, but there is still a great need for addressing this issue. In particular, there is a need for efficient cell lines that are able to produce high quality rAAV with high titer yields. Production of high titer rAAV by the engineered cell lines described herein expedites the application of this vector system for gene therapy use in vivo.

SUMMARY

The present disclosure addresses the need for obtaining improved rAAV titers for gene therapy applications by providing rAAV packaging and/or producer cell lines comprising cells in which one or more genes and/or proteins have been modified. Also described herein are methods of identifying one or more genes and/or proteins that are relevant to the production of rAAV, and methods of generating engineered rAAV packaging and/or producer cell lines.

Described herein are compositions and methods of generating rAAV packaging and/or producer cell lines comprising cells that can produce a higher titer of rAAV compared to control parental cells. More specifically, provided herein are rAAV packaging and/or producer cell lines comprising cells in which expression of one or more genes and/or proteins is modulated resulting in a higher rAAV titer compared to control parental cells. In one aspect, the present disclosure provides rAAV packaging and/or producer cell lines comprising cells in which expression of one or more genes and/or proteins is reduced compared to control parental cells. For example, expression of ATP5EP2 (ATP Synthase F1 Subunit Epsilon Pseudogene 2), LINC00319 (Long Intergenic Non-Protein Coding RNA 319), CYP3A7 (Cytochrome P450 Family 3 Subfamily A Member 7), ABCA10 (ATP Binding Cassette Subfamily A Member 10), NOG (Noggin), RGMA (Repulsive Guidance Molecule BMP Co-Receptor A), SPANXN3 (SPANX Family Member N3), PGA5 (Pepsinogen A5), MYRIP (Myosin VIA And Rab Interacting Protein), KCNN2 (Potassium Calcium-Activated Channel Subfamily N Member 2), and/or NALCN-AS1 (NALCN Antisense RNA 1) is reduced compared to control parental cells.

In some embodiments, the present disclosure provides rAAV packaging and/or producer cell lines comprising cells in which expression of KCNN2, LINC00319, RGMA, and SPANXN3 is reduced compared to control parental cells.

In certain embodiments, the present disclosure provides a rAAV packaging and/or producer cell line comprising cells which have been engineered to reduce the expression and/or activity of a gene product expressed from ATP5EP2, LINC00319, CYP3A7, ABCA10, NOG, RGMA, SPANXN3, PGA5, MYRIP, KCNN2, and/or NALCN-AS1 as compared to corresponding unmodified parental cells. In certain embodiments, the present disclosure provides a rAAV packaging and/or producer cell line that exhibits reduced expression and/or activity of a polypeptide or a polyribonucleotide expressed from at least one of ATP5EP2, LINC00319, CYP3A7, ABCA10, NOG, RGMA, SPANXN3, PGA5, MYRIP, KCNN2, and NALCN-AS1 as compared to a corresponding parental cell line.

In one aspect, the present disclosure provides a rAAV packaging and/or producer cell line in which expression of one or more genes is reduced using a nuclease, a double stranded RNA (dsRNA), a small interfering RNA (siRNA), a small hairpin RNA (shRNA), a microRNA (miRNA), or an antisense RNA oligonucleotide (ASO).

In certain embodiments, the expression of one or more genes is reduced with an siRNA comprising a nucleotide sequence selected from any one of sequences SEQ ID NOs: 1-11. For example, in some embodiments, expression of ATP5EP2 is reduced, and the siRNA comprises the nucleotide sequence of SEQ ID NO: 1 in the sense strand and the nucleotide sequence of SEQ ID NO: 32 in the anti-sense strand. In some embodiments, expression of LINC00319 is reduced, and the siRNA comprises the nucleotide sequence of SEQ ID NO: 2 in the sense strand and the nucleotide sequence of SEQ ID NO: 33 in the anti-sense strand. In some embodiments, expression of CYP3A7 is reduced, and the siRNA comprises the nucleotide sequence of SEQ ID NO: 3 in the sense strand and the nucleotide sequence of SEQ ID NO: 34 in the anti-sense strand. In some embodiments, expression of NOG is reduced, and the siRNA comprises the nucleotide sequence of SEQ ID NO: 4 in the sense strand and the nucleotide sequence of SEQ ID NO: 35 in the anti-sense strand. In some embodiments, expression of SPANXN3 is reduced, and the siRNA comprises the nucleotide sequence of SEQ ID NO: 5 in the sense strand and the nucleotide sequence of SEQ ID NO: 36 in the anti-sense strand. In some embodiments, expression of MYRIP is reduced, and the siRNA comprises the nucleotide sequence of SEQ ID NO: 6 in the sense strand and the nucleotide sequence of SEQ ID NO: 37 in the anti-sense strand. In some embodiments, expression of KCNN2 is reduced, and the siRNA comprises the nucleotide sequence of SEQ ID NO: 7 in the sense strand and the nucleotide sequence of SEQ ID NO: 38 in the anti-sense strand. In some embodiments, expression of NALCN-AS1 is reduced, and the siRNA comprises the nucleotide sequence of SEQ ID NO: 8 in the sense strand and the nucleotide sequence of SEQ ID NO: 39 in the anti-sense strand. In some embodiments, expression of RGMA is reduced, and the siRNA comprises the nucleotide sequence of SEQ ID NO: 9 in the sense strand and the nucleotide sequence of SEQ ID NO: 40 in the anti-sense strand. In some embodiments, expression of PGA5 is reduced, and the siRNA comprises the sequence of SEQ ID NO: 10 in the sense strand and the sequence of SEQ ID NO: 41 in the anti-sense strand. In some embodiments, expression of ABCA10 is reduced, and the siRNA comprises the sequence of SEQ ID NO: 11 in the sense strand and the sequence of SEQ ID NO: 42 in the anti-sense strand.

In certain embodiments, the nuclease used to reduce expression of one or more genes is selected from the group consisting of a Zinc Finger nuclease (ZFN), a meganuclease, a transcription activator-like effector nuclease (TALEN), or a clustered regularly interspaced short palindromic repeats (CRISPR) associated protein.

In certain embodiments, the expression of one or more genes is reduced using CRISPR genome editing. In some embodiments, a guide RNA pair is used to target a gene to reduce and/or eliminate expression of that gene. In certain embodiments, the expression of one or more genes is reduced using a guide RNA pair, wherein each guide RNA: (a) comprises a sequence selected from the nucleotide sequences of SEQ ID NOs: 12-15 and/or (b) targets a target DNA sequence selected from any one of the nucleotide sequences of SEQ ID NO: 16-31. For example, in some embodiments, the gRNA pair is used to target KCNN2 and comprises a first gRNA molecule comprising the sequence of SEQ ID NO: 12 and a second gRNA molecule comprising the sequence of SEQ ID NO: 13. In some embodiments, the gRNA pair is used to target KCNN2 and comprises a first gRNA molecule comprising the sequence of SEQ ID NO: 14 and a second gRNA molecule comprising the sequence of SEQ ID NO: 15. In some embodiments, each gRNA molecule is a 2'O-methyl analog comprising 3' phosphorothioate internucleotide linkages in the terminal three nucleotides on either or both its 5' and 3' ends.

In certain embodiments, one guide RNA pair is used to reduce expression of one gene. In certain other embodiments, multiple guide RNA pairs are used to reduce expression of one or more genes. In certain embodiments, the gene expression of one or more genes and/or the activity of one or more genes and/or proteins is reduced and/or eliminated in a rAAV packaging and/or producer cell line compared to a control parental cell line. In certain embodiments, the gene expression and/or activity is eliminated in the rAAV packaging and/or producer cells compared to control parental cells.

In some embodiments described herein, the rAAV packaging and/or producer cell line is a eukaryotic cell line. In certain embodiments, the rAAV packaging and/or producer cell line is a human cell line. In certain embodiments, the rAAV packaging and/or producer cell line is an insect cell line. In certain embodiments, the rAAV packaging and/or producer cell line is a HeLa cell line. In certain other embodiments, the rAAV packaging and/or producer cell line is a human embryonic kidney (HEK) 293 cell line.

In some embodiments described herein, the rAAV packaging and/or producer cell line of the present disclosure produces a higher rAAV titer than a control parental cell line. In certain embodiments, the titer of rAAV produced from cells of the rAAV producer cell line of the present disclosure is increased about 1.5 to about 7 fold compared to the titer of rAAV produced from a cell line comprising the control parental cells. Also described herein are lysate of the engineered cell lines. In certain embodiments, higher titer rAAV is harvested from a lysate. Also described herein are cell culture supernatants from engineered cell lines. In certain embodiments, higher titer rAAV is harvested from a cell culture supernatant.

Also described herein is a method of generating a producer cell line where the method includes delivering a rAAV vector to cells of a packaging cell line in which the expression of ATP5EP2, LINC00319, CYP3A7, ABCA10, NOG, RGMA, SPANXN3, PGA5, MYRIP, KCNN2, and/or NALCN-AS1 is reduced compared to control parental cells. In certain embodiments, the present disclosure provides a method of generating a producer cell line, where the method includes delivering a rAAV vector to cells of a packaging cell line in which the expression of KCNN2, LINC00319, RGMA, and SPANXN3 is reduced compared to control parental cell.

Also described herein is a method of producing rAAV by infecting the cells of a producer cell line, generated by a packaging cell line, with a helper virus, wherein the expression of ATP5EP2, LINC00319, CYP3A7, ABCA10, NOG, RGMA, SPANXN3, PGA5, MYRIP, KCNN2, and/or NALCN-AS1 is reduced in the packaging cell line compared to control parental cells. In certain embodiments, the expression of KCNN2, LINC00319, RGMA, and SPANXN3 is reduced in the packaging cell line compared to control parental cells.

In one aspect, the present disclosure provides a method of producing rAAV, by infecting the cells of a producer cell line with a helper virus, wherein the expression of ATP5EP2, LINC00319, CYP3A7, ABCA10, NOG, RGMA, SPANXN3, PGA5, MYRIP, KCNN2, and/or NALCN-AS1 is reduced in the producer cell line compared to control parental cells. In certain embodiments, the present disclosure provides a method of producing rAAV, by infecting the cells of a producer cell line with a helper virus, wherein the expression of KCNN2, LINC00319, RGMA, and SPANXN3 is reduced in the producer cell line compared to control parental cells.

Also described herein is a method of harvesting rAAV from a producer cell line in which the expression of ATP5EP2, LINC00319, CYP3A7, ABCA10, NOG, RGMA, SPANXN3, PGA5, MYRIP, KCNN2, and/or NALCN-AS1 is reduced compared to control parental cell line. Also described is a method of harvesting rAAV from a producer cell line in which the expression of KCNN2, LINC00319, RGMA, and SPANXN3 is reduced compared to control parental cell line. In certain embodiments, the production of rAAV from a producer cell line of the present disclosure is enhanced compared to a control parental cell line.

Also described herein is a method of identifying one or more genes relevant to the production of rAAV, where the method includes i.) adding one or more supplements that increase the rAAV titer in a cell line; ii.) measuring the global gene expression across the transcriptome in supplemented and non-supplemented cell lines; iii.) obtaining a list of genes that are differentially expressed between supplemented and non-supplemented cell lines; and iv.) identifying one or more genes that are relevant to the production of rAAV. In some embodiments, the one or more identified gene(s) is responsible for reducing the production of rAAV.

Also described herein is a method of producing a rAAV packaging and/or producer cell line to promote increased production of rAAV. In some embodiments, rAAV production is increased by modulating the expression of one or more genes and/or proteins identified from a list of genes that are differentially expressed between supplemented and non-supplemented rAAV producer cell lines. In certain embodiments, rAAV titer is increased by modulating the expression of one or more genes and/or proteins identified from a list of genes that are differentially expressed between supplemented and non-supplemented rAAV producer cell line. In some embodiments, the modulation of one or more genes and/or proteins increases rAAV titer at least 1.5 fold compared to rAAV titer of a cell line without the modulation. In certain embodiments, modulating the expression is reduction of expression of one or more genes. In certain embodiments, modulating the expression comprises reduction of expression of one or more proteins. In certain embodiments, modulating the expression is elimination of expression of one or more genes. In certain embodiments, modulating the expression comprises elimination of expression of one or more proteins.

In some embodiments, the rAAV packaging and/or producer cell line is a eukaryotic cell line. In certain embodiments, the cell line is a human cell line. In certain embodiments, the cell line is an insect cell line. In certain embodiments, the cell line is a HeLa cell line. In certain embodiments, the cell line is a human embryonic kidney (HEK) 293 cell line.

Also described herein is a recombinant adeno-associated virus (rAAV) packaging and/or producer cell line comprising cells which have been engineered to reduce the expression and/or activity of a gene product expressed from ATP5EP2, LINC00319, CYP3A7, ABCA10, NOG, RGMA, SPANXN3, PGA5, MYRIP, KCNN2, and/or NALCN-AS1 as compared to corresponding unmodified parental cells.

In some embodiments, the expression and/or activity of a gene product expressed from ATP5EP2, LINC00319, CYP3A7, ABCA10, NOG, RGMA, SPANXN3, PGA5, MYRIP, KCNN2, and/or NALCN-AS1 is reduced indefinitely or permanently.

In some embodiments, the cell line has been engineered to comprise a gene disruption or a partial or complete gene deletion in at least one of ATP5EP2, LINC00319, CYP3A7, ABCA10, NOG, RGMA, SPANXN3, PGA5, MYRIP, KCNN2, and/or NALCN-AS1.

In some embodiments, the cell line has been engineered to comprise a gene disruption in at least one of ATP5EP2, LINC00319, CYP3A7, ABCA10, NOG, RGMA, SPANXN3, PGA5, MYRIP, KCNN2, and/or NALCN-AS1.

In some embodiments, the cell line has been engineered to comprise a gene disruption in at least two genes selected from ATP5EP2, LINC00319, CYP3A7, ABCA10, NOG, RGMA, SPANXN3, PGA5, MYRIP, KCNN2, and NALCN-AS1.

In some embodiments, the cell line has been engineered to comprise a partial or complete gene deletion in at least one of ATP5EP2, LINC00319, CYP3A7, ABCA10, NOG, RGMA, SPANXN3, PGA5, MYRIP, KCNN2, and/or NALCN-AS1.

In some embodiments, the cell line has been engineered to comprise a partial or complete gene deletion in at least two genes selected from ATP5EP2, LINC00319, CYP3A7, ABCA10, NOG, RGMA, SPANXN3, PGA5, MYRIP, KCNN2, and NALCN-AS1.

Also provided is a packaging and/or producer cell line, wherein said cell line exhibits reduced expression and/or activity of a polypeptide or polyribonucleotide expressed from at least one of ATP5EP2, LINC00319, CYP3A7, ABCA10, NOG, RGMA, SPANXN3, PGA5, MYRIP, KCNN2, and NALCN-AS1 as compared to a corresponding parental cell line.

Other features and advantages of the disclosure will be apparent from the following detailed description and claims.

Unless noted to the contrary, all publications, references, patents and/or patent applications reference herein are hereby incorporated by reference in their entirety for all purposes.

BRIEF DESCRIPTION OF THE DRAWINGS

The disclosure can be more completely understood with reference to the following.

FIGS. 2A-2B show percent knockdown (FIG. 2A) and protein expression (FIG. 2B) data generated from HPRT1 siRNA knockdown experiments performed in 24 wells. FIGS. 2C-2D show percent knockdown (FIG. 2C) and protein expression (FIG. 2D) data generated from HPRT1 siRNA knockdown experiments performed in 6 wells.

FIGS. 5D-5F show the fold change in titers of rAAV produced from producer cell line #1 (FIG. 5D), producer cell line #2 (FIG. 5E), and producer cell line #3 (FIG. 5F). FIGS. 5A-5B show the average across 3 biological replicates. FIGS. 5C-5F show the average across 4 biological replicates.

FIG. 7A shows the 24 deep well titers of the top 19 2H5 knockout clones. Titer is reported as genome copies per mL. The control sample is unmodified 2H5. FIG. 7B shows the fold change in titer compared to the 2H5 control. 2H5 titer was set to 1 and other titers are displayed as the fold increase above the 2H5 control. FIG. 7C shows the 24 deep well titers of the top 19 7B12 knockout clones. Titer is reported as genome copies per mL. The control sample is unmodified 7B12. FIG. 7D shows the fold change in titer compared to the 7B12 control. 7B12 titer was set to 1 and other titers are displayed as the fold increase above the 7B12 control.

FIG. 9A shows the fold change in titer compared to the 2H5 missense control. 2H5 missense titer was set to 1 and other titers are displayed as the fold increase above the 2H5 missense control. FIG. 9B shows the fold change in titer compared to the 7B12 missense control. 7B12 missense titer was set to 1 and other titers are displayed as the fold increase above the 7B12 missense control.

DETAILED DESCRIPTION OF THE DISCLOSURE

Figure 1:
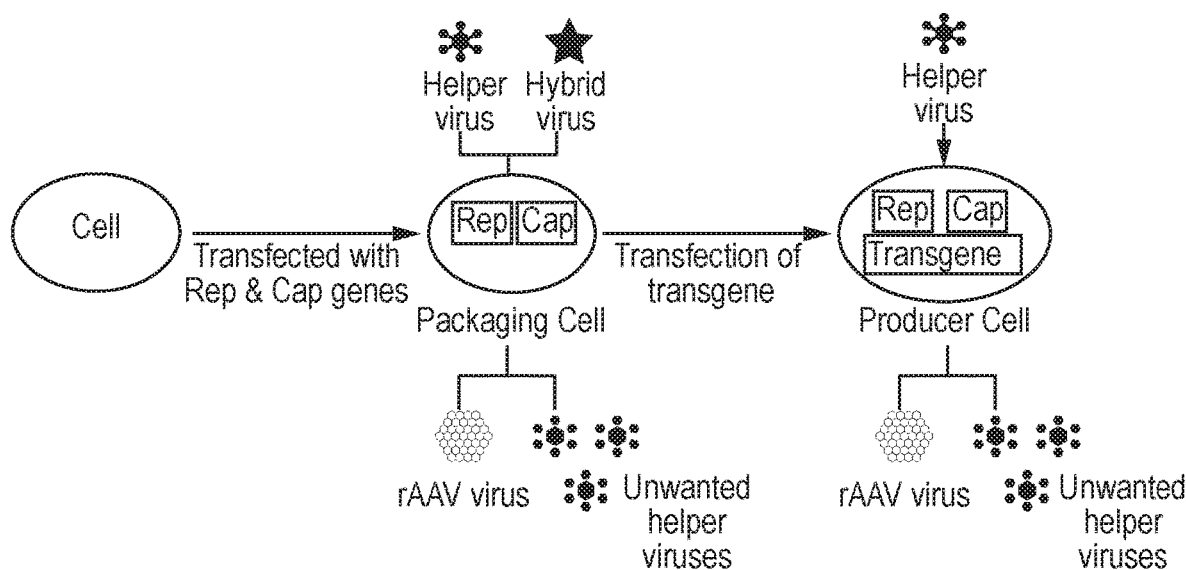
FIG. 1 is a schematic showing methods of generating rAAV packaging and producer cells described herein.

The present disclosure describes a recombinant adeno-associated virus (rAAV) packaging and/or producer cell line comprising cells in which expression of one or more genes and/or proteins is modulated. The modulation of gene expression results in an increased titer yield compared to a cell line in which expression of one or more genes and/or proteins in not modulated.

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8.

The following definitions are included for the purpose of understanding the present subject matter and for constructing the appended patent claims. Abbreviations used herein have their conventional meaning within the chemical and biological arts.

Definitions

As used herein, "modulation" or "modulate" refers to the alteration of the regulation, expression or activity of a gene and/or protein. Modulation may be increasing, reducing (decreasing), or eliminating the expression and/or activity of one or more genes and/or proteins. In cases where multiple genes and/or proteins are modulated, all the expression and/or activity of genes and/or proteins may be increased, or all the expression and/or activity of genes and/or proteins may be decreased, or one or more genes and/or proteins may be increased and others of the genes and/or proteins may be decreased.

As used herein, the term "cell" refers to any cell or cells capable of producing a recombinant adeno-associated virus (rAAV). In some embodiments, the cell is a mammalian cell, for example, a HeLa cell, a COS cell, a HEK293 cell, a A549 cell, a BHK cell, or a Vero cell. In other embodiments, the cell is an insect cell, for example, a Sf9 cell, a Sf-21 cell, a Tn-368 cell, or a BTI-Tn-5B1-4 (High-Five) cell. The term "cell line" refers to a clonal population of cells able to continue to divide and not undergo senescence. Unless otherwise indicated, the terms "cell" or "cell line" are understood to include modified or engineered variants of the indicated cell or cell line.

As used herein, the term "engineered cell line" refer to cell lines that have been modified by one or more means to reduce the expression or other properties (e.g., biological activity) of one or more endogenously expressed genes and/or proteins (e.g., ATP5EP2, LINC00319, CYP3A7, ABCA10, NOG, RGMA, SPANXN3, PGA5, MYRIP, KCNN2, and/or NALCN-AS1) so as to augment the production of rAAV.

As used herein, the term "control parental cells" refer to cells that have not been modified by one or more means to reduce the expression or other properties (e.g., biological activity) of one or more endogenously expressed genes and/or proteins (e.g., ATP5EP2, LINC00319, CYP3A7, ABCA10, NOG, RGMA, SPANXN3, PGA5, MYRIP, KCNN2, and/or NALCN-AS1) so as to augment the production of rAAV.

As used herein, the term "control parental cell line" refers to a clonal population of control parental cells able to continue to divide and not undergo senescence.

"Lysis" refers to the breaking down of the cell, often by viral, enzymatic, or osmotic mechanisms that compromise its integrity. A "lysed cell" is a cell that has undergone substantial lysis. As used herein, the term "lysate" refers to a fluid containing the contents of lysed cells.

As used herein, the term "higher titer" signifies an increased titer in comparison to titer produced by an unmodified control parental cell line and/or control parental cell.

As used herein, the term "cell culture supernatant" refers to the cell culture media in which cells are suspended and/or cultured.

As used herein, the term "gene" refers to a transcription unit and regulatory regions that are adjacent (e.g., located upstream and downstream), and operably linked, to the transcription unit. A transcription unit is a series of nucleotides that are transcribed into an RNA molecule. A transcription unit may include a coding region. A "coding region" is a nucleotide sequence that encodes an unprocessed preRNA (i.e., an RNA molecule that includes both exons and introns) that is subsequently processed to an mRNA. A transcription unit may encode a non-coding RNA. A non-coding RNA is an RNA molecule that is not translated into a protein. Examples of non-coding RNAs include microRNA. The boundaries of a transcription unit are generally determined by an initiation site at its 5' end and a transcription terminator at its 3' end. A "regulatory region" is a nucleotide sequence that regulates expression of a transcription unit to which it is operably linked. Nonlimiting examples of regulatory sequences include promoters, enhancers, transcription initiation sites, translation start sites, translation stop sites, transcription terminators, and poly(A) signals. A regulatory region located upstream of a transcription unit may be referred to as a 5' UTR, and a regulatory region located downstream of a transcription unit may be referred to as a 3' UTR. A regulatory region may be transcribed and be part of an unprocessed preRNA.

In the context of this document, the term "target" or "target gene" refers to any gene, including protein-encoding genes and genes encoding non-coding RNAs (e.g., miRNA), that when modulated alters some aspect of virus production. Target genes include endogenous genes, viral genes, and transgenes.

With regard to gene designations, single genes have often been denoted by multiple symbols. In the context of this document, gene symbols, whether they be human or non-human, may be designated by either upper-case or lower case letters. Neither the use of one particular symbol nor the adoption of lower or upper case symbols is intended to limit the scope of the gene in the context of these disclosures. All gene identification numbers identified herein (GeneID) are derived from the National Center for Biotechnology Information "Entrez Gene" or KEGG web site unless identified otherwise.

The term "about" is used herein to mean approximately, in the region of, roughly or around. When the term "about" is used in conjunction with a numerical range, it modifies that range by extending, within permissible value ranges, the boundaries above and/or below the numerical values set forth.

As used in the present disclosure, whether in a transitional phrase or in the body of a claim, the terms "comprise(s)" and "comprising" are to be interpreted as having an open-ended meaning. That is, the terms are to be interpreted synonymously with the phrases "having at least" or "including at least." When used in the context of a method, the term "comprising" means that the method includes at least the recited steps, but may include additional steps. When used in the context of a composition, the term "comprising" means that the composition includes at least the recited features or components, but may also include additional features or components.

For the purposes of promoting an understanding of the embodiments described herein, reference made to preferred embodiments and specific language is used to describe the same. The terminology used herein is for the purpose of describing particular embodiments only, and is not intended to limit the scope of the present disclosure. As used throughout this disclosure, the singular forms "a," "an," and "the" include plural reference unless the context clearly dictates otherwise. All percentages and ratios used herein, unless otherwise indicated, are by weight.

Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described below. In addition, the materials, methods and examples are illustrative only and are not intended to be limiting. All publications, patent applications, patents and other references mentioned herein are incorporated by reference.

Adeno-Associated Virus (AV)

AAV is a small, replication-defective, non-enveloped virus that infects humans and some other primate species. AAV is not known to cause disease and elicits a very mild immune response. Gene therapy vectors that utilize AAV can infect both dividing and quiescent cells and can persist in an extrachromosomal state without integrating into the genome of the host cell. These features make AAV an attractive viral vector for gene therapy. AAV includes numerous serologically distinguishable types including serotypes AAV-1 to AAV-12, as well as more than 100 serotypes from nonhuman primates (See, e.g., Srivastava, J. Cell Biochem., 105(1): 17-24 (2008), and Gao et al., J. Virol., 78(12), 6381-6388 (2004)). AAV is non-autonomously replicating, and has a life cycle with a latent phase and an infectious phase. In the latent phase, after a cell is infected with an AAV, the AAV site-specifically integrates into the host's genome as a provirus. The infectious phase does not occur unless the cell is also infected with a helper virus (for example, adenovirus (AV) or herpes simplex virus), which allows the AAV to replicate.

The wild-type AAV genome contains two 145 nucleotide inverted terminal repeats (ITRs), which contain signal sequences directing AAV replication, genome encapsidation and integration. In addition to the ITRs, three AAV promoters, p5, p19, and p40, drive expression of two open reading frames encoding rep and cap genes. Two rep promoters, coupled with differential splicing of the single AAV intron, result in the production of four rep proteins (Rep 78, Rep 68, Rep 52, and Rep 40) from the rep gene. Rep proteins are responsible for genomic replication. The cap gene is expressed from the p40 promoter, and encodes three capsid proteins (VP1, VP2, and VP3) which are splice variants of the cap gene. These proteins form the capsid of the AAV particle.

Because the cis-acting signals for replication, encapsidation, and integration are contained within the ITRs, some or all of the 4.3 kb internal genome may be replaced with foreign DNA, for example, an expression cassette for an exogenous protein of interest. In this case, the rep and cap proteins are provided in trans on, for example, a plasmid. In order to produce an AAV vector, a cell line permissive of AAV replication must express the rep and cap genes, the ITR-flanked expression cassette, and helper functions provided by a helper virus, for example AV genes E1a, Eb55K, E2a, E4orf6, and VA (Weitzman et al., Adeno-associated virus biology. Adeno-Associated Virus: Methods and Protocols, pp. 1-23, 2011). Production of AAV vector can also result in the production of helper virus particles, which must be removed or inactivated prior to use of the AAV vector. Numerous cell types are suitable for producing AAV vectors, including HEK293 cells, COS cells, HeLa cells, BHK cells, Vero cells, as well as insect cells (See e.g. U.S. Pat. Nos. 6,156,303, 5,387,484, 5,741,683, 5,691,176, 5,688,676, 8,163,543, U.S. Publication No. 20020081721, PCT Publication Nos. WO00/47757, WO00/24916, and WO96/17947). AAV vectors are typically produced in these cell types by one plasmid containing the ITR-flanked expression cassette, and one or more additional plasmids providing the additional AAV and helper virus genes.

AAV of any serotype may be used in the present disclosure. Similarly, it is contemplated that any AV type may be used, and a person of skill in the art will be able to identify AAV and AV types suitable for the production of their desired recombinant AAV vector (rAAV). AAV and AV particles may be purified, for example, by affinity chromatography, iodixanol gradient, or CsCl gradient.

The genome of wild-type AAV is single-stranded DNA and is 4.7 kb. AAV vectors may have single-stranded genomes that are 4.7 kb in size, or are larger or smaller than 4.7 kb, including oversized genomes that are as large as 5.2 kb, or as small as 3.0 kb. Further, vector genomes may be substantially self-complementary, so that within the virus the genome is substantially double stranded. AAV vectors containing genomes of all types are suitable for use in the method of the instant disclosure.

As discussed above, AAV requires co-infection with a helper virus in order to enter the infectious phase of its life cycle. Helper viruses include Adenovirus (AV), and herpes simplex virus (HSV), and systems exist for producing AAV in insect cells using baculovirus. It has also been proposed that papilloma viruses may also provide a helper function for AAV (see, e.g., Hermonat et al., Molecular Therapy 9, S289-S290 (2004)). Helper viruses include any virus capable of creating and allowing AAV replication. AV is a nonenveloped nuclear DNA virus with a double-stranded DNA genome of approximately 36 kb. AV is capable of rescuing latent AAV provirus in a cell, by providing E1a, E1b55K, E2a, E4orf6, and VA genes, and allowing AAV replication and encapsidation. HSV is a family of viruses that have a relatively large double-stranded linear DNA genome encapsidated in an icosahedral capsid, which is wrapped in a lipid bilayer envelope. HSV are infectious and highly transmissible. The following HSV-1 replication proteins were identified as necessary for AAV replication: the helicase/primase complex (UL5, UL8, and UL52) and the DNA binding protein ICP8 encoded by the UL29 gene, with other proteins enhancing the helper function. An AAV packaging system serves two purposes: it circumvents the problem of the transfection process, and provide a production technology based on the use of one or several helper functions.

Production of rAAV

General principles of rAAV can be reviewed elsewhere (See, e.g., Carter, 1992, Current Opinions in Biotechnology, 3:533-539; and Muzyczka, 1992, Curr. Topics in Microbiol. and Immunol., 158:97-129). In general terms, to allow for production of rAAV, the cell must be provided with AAV ITRs, which may, for example, flank a heterologous nucleotide sequence of interest, AAV rep and cap gene functions, as well as additional helper functions. These may be provided to the cell using any number of appropriate plasmids or vectors. Additional helper functions can be provided by, for example, an adenovirus (AV) infection, by a plasmid that carries all of the required AV helper function genes, or by other viruses such as HSV or baculovirus. Any genes, gene functions, or genetic material necessary for rAAV production by the cell may transiently exist within the cell, or be stably inserted into the cell genome. rAAV production methods suitable for use with the methods of the current disclosure include those disclosed in Clark et al., Human Gene Therapy 6:1329-1341 (1995), Martin et al., Human Gene Therapy Methods 24:253-269 (2013), Thorne et al., Human Gene Therapy 20:707-714 (2009), Fraser Wright, Human Gene Therapy 20:698-706 (2009), and Virag et al., Human Gene Therapy 20:807-817 (2009). The two main approaches for AAV production systems are recombinant adeno-associated virus (rAAV) packaging cell line and adeno-associated virus (rAAV) producer cell line.

Recombinant Adeno-Associated Virus (rAAV) Packaging and/or Producer Cell Line

A rAAV packaging cell line can be produced by allowing cellular expression of AAV genetic elements described herein. The stable transfection of a cell line (e.g., HEK293, HeLa) with a plasmid encoding the AAV rep and cap genes can result in production of a packaging cell line. This rAAV packaging cell line can be co-infected with two different adenoviruses (helper virus and hybrid virus that contains the AAV gene-therapy elements) to produce rAAV particles. Alternatively, the stable transfection of the packaging cells with a plasmid containing the rAAV vector or their infection with a rAAV vector leads to a rAAV producer cell line. The infection of the producer cells with a helper virus leads to production of rAAV. FIG. 1 illustrates the packaging and producer cell lines.

In certain embodiments of the present disclosure, the rAAV packaging cell line comprising AAV rep and cap gene functions is engineered to increase the rAAV titer.

In one aspect, the present disclosure provides a rAAV packaging cell line comprising cells in which expression of one or more genes and/or proteins is reduced compared to control parental cells. For example, expression of ATP5EP2, LINC00319, CYP3A7, ABCA10, NOG, RGMA, SPANXN3, PGA5, MYRIP, KCNN2, and/or NALCN-AS1 is reduced compared to control parental cells.

In some embodiments, the present disclosure provides a rAAV packaging cell line comprising cells in which expression of KCNN2, LINC00319, RGMA, and SPANXN3 is reduced compared to control parental cells.

In other embodiments, the present disclosure provides a rAAV producer cell line comprising cells in which expression of one or more genes and/or proteins is reduced compared to control parental cells. For example, expression of ATP5EP2, LINC00319, CYP3A7, ABCA10, NOG, RGMA, SPANXN3, PGA5, MYRIP, KCNN2, and/or NALCN-AS1 is reduced compared to control parental cells. In some embodiments, the rAAV producer cell line of the present disclosure has been engineered to reduce gene expression of KCNN2, LINC00319, RGMA, and SPANXN3.

In certain embodiments, the cell line of the present disclosure may be in an adherent or suspension form.

In certain embodiments, the cell line of the present disclosure (e.g., rAAV packaging and/or producer cell line) is a mammalian cell line (e.g., HeLa, human embryonic kidney (HEK) 293, COS, A549, or Vero cell line). In certain embodiments, the cell line is an insect cell line (e.g., Sf9, Sf-21, Tn-368, or BTI-Tn-5B1-4).

Method of Generating a rAAV Producer Cell Line

In some embodiments, the present disclosure provides a method of generating a producer cell line by delivering a rAAV vector to an engineered rAAV packaging cell line comprising cells in which the expression of ATP5EP2, LINC00319, CYP3A7, ABCA10, NOG, RGMA, SPANXN3, PGA5, MYRIP, KCNN2, and/or NALCN-AS1 is reduced compared to control cells.

In certain embodiments, the present disclosure provides a method of generating a producer cell line by delivering a rAAV vector to an engineered rAAV packaging cell line comprising cells in which the expression of KCNN2, LINC00319, RGMA, and SPANXN3 is reduced compared to control parental cells.

Supplements

As used herein, the term "supplements" refers to any compound or other material, whether chemical or biological in origin, which may be used in a media for cell culture to increase rAAV titers or to assay for increases in rAAV titers. Non-limiting examples of supplements include amino acids, salts, metals, sugars, lipids, nucleic acids, hormones, vitamins, fatty acids, proteins, enzymes, nucleosides, metabolites, surfactants, emulsifiers, inorganic salts, and polymers. In certain embodiments, the one or more supplements added to the rAAV packaging and/or producer cell line of the present disclosure is a glucocorticoid analog. In certain embodiments, the one or more supplements added to the rAAV packaging and/or producer cell line includes dexamethasone, hydrocortisone, prednisolone, methylprednisolone, betamethasone, cortisone, prednisone, budesonide, and/or triamcinolone.

In certain embodiments, the concentration of glucocorticoid analog in solution for increasing rAAV titer can be greater than or equal to 1 µM, greater than or equal to 0.1 µM, greater than or equal to 0.01 µM, between 0 and 1 µM, between 0 and 0.1 µM, between 0 and 0.01 µM, between 0.01 and 1 µM, or between 0.01 and 0.1 µM.

As used herein, "supplemented cell line" refers to a cell line (e.g., rAAV packaging and/or producer cell line) in which one or more supplements (e.g., glucocorticoid analogs) have been added to increase rAAV titer. As used herein, "non-supplemented cell line" refers to a cell line (e.g., rAAV packaging and/or producer cell line) not exposed to a supplement or supplements for increasing rAAV titer. As used herein, the terms "non-supplemented" and "unsupplemented" are used interchangeably to refer to culture conditions where the cell line (e.g., rAAV packaging and/or producer cell line) is not exposed to a supplement or supplements for increasing rAAV titer.

Method of Identifying One or More Genes Relevant to rAAV Production

The present disclosure is, in part, directed to a method of identifying one or more genes that are relevant to the production of rAAV by comparing global gene expression patterns in supplemented and non-supplemented cell lines.

The term "global gene expression" is well known in the art (See Wang Z. et al, Nature Reviews Genetics, 10(1), 57-63 (2009)). The term "global gene expression" refers to one or more sets of data that contain information regarding different aspects of gene expression. The data set optionally includes information regarding: the presence of target-transcripts in cell or cell-derived samples; the relative and absolute abundance levels of target transcripts; the ability of various treatments (e.g., addition of supplements) to modulate expression of specific genes; and the ability of various treatments (e.g., addition of supplements) to change expression of specific genes to different levels.

The term "differentially expressed" is well known in the art (see Wang Z. et al, Nature Reviews Genetics, 10(1), 57-63 (2009), Ozsolak, F. et al Nature Reviews Genetics, 12(2), 87-98 (2011), Han, Y. et al Bioinformatics and Biology Insights, 9, 29-46(2015))).

In certain embodiments, the cell line (e.g., rAAV packaging and/or producer cell line) of the present disclosure is supplemented with one or more supplements that increase the production of rAAV. In some embodiments, RNA samples are extracted from one or more cell lines (supplemented and non-supplemented) using any of well-known procedures. For example, total RNA can be purified from cells using silica-based isolation in an automation-compatible, 96-well format, such as the Rneasy® purification platform (Qiagen, Inc.; Valencia, Calif.).

Patterns of gene expression in expressed RNA samples can be evaluated by either (or both) qualitative and quantitative measures. In some embodiments, it is useful to quantitate the level of expression of a gene relative to other expression products, and/or relative to a control sequence. One convenient and broadly applicable method of determining relative expression is to compare the expression of one or more genes of interest to the expression of a control gene, such as a housekeeping gene (e.g., HPRT1, HSP70, or β-actin).

In order to ascertain whether the observed expression data, e.g., a change in gene expression profile in response to one or more treatments (e.g., addition of supplements) of a biological sample (e.g., supplemented and non-supplemented cell lines), is significant, and for example, not just a product of experimental noise or population heterogeneity, an estimate of a probability distribution can be constructed for each genetic and phenotypic endpoint in each biological sample. Construction of the estimated population distribution involves running multiple independent experiments for each treatment, e.g., all experiments are run in duplicate, triplicate, quadruplicate or the like. The expression data from multiple biological samples (e.g., supplemented and non-supplemented cell lines) can be grouped, or clustered, using multivariate statistics. Analysis of the data can produce a list of genes that are differentially expressed in response to treatment, for example, between supplemented and non-supplemented cell lines. The list of differentially expressed genes can be filtered using various gene filtering methodologies to identify one or more genes that are useful for increasing production of rAAV.

In some embodiments, the present disclosure is directed to methods of identifying one or more genes from a list of genes differentially expressed between supplemented and non-supplemented cell lines that are relevant to the production of rAAV. In certain embodiments, the cell line is a eukaryotic cell line. In certain embodiments, the cell line is a human cell line. In certain embodiments, the cell line is a HeLa cell line or a HEK293 cell line. In certain embodiments, global gene expression is measured across different cell lines (e.g., between a non-supplemented HeLa and a supplemented HeLa cell line, between a non-supplemented HEK 293 and a supplemented HEK 293 cell line, between a non-supplemented HeLa and a supplemented HEK 293 cell line, between a non-supplemented HeLa and a non-supplemented HEK 293 cell line, between a supplemented HeLa and a supplemented HEK 293 cell line) to identify one or more genes that are relevant to the production of rAAV. In certain embodiments, the global gene expression data from a supplemented HEK 293 and a supplemented HeLa can be combined and compared to the combined global gene expression data from a non-supplemented HEK 293 and a non-supplemented HeLa cell line to identify one or more genes that are relevant to the production of rAAV.

In certain embodiments, the present disclosure provides a method of producing a rAAV packaging and/or producer cell line to promote increased production of rAAV. In some embodiments, rAAV production is increased by modulating the expression of one or more genes and/or proteins identified from a list of genes that are differentially expressed between supplemented and non-supplemented rAAV producer cell lines. In certain embodiments, the titer of rAAV is increased by modulating the expression of one or more genes and/or proteins identified from a list of differentially expressed genes between supplemented and non-supplemented rAAV producer cell lines. In some embodiments, the rAAV titer is increased at least 1.5 fold (e.g., 2 fold, 3 fold, 4 fold, 5 fold, 6 fold, 7 fold, 8 fold, 9 fold, 10 fold, 20 fold, or 30 fold) compared to the rAAV titer produced by a cell line without the modulation of expression of the corresponding gene(s) and/or protein(s).

Modulated Genes and/or Proteins

In certain embodiments, the present disclosure provides a list of genes that when modulated (individually or in combinations) in a rAAV packaging and/or producer cell line enhance the production of rAAV.

ATP synthase F1 subunit epsilon pseudogene 2 (also known as ATP5EP2) encodes the ATP synthase subunit epsilon-like protein, mitochondrial. ATP5EP2 is a mitochondrial membrane ATP synthase that produces ATP from ADP in the presence of a proton gradient across the membrane which is generated by electron transport complexes of the respiratory chain. Examples of human ATP5EP2 sequences are available under the reference sequence NM_006886.4 (SEQ ID NO: 43) or NG_053163.1 (SEQ ID NO: 44) in the NCBI nucleotide database (nucleotide sequence).

Long Intergenic Non-Protein Coding RNA 319 (also known as LINC00319) is an RNA gene, and is affiliated with the non-coding RNA class. Long non-coding RNAs (lncRNAs) have been shown to play important regulatory roles in the pathogenesis and progression of multiple cancers. Examples of LINC00319 sequences are available under the reference sequence NM_194309 (SEQ ID NO: 45) or NR_026960.1 (SEQ ID NO: 46) in the NCBI nucleotide database (nucleotide sequence).

Cytochrome P450 Family 3 Subfamily A Member 7 (also known as CYP3A7) is a gene that encodes a member of the cytochrome P450 superfamily of enzymes, which participate in drug metabolism and the synthesis of cholesterol, steroids and other lipids. This enzyme hydroxylates testosterone and dehydroepiandrosterone 3-sulphate, which is involved in the formation of estriol during pregnancy. This gene is part of a cluster of related genes on chromosome 7q21.1. Examples of CYP3A7 sequences are available under the reference sequence NM_000765 (SEQ ID NO: 47) in the NCBI nucleotide database (nucleotide sequence).

ATP Binding Cassette Subfamily A Member 10 (also known as ABCA10) encodes a membrane-associated protein that belongs to a member of the superfamily of ATP-binding cassette (ABC) transporters. ABC proteins transport various molecules across extra- and intracellular membranes. ABC genes are divided into seven distinct subfamilies (ABC1, MDR/TAP, MRP, ALD, OABP, GCN20, and White). ABCA10 is a member of the ABC1 subfamily. Members of the ABC1 subfamily comprise the only major ABC subfamily found exclusively in multicellular eukaryotes. This gene is clustered among four other ABC1 family members on 17q24. Examples of ABCA10 sequences are available under the reference sequence NM_080282.3 (SEQ ID NO: 48) in the NCBI nucleotide database (nucleotide sequence).

Noggin (also known as NOG) encodes a secreted polypeptide that binds and inactivates members of the transforming growth factor-beta (TGF-beta) superfamily signaling proteins, such as bone morphogenetic protein-4 (BMP4). Without being bound by theory, it is believed that by diffusing through extracellular matrices more efficiently than members of the TGF-beta superfamily, this protein may have a principal role in creating morphogenic gradients. NOG appears to have pleiotropic effect, both early in development as well as in later stages. Examples of NOG sequences are available under the reference sequence NM_005450.4 (SEQ ID NO: 49) in the NCBI nucleotide database (nucleotide sequence).

Repulsive Guidance Molecule BMP Co-Receptor A (also known as RGMA) is a gene that encodes a member of the repulsive guidance molecule family. The encoded protein is a glycosylphosphatidylinositol-anchored glycoprotein that functions as an axon guidance protein in the developing and adult central nervous system. This protein may also function as a tumor suppressor in some cancers. Examples of RGMA sequences are available under the reference sequence NM_020211.2 (SEQ ID NO: 50) or NM_001166283.1 (SEQ ID NO: 51) in the NCBI nucleotide database (nucleotide sequence).

SPANX (Sperm protein associated with the nucleus on the X chromosome) Family Member N3 (also known as SPANXN3) is a protein coding gene. Examples of SPANXN3 sequences are available under the reference sequence NM_001009609 (SEQ ID NO: 52) in the NCBI nucleotide database (nucleotide sequence).

Pepsinogen-5, Group I (also known as PGA5 or Pepsinogen A) encodes a protein precursor of the digestive enzyme pepsin, a member of the peptidase A1 family of endopeptidases. The encoded precursor is secreted by gastric chief cells and undergoes autocatalytic cleavage in acidic conditions to form the active enzyme, which functions in the digestion of dietary proteins. This gene is found in a cluster of related genes on chromosome 11, each of which encodes one of multiple pepsinogens. Examples of PGA5 sequences are available under the reference sequence NM_014224.4 (SEQ ID NO: 53) in the NCBI nucleotide database (nucleotide sequence).

Myosin VIIA And Rab Interacting Protein (also known as MYRIP) encodes a Rab effector protein involved in melanosome transport which serves as link between melanosome-bound RAB27A and the motor proteins MYO5A and MYO7A. This Rab effector protein functions as a protein kinase A-anchoring protein (AKAP) and may act as a scaffolding protein that links PKA to components of the exocytosis machinery, thus facilitating exocytosis, including insulin release. Examples of MYRIP sequences are available under the reference sequence NM_015460 (SEQ ID NO: 54) or NM_001284423.1 (SEQ ID NO: 55) in the NCBI nucleotide database (nucleotide sequence).

Potassium Calcium-Activated Channel Subfamily N Member 2 (also known as KCNN2) gene is a member of the KCNN family of potassium channel genes. The encoded protein is an integral membrane protein that forms a voltage-independent calcium-activated channel with three other calmodulin-binding subunits. Alternate splicing of this gene results in multiple transcript variants. Examples of KCNN2 sequences are available under the reference sequence NM_170775.2 (SEQ ID NO: 56) or NM_001278204.1 (SEQ ID NO: 57) in the NCBI nucleotide database (nucleotide sequence).

NALCN Antisense RNA 1 (also known as NALCN-AS1) is an RNA gene, and is affiliated with the non-coding RNA class. Examples of NALCN-AS1 sequences are available under the reference sequence NW_011332700.1 (SEQ ID NO: 58) or NR_047687.1 (SEQ ID NO: 59) in the NCBI nucleotide database (nucleotide sequence).

In certain embodiments, the present disclosure provides a rAAV packaging and/or producer cell line comprising cells in which the expression of ATP5EP2, LINC00319, CYP3A7, ABCA10, NOG, RGMA, SPANXN3, PGA5, MYRIP, KCNN2, and/or NALCN-AS1 is reduced compared to control parental cells.

In certain embodiments, the present disclosure provides a rAAV packaging and/or producer cell line comprising cells in which the expression of KCNN2, LINC00319, RGMA, and SPANXN3 is reduced compared to control parental cells.

In certain embodiments, the present disclosure provides a list of genes that when modulated individually in a rAAV packaging and/or producer cell line enhance the production of rAAV compared to a control parental cell line. In some aspects, the modulation of different combination of genes in a rAAV packaging and/or producer cell line increases the production of rAAV. In some aspects, modulating the expression of at least 1, at least 2, at least 3, at least 4, at least 5, at least 6, at least 7, at least 8, at least 9, at least 10, or at least 11 genes in a rAAV packaging and/or producer cell line results in increased rAAV production compared to a control parental cell line.

Methods of Modulating One or More Genes and/or Protein

Modulating (e.g., reducing) the expression or activity of a gene (e.g., ATP5EP2, LINC00319, CYP3A7, ABCA10, NOG, RGMA, SPANXN3, PGA5, MYRIP, KCNN2, or NALCN-AS1) can be achieved by different mechanisms, including, but not limited to, altering one or more of the following: 1) gene copy number, 2) transcription or translation of a gene, 3) transcript stability or longevity, 4) the number of copies of an mRNA or miRNA, 5) the availability of a non-coding RNA or non-coding RNA target site, 6) the position or degree of post-translational modifications on a protein, or 7) the activity of a protein. Tools that can be used to modulate gene expression include but are not limited to a nuclease, a double stranded RNA (dsRNA), a small interfering RNA (siRNA), a small hairpin RNA (shRNA), a microRNA (miRNA), an antisense RNA oligonucleotide (ASO), a gene disruption, or a partial or complete gene deletion.

Nuclease

In certain embodiments, gene modulation is achieved using zinc finger nucleases (ZFNs). Synthetic ZFNs are composed of a zinc finger binding domain fused with, e.g., a FokI DNA cleavage domain. ZFNs can be designed/engineered for editing the genome of a cell, including, but not limited to, knock out or knock in gene expression, in a wide range of organisms. Meganucleases, transcription activator-like effector nucleases (TALENs), or clustered regularly interspaced short palindromic repeats (CRISPR) associated proteins (e.g., Cas nucleases), and triplexes can also be used for genome engineering in a wide array of cell types. The described reagents can be used to target promoters, protein-encoding regions (exons), introns, 5' and 3' UTRs, and more.

Double Stranded RNA (dsRNA) Molecules for Modulation

In certain embodiments, double-stranded RNA (dsRNA) molecules may be used to modulate expression of one or more genes in a cell line described herein (e.g., a rAAV packaging and/or producer cell line). dsRNA molecules can be designed to antagonize one or more genes by sequence homology-based targeting of the corresponding RNA sequence. Such dsRNAs can be small interfering RNAs (siRNAs), small hairpin RNAs (shRNAs), or micro-RNAs (miRNAs). The sequence of such dsRNAs will comprise a complementary portion of the mRNA encoding the one or more genes to be modulated. This portion can be 100% complementary to the target portion within the mRNA, but lower levels of complementarity (e.g., 90% or more or 95% or more) can also be used. Typically the percent complementarity is determined over a length of contiguous nucleic acid residues. A dsRNA molecule of the disclosure may, for example, have at least 80% complementarity to the target portion within the mRNA measured over at least 10, at least 20, at least 30, at least 40, at least 50, at least 60, at least 70, at least 80, at least 90, or more nucleic acid residues. In some instances dsRNA molecule has at least 80% complementarity to the target portion of mRNA over the entire length of the dsRNA molecule.

Another gene targeting reagent that uses RNA interference (RNAi) pathways is small hairpin RNA, also referred to as shRNA. shRNAs delivered to cells via, e.g., expression constructs (e.g., plasmids, lentiviruses) have the ability to provide long term reduction of gene expression in a constitutive or regulated manner, depending upon the type of promoter employed. In one embodiment, the genome of a lentiviral particle is modified to include one or more shRNA expression cassettes that target a gene (or genes) of interest. Such lentiviruses can infect a cell, stably integrate their viral genome into the host genome, and express a shRNA in a constitutive, regulated, or (in the case where multiple shRNA are being expressed) constitutive and regulated fashion. Thus, in some embodiments shRNA can be designed to target individual variants of a single gene or multiple closely related gene family members. Individual shRNA can modulate collections of targets having similar or redundant functions or sequence motifs. The skilled person will recognize that lentiviral constructs can also incorporate cloned DNA, or ORF expression constructs.

In embodiments described herein, gene targeting reagents including small interfering RNAs (siRNA) as well as microRNAs (miRNA) can be used to modulate gene function. siRNAs and miRNAs can incorporate a wide range of chemical modifications, levels of complementarity to the target transcript of interest, and designs (see U.S. Pat. No. 8,188,060) to enhance stability, cellular delivery, specificity, and functionality. In addition, such reagents can be designed to target diverse regions of a gene (including the 5' UTR, the open reading frame, the 3' UTR of the mRNA), or (in some cases) the promoter/enhancer regions of the genomic DNA encoding the gene of interest. Gene modulation (e.g., reduction of gene expression, knockdown) can be achieved by introducing (into a cell) a single siRNA or miRNA or multiple siRNAs or pools of miRNAs targeting different regions of the same mRNA transcript. Synthetic siRNA/miRNA delivery can be achieved by any number of methods including but not limited to 1) self-delivery, 2) lipid-mediated delivery, 3) electroporation, or 4) vector/plasmid-based expression systems. An introduced RNA molecule may be referred to as an exogenous nucleotide sequence or polynucleotide. In some embodiments, siRNA can be designed to target individual variants of a single gene or multiple closely related gene family members.

siRNA can be used to reduce the expression of one or more genes (e.g., ATP5EP2, LINC00319, CYP3A7, ABCA10, NOG, RGMA, SPANXN3, PGA5, MYRIP, KCNN2, and/or NALCN-AS1). In some embodiments, a siRNA which comprises a nucleotide sequence selected from SEQ ID NOs: 1 to 11, or a variant thereof, is used to reduce the expression of a target gene.

TABLE 1 siRNA sequences used for reducing expression of genes.

| SEQ ID NO: | Target gene | siRNA Sequence* |
|---|---|---|
| SEQ ID NOS 1 and 32 | ATP5SEP2 | Sense: GCAACAGCGUAAAAAUUGUtt (SEQ ID NO: 1) Antisense: ACAAUUUUUACGCUGUUGCca (SEQ ID NO: 32) |
| SEQ ID NOS 2 and 33 | LINC00319 | Sense: CGGUGUCCACAGUCCUUGAtt (SEQ ID NO: 2) Antisense: UCAAGGACUGUGGACACCGgt (SEQ ID NO: 33) |
| SEQ ID NOS 3 and 34 | CYP3A7 | Sense: CAAGAAAAGUUAUAAGUUUtt (SEQ ID NO: 3) Antisense: AAACUUAUAACUUUUCUUGga (SEQ ID NO: 34) |
| SEQ ID NOS 4 and 35 | NOG | Sense: CGGAGGAAGUUACAGAUGUtt (SEQ ID NO: 4) Antisense: ACAUCUGUAACUUCCUCCGca (SEQ ID NO: 35) |
| SEQ ID NOS 5 and 36 | SPANXN3 | Sense: AGAUGCAAGAGGUACCAAAtt (SEQ ID NO: 5) Antisense: UUUGGUACCUCUUGCAUCUca (SEQ ID NO: 36) |
| SEQ ID NOS 6 and 37 | MYRIP | Sense: GGUGUCGGAUGAUUUAUCAtt (SEQ ID NO: 6) Antisense: UGAUAAAUCAUCCGACACCtg (SEQ ID NO: 37) |
| SEQ ID NOS 7 and 38 | KCNN2 | Sense: GAAGCUAGAACUUACCAAAtt (SEQ ID NO: 7) Antisense: UUUGGUAAGUUCUAGCUUCct (SEQ ID NO: 38) |
| SEQ ID NOS 8 and 39 | NALCN-AS1 | Sense: GGAUGUCUUUCCUAGGAGAtt (SEQ ID NO: 8) Antisense: UCUCCUAGGAAAGACAUCCaa (SEQ ID NO: 39) |
| SEQ ID NOS 9 and 40 | RGMA | Sense: CGCUCAUCGACAAUAAUUAtt (SEQ ID NO: 9) Antisense: UAAUUAUUGUCGAUGAGCGgc (SEQ ID NO: 40) |
| SEQ ID NOS 10 and 41 | PGA5 | Sense: CACUUUAGAUGUAUCUAAUtt (SEQ ID NO: 10) Antisense: AUUAGAUACAUCUAAAGUGgg (SEQ ID NO: 41) |
| SEQ ID NOS 11 and 42 | ABCA10 | Sense: GGAGCAUAAAGUAGACCGAtt (SEQ ID NO: 11) Antisense: UCGGUCUACUUUAUGCUCCtt (SEQ ID NO: 42) |

*siRNA sequences (sense and antisense) used for reducing expression of genes. Lower case nucleotides in the sequences represent 3' overhang.

In some embodiments, the siRNA used to reduce the expression of ATP5EP2 comprises the nucleotide sequence of SEQ ID NO: 1, or a variant thereof. For example, in some embodiments, the siRNA comprises the nucleotide sequence of SEQ ID NO: 1 in the sense strand and the nucleotide sequence of SEQ ID NO: 32 in the anti-sense strand.

In some embodiments, the siRNA used to reduce the expression of LINC00319 comprises the nucleotide sequence of SEQ ID NO: 2, or a variant thereof. For example, in some embodiments, the siRNA comprises the nucleotide sequence of SEQ ID NO: 2 in the sense strand and the nucleotide sequence of SEQ ID NO: 33 in the anti-sense strand.

In some embodiments, the siRNA used to reduce the expression of CYP3A7 comprises the nucleotide sequence of SEQ ID NO: 3, or a variant thereof. For example, in some embodiments, the siRNA comprises the nucleotide sequence of SEQ ID NO: 3 in the sense strand and the nucleotide sequence of SEQ ID NO: 34 in the anti-sense strand.

In some embodiments, the siRNA used to reduce the expression of NOG comprises the nucleotide sequence of SEQ ID NO: 4, or a variant thereof. For example, in some embodiments, the siRNA comprises the nucleotide sequence of SEQ ID NO: 4 in the sense strand and the nucleotide sequence of SEQ ID NO: 35 in the anti-sense strand.

In some embodiments, the siRNA used to reduce the expression of SPANXN3 comprises the nucleotide sequence of SEQ ID NO: 5, or a variant thereof. For example, in some embodiments, the siRNA comprises the nucleotide sequence of SEQ ID NO: 5 in the sense strand and the nucleotide sequence of SEQ ID NO: 36 in the anti-sense strand.

In some embodiments, the siRNA used to reduce the expression of MYRIP comprises the nucleotide sequence of SEQ ID NO: 6, or a variant thereof. For example, in some embodiments, the siRNA comprises the nucleotide sequence of SEQ ID NO: 6 in the sense strand and the nucleotide sequence of SEQ ID NO: 37 in the anti-sense strand.

In some embodiments, the siRNA used to reduce the expression of KCNN2 comprises the nucleotide sequence of SEQ ID NO: 7, or a variant thereof. For example, in some embodiments, the siRNA comprises the nucleotide sequence of SEQ ID NO: 7 in the sense strand and the nucleotide sequence of SEQ ID NO: 38 in the anti-sense strand.

In some embodiments, the siRNA used to reduce the expression of NALCN-AS1 comprises the nucleotide sequence of SEQ ID NO: 8, or a variant thereof. For example, in some embodiments, the siRNA comprises the nucleotide sequence of SEQ ID NO: 8 in the sense strand and the nucleotide sequence of SEQ ID NO: 39 in the anti-sense strand.

In some embodiments, the siRNA used to reduce the expression of RGMA comprises the nucleotide sequence of SEQ ID NO: 9, or a variant thereof. For example, in some embodiments, the siRNA comprises the nucleotide sequence of SEQ ID NO: 9 in the sense strand and the nucleotide sequence of SEQ ID NO: 40 in the anti-sense strand.

In some embodiments, the siRNA used to reduce the expression of PGA5 comprises the nucleotide sequence of SEQ ID NO: 10, or a variant thereof. For example, in some embodiments, the siRNA comprises the nucleotide sequence of SEQ ID NO: 10 in the sense strand and the nucleotide sequence of SEQ ID NO: 41 in the anti-sense strand.

In some embodiments, the siRNA used to reduce the expression of ABCA10 comprises the nucleotide sequence of SEQ ID NO: 11, or a variant thereof. For example, in some embodiments, the siRNA comprises the nucleotide sequence of SEQ ID NO: 11 in the sense strand and the nucleotide sequence of SEQ ID NO: 42 in the anti-sense strand.

Antisense RNA Oligonucleotide (ASO)

Antisense RNA oligonucleotide (ASO), can be used to modulate expression of one or more genes in a rAAV packaging and/or producer cell line. Typically, ASOs are used to reduce expression of one or more genes. Using known techniques and based on a knowledge of the sequence of the one or more gene to be modulated, ASO molecules can be designed to antagonize the one or more genes by sequence homology-based targeting of the corresponding RNA. The ASO sequence can comprise nucleotide sequence that is complementary to a target portion of the mRNA or lncRNA produced from the one or more genes. This portion can be 100% complementary to the target portion within the mRNA or lncRNA but lower levels of complementarity (e.g., 90% or more or 95% or more) can also be used.

In some embodiments, the ASO can be an antisense RNA oligonucleotide wherein at least one nucleoside linkage of the sequence is a phosphorothioate linkage, a phosphorodithioate linkage, a phosphotriester linkage, an alkylphosphonate linkage, an aminoalkylphosphotriester linkage, an alkylene phosphonate linkage, a phosphinate linkage, a phosphoramidate linkage, and an aminoalkylphosphoramidate linkage, a thiophosphoramidate linkage, thionoalkylphosphonate linkage, a thionoalkylphosphotriester linkage, a thiophosphate linkage, a selenophosphate linkage, or a boranophosphate linkage. In a particular embodiment, at least one internucleoside linkage of the antisense RNA oligonucleotide sequence is a phosphorothioate linkage. In some embodiments, all of the internucleoside linkages of the antisense RNA oligonucleotide sequence are phosphorothioate linkages.

CRISPR Genome Editing

In some embodiments, modulation of gene expression in a rAAV packaging and/or producer cell line is carried out using CRISPR genome editing. The CRISPR genome editing typically comprises two distinct components: (1) a guide RNA and (2) an endonuclease, specifically a CRISPR associated (Cas) nuclease (e.g., Cas9). The guide RNA is a combination of the endogenous bacterial crRNA and tracrRNA into a single chimeric guide RNA (gRNA) transcript. Without being bound by theory, it is believed that when gRNA and the Cas are expressed in the cell, the genomic target sequence can be modified or permanently disrupted.

The gRNA/Cas complex is recruited to the target sequence by base-pairing between the gRNA sequence and the complement to the target DNA sequence in the gene for reduction (e.g., ATP5EP2, LINC00319, CYP3A7, ABCA10, NOG, RGMA, SPANXN3, PGA5, MYRIP, KCNN2, or NALCN-AS1). For successful binding of Cas, the genomic target sequence must also contain the correct Protospacer Adjacent Motif (PAM) sequence immediately following the target sequence. The binding of the gRNA/Cas complex localizes the Cas to the genomic target sequence in the one or more genes of the present disclosure so that the wild-type Cas can cut both strands of DNA causing a double strand break. This can be repaired through one of two general repair pathways: (1) the non-homologous end joining DNA repair pathway or (2) the homology directed repair pathway. The non-homologous repair pathway can result in inserts/deletions at the double strand break that can lead to frameshifts and/or premature stop codons, effectively disrupting the open reading frame of the target gene. The homology directed repair pathway requires the presence of a repair template, which is used to fix the double strand break.

Any appropriate gRNA pair may be used for CRISPR genome editing. Typically gRNA pairs are used to reduce expression of one or more genes (e.g., ATP5EP2, LINC00319, CYP3A7, ABCA10, NOG, RGMA, SPANXN3, PGA5, MYRIP, KCNN2, and NALCN-AS1). In some embodiments described herein, a gRNA pair is used to modulate (e.g., reduce or eliminate/knockout) expression of ATP5EP2, LINC00319, CYP3A7, ABCA10, NOG, RGMA, SPANXN3, PGA5, MYRIP, KCNN2, and/or NALCN-AS1.

gRNA pairs can be designed using known techniques and based on a knowledge of the sequence of the one or more genes to be modulated, typically using any publicly available appropriate computer program. Knock out packaging and/or producer cells may be generated using any appropriate technique, with standard techniques being known in the art and suitable kits being commercially available.

gRNA pairs can be delivered to a producer cell line of the disclosure by any appropriate means. Suitable techniques are known in the art and include the use of plasmid, viral and bacterial vectors to deliver the gRNA pairs to the producer cell line. Typically, a gRNA pair is delivered using plasmid DNA.

gRNA pairs may be used to reduce the expression of one or more of genes (e.g., ATP5EP2, LINC00319, CYP3A7, ABCA10, NOG, RGMA, SPANXN3, PGA5, MYRIP, KCNN2, and NALCN-AS1). Multiple gRNA pairs may be used to modulate the expression of a gene. In some embodiments described herein, gRNA pairs are used to reduce the expression of at least one of ATP5EP2, LINC00319, CYP3A7, ABCA10, NOG, RGMA, SPANXN3, PGA5, MYRIP, KCNN2, or NALCN-AS1. Multiple gRNA pairs may be used to modulate the expression of KCNN2, LINC00319, RGMA, and SPANXN3. In some embodiments, gRNAs may be modified to enhance editing efficiency by increasing binding to the target site and inhibiting nuclease degradation. In certain embodiments, these modifications may be 2'O-methyl analogs and 3' phosphorothioate inteucleotide linkages in the terminal three nucleotides on both 5' and 3' ends of the gRNA. Exemplary target DNA sequences targeted by gRNA pairs used to modulate gene expression of one or more genes may comprise any one of nucleotide sequences selected from SEQ ID NOs: 16-31 listed in Table 2, or variants thereof.

TABLE 2

Exemplary target region sequences of gRNA pairs (SEQ ID NO: 12-15) and target DNA sequences (SEQ ID NOs: 16-31)

| SEQ ID NO: | Sequence |
|---|---|
| | KCNN2 |
| SEQ ID NO: 12 | UUGCCACUACAGCUACCACC |
| SEQ ID NO: 13 | CCAAUGUACUCAGGGAAACA |
| SEQ ID NO: 14 | AGUCCACCAAAGUGUUUGCU |
| SEQ ID NO: 15 | AAAGGAGUCUGCUUACUUAC |
| | KCNN2 |
| SEQ ID NO: 16 | TTGCCACTACAGCTACCACC |
| SEQ ID NO: 17 | CCAATGTACTCAGGGAAACA |
| SEQ ID NO: 18 | AGTCCACCAAAGTGTTTGCT |
| SEQ ID NO: 19 | AAAGGAGTCTGCTTACTTAC |

TABLE 2-continued

Exemplary target region sequences of
gRNA pairs (SEQ ID NO: 12-15) and
target DNA sequences (SEQ ID NOs: 16-31)

| SEQ ID NO: | Sequence |
|---|---|
| RGMA | |
| SEQ ID NO: 20 | CTTCTCGTAATGGCAGATCT |
| SEQ ID NO: 21 | GCACTTGAGGATCTTGCACG |
| SEQ ID NO: 22 | GAGGTCCTCTATGCCATGGA |
| SEQ ID NO: 23 | CCATACCCATCCATCCAGCT |
| SPANXN3 | |
| SEQ ID NO: 24 | CCCATGTGAAGGACCTTCAA |
| SEQ ID NO: 25 | GTTCTTCAAACTCTGTTCGG |
| SEQ ID NO: 26 | GAAGGCGTAGACTTATCTGA |
| SEQ ID NO: 27 | AGCCAACTTCCAGCACCAAT |
| LINC00319 | |
| SEQ ID NO: 28 | GGGCAATGGACCTTCTGCCT |
| SEQ ID NO: 29 | GGCTGCGGGGCAGAGGGCAA |
| SEQ ID NO: 30 | CGGGCAGGCTGCGGGGCAGA |
| SEQ ID NO: 31 | ACGGGCAGGCTGCGGGGCAG |

For example, gRNA pairs used to target KCNN2 can comprise a sequence selected from the nucleotide sequences of SEQ ID NO: 12-15 (shown in Table 2). In some embodiments, a gRNA pair used to target KCNN2 comprises a first gRNA molecule comprising the sequence of SEQ ID NO: 12 and a second gRNA molecule comprising the sequence of SEQ ID NO: 13. In some embodiments, a gRNA pair used to target KCNN2 comprises a first gRNA molecule comprising or having the sequence of SEQ ID NO: 14 and a second gRNA molecule comprising or having the sequence of SEQ ID NO: 15.

In some embodiments, a gRNA molecule to target KCNN2 is a 2'O-methyl analog comprising 3' phosphorothioate internucleotide linkages in the terminal three nucleotides on either or both its 5' and 3' ends and comprises the sequence of SEQ ID NO: 12, 13, 14, or 15.

A variant gRNA sequence may have at least 80% sequence identity to a sequence of the present disclosure, measured over any appropriate length of sequence. Typically the percent sequence identity is determined over a length of contiguous nucleic acids. A variant gRNA sequence of the present disclosure can, for example, have at least 80% sequence identity to a sequence of the present disclosure measured over at least 10, at least 11, at least 12, at least 13, at least 14, at least 15, at least 16, at least 17, at least 18, at least 19, at least 20, at least 21, at least 22, at least 23, at least 24, or more nucleic acid residues. In some embodiments, the variant gRNA molecule has at least 80% sequence identity with the gRNA molecule of the present disclosure over the entire length of the variant gRNA molecule. In some embodiments, a variant gRNA molecule of the present disclosure can be a variant of one or more of the gRNA molecules whose target regions are complementary to a target sequence of one of SEQ ID NOs: 16 to 30. gRNA pairs of the present disclosure may comprise a variant of one or both of two gRNA sequences in the pair targeting a gene, e.g., a gene selected from ATP5EP2, LINC00319, CYP3A7, ABCA10, NOG, RGMA, SPANXN3, PGA5, MYRIP, KCNN2, and NALCN-AS1. For example, a variant of the gRNA pair comprising a first gRNA molecule comprising the sequence of SEQ ID NO: 12 and a second gRNA molecule comprising the sequence of SEQ ID NO: 13 may comprise 1) a first gRNA molecule comprising a variant of the sequence of SEQ ID NO: 12, 2) a second gRNA molecule comprising a variant of the sequence of SEQ ID NO: 13, or 3) both.

Modulation at Protein Level

In another embodiment, modulation of expression and/or activity of a gene takes place at the protein (e.g., polypeptide) level. By way of example, reduction of gene function at the protein level can be achieved by methods including, but not limited to, targeting the protein with a small molecule, a peptide, an aptamer, destabilizing domains, or other methods that can e.g., down-regulate the activity or enhance the rate of degradation of a gene product. Alternatively, the expressed protein may be modified to reduce or eliminate biological activity through site-directed mutagenesis and/or the incorporation of missense or nonsense mutations. In some embodiments, a small molecule that binds, e.g., an active site and inhibits the function of a target protein can be added to, e.g., the cell culture media and thereby be introduced into a packaging and/or producer cell. Alternatively, target protein function can be modulated by introducing, e.g., a peptide into a cell (e.g., a packaging and/or producer cell) that for instance prevents protein-protein interactions (see Shangary et. al., (2009) *Annual Review of Pharmacology and Toxicology* 49:223). Such peptides can be introduced into a cell (e.g., a packaging and/or producer cell) by, for example, transfection or electroporation, or via an expression construct. Alternatively, peptides can be introduced into a cell (e.g., a packaging and/or producer cell) by adding (e.g., through conjugation) one or more moieties that facilitate cellular delivery, or supercharging molecules to enhance self-delivery. Techniques for expressing a peptide include, but are not limited to, fusion of the peptide to a scaffold, or attachment of a signal sequence, to stabilize or direct the peptide to a position or compartment of interest, respectively. In certain embodiments, a rAAV packaging and/or producer cell line comprises cells which have been engineered to reduce the expression and/or activity of a gene product expressed from ATP5EP2, LINC00319, CYP3A7, ABCA10, NOG, RGMA, SPANXN3, PGA5, MYRIP, KCNN2, and/or NALCN-AS1 using any of the aforementioned methods.

Effect of Modulation on Expression of One or More Genes and/or Proteins

In certain embodiments, methods of modulations described in the present disclosure can be utilized to generate a rAAV packaging and/or producer cell line that produces high titers of rAAV. In certain embodiments, methods of modulations described in the present disclosure can result in a significant reduction in expression of one or more genes (e.g., ATP5EP2, LINC00319, CYP3A7, ABCA10, NOG, RGMA, SPANXN3, PGA5, MYRIP, KCNN2, and/or NALCN-AS1) and/or a significant reduction in the activity of a protein expressed by one or more genes (e.g., a reduction of at least 5%, at least 10%, at least 20%, or greater reduction). In certain embodiments, expression of a target gene is reduced from about 40% to about 100% (for example, from about 40% to about 95%, from about 40% to about 90%, from about 40% to about 85%, from about 40% to about 80%, from about 40% to about 75%, from about 40% to about 70%, from about 40% to about 65%, from about 40% to about 60%, from about 40% to about 55%, from about 40% to about 50%, from about 40% to about 45%, from about 45% to about 100%, from about 50% to about 100%, from about 55% to about 100%, from about 60% to about 100%, from about 65% to about 100%, from about 70% to about 100%, from about 75% to about 100%, from about 80% to about 100%, from about 85% to about 100%, from about 90% to about 100%, from about 95% to about 100%; or about 40%, about 50%, about 60%, about 70%, about 80%, about 90%, about 100%).

In certain embodiments, methods of modulation described in the present disclosure can result in a significant reduction in activity of a protein or RNA expressed by a target gene (e.g., ATP5EP2, LINC00319, CYP3A7, ABCA10, NOG, RGMA, SPANXN3, PGA5, MYRIP, KCNN2, and/or NALCN-AS1). For example, methods described herein can result in at least 5%, at least 10%, at least 20% or greater reduction in activity of a protein or RNA expressed by a target gene. In certain embodiments, target gene protein or RNA activity is reduced from about 40% to about 100% (for example, from about 40% to about 95%, from about 40% to about 90%, from about 40% to about 85%, from about 40% to about 80%, from about 40% to about 75%, from about 40% to about 70%, from about 40% to about 65%, from about 40% to about 60%, from about 40% to about 55%, from about 40% to about 50%, from about 40% to about 45%, from about 45% to about 100%, from about 50% to about 100%, from about 55% to about 100%, from about 60% to about 100%, from about 65% to about 100%, from about 70% to about 100%, from about 75% to about 100%, from about 80% to about 100%, from about 85% to about 100%, from about 90% to about 100%, from about 95% to about 100%; or about 40%, about 50%, about 60%, about 70%, about 80%, about 90%, about 100%). Furthermore, modulation of one or more genes can result in modulation of multiple genes (e.g., by miRNAs).

In certain embodiments, methods of modulation described in the present disclosure can result in a significant reduction in expression of gene product (e.g., a gene product of ATP5EP2, LINC00319, CYP3A7, ABCA10, NOG, RGMA, SPANXN3, PGA5, MYRIP, KCNN2, and/or NALCN-AS1) (e.g., at least 5%, at least 10%, at least 20% or greater reduction). In certain embodiments, expression of a gene product is reduced from about 40% to about 100% (for example, from about 40% to about 95%, from about 40% to about 90%, from about 40% to about 85%, from about 40% to about 80%, from about 40% to about 75%, from about 40% to about 70%, from about 40% to about 65%, from about 40% to about 60%, from about 40% to about 55%, from about 40% to about 50%, from about 40% to about 45%, from about 45% to about 100%, from about 50% to about 100%, from about 55% to about 100%, from about 60% to about 100%, from about 65% to about 100%, from about 70% to about 100%, from about 75% to about 100%, from about 80% to about 100%, from about 85% to about 100%, from about 90% to about 100%, from about 95% to about 100%; or about 40%, about 50%, about 60%, about 70%, about 80%, about 90%, about 100%).

In certain embodiments, methods of modulation described in the present disclosure can result in a significant reduction in expression of polypeptide or polyribonucleotide expressed from at least one of ATP5EP2, LINC00319, CYP3A7, ABCA10, NOG, RGMA, SPANXN3, PGA5, MYRIP, KCNN2, and/or NALCN-AS1 (e.g., at least 5%, at least 10%, at least 20% or greater reduction). In certain embodiments, expression of polypeptide or polyribonucleotide is reduced from about 40% to about 100% (for example, from about 40% to about 95%, from about 40% to about 90%, from about 40% to about 85%, from about 40% to about 80%, from about 40% to about 75%, from about 40% to about 70%, from about 40% to about 65%, from about 40% to about 60%, from about 40% to about 55%, from about 40% to about 50%, from about 40% to about 45%, from about 45% to about 100%, from about 50% to about 100%, from about 55% to about 100%, from about 60% to about 100%, from about 65% to about 100%, from about 70% to about 100%, from about 75% to about 100%, from about 80% to about 100%, from about 85% to about 100%, from about 90% to about 100%, from about 95% to about 100%; or about 40%, about 50%, about 60%, about 70%, about 80%, about 90%, about 100%).

In certain embodiments, methods of modulation described in the present disclosure can result in a significant reduction in activity of a polypeptide or polyribonucleotide expressed from at least one of ATP5EP2, LINC00319, CYP3A7, ABCA10, NOG, RGMA, SPANXN3, PGA5, MYRIP, KCNN2, and/or NALCN-AS1 (e.g., at least 5%, at least 10%, at least 20% or greater reduction). In certain embodiments, activity of expressed polypeptide or polyribonucleotide is reduced from about 40% to about 100% (for example, from about 40% to about 95%, from about 40% to about 90%, from about 40% to about 85%, from about 40% to about 80%, from about 40% to about 75%, from about 40% to about 70%, from about 40% to about 65%, from about 40% to about 60%, from about 40% to about 55%, from about 40% to about 50%, from about 40% to about 45%, from about 45% to about 100%, from about 50% to about 100%, from about 55% to about 100%, from about 60% to about 100%, from about 65% to about 100%, from about 70% to about 100%, from about 75% to about 100%, from about 80% to about 100%, from about 85% to about 100%, from about 90% to about 100%, from about 95% to about 100%; or about 40%, about 50%, about 60%, about 70%, about 80%, about 90%, about 100%).

In certain embodiments, reduction in expression and/or activity of one or more genes, proteins, or RNAs in a rAAV packaging and/or producer cell line is maintained for about 5 days (e.g., about 6 hours, about 12 hours, about 1 day, about 2 days, about 3 days, about 4 days, about 5 days, about 6 days, about 7 days, about 8 days, about 9 days, about 10 days or more).

In certain embodiments, reduction in expression and/or activity of one or more genes, proteins, or RNAs in a rAAV packaging and/or producer cell line is intended to be maintained indefinitely or permanently, e.g., through the use of a gene disruption or a partial or complete gene deletion.

In certain embodiments, reduction in expression and/or activity of one or more genes, proteins, or RNAs in a rAAV packaging and/or producer cell line is maintained for at least one, at least two, at least three, at least four, at least five, at least ten, at least 20, at least 30, at least 40 or more passages of the rAAV packaging and/or producer cell line in culture.

Effect of Modulation on rAAV Production

Modulation of one or more genes and/or proteins in a rAAV packaging and/or producer cell line may result in an increase in the titer of rAAV. In some embodiments, modulation results in an increase in the titer of rAAV produced from the rAAV packaging and/or producer cell line is increased to about 1.5 to about 7-fold (e.g., about 1.5 to about 6.5, about 1.5 to about 6, about 1.5 to about 5.5, about 1.5 to about 5, about 1.5 to about 4.5, about 1.5 to about 4, about 1.5 to about 3.5, about 1.5 to about 3.0, about 1.5 to about 2.5, about 1.5 to about 2.0, about 2 to about 7, about 2.5 to about 7, about 3 to about 7, about 3.5 to about 7, about 4 to about 7, about 4.5 to about 7, about 5 to about 7, about 5.5 to about 7, about 6 to about 7, about 6.5 to about 7, or about 1.5, about 2.0, about 2.5, about 3.0, about 3.5, about 4.0, about 4.5, about 5.0, about 5.5, about 6.0, about 6.5, or about 7.0). In some embodiments, the titer of rAAV produced from the rAAV packaging and/or producer cell line is increased at least 2 fold, at least 3 fold, at least 4 fold, at least 5 fold, at least 6 fold, at least 7 fold, at least 8 fold, at least 9 fold, at least 10 fold, at least 15 fold, at least 20 fold or more. Any increase in the rAAV titer resulting from modulation of one or more genes and/or protein can be compared with the rAAV titer produced from a control parental cell line.

In some embodiments, modulation of one or more genes and/or proteins in a rAAV packaging and/or producer cell line may increase the rAAV titer production for at least 2 days, at least 5 days, at least 20 days, at least 30 days, at least 40 days, at least 50 days, at least 60 days, at least 70 days, at least 80 days, at least 90 days, at least 100 days or more.

Methods of Producing rAAV

In certain embodiments, the present disclosure describes a method of producing rAAV from rAAV packaging and/or producer cell lines that have been engineered to modulate the expression of one or more genes, proteins, or non-coding RNAs. In certain embodiments, rAAV is produced by infecting the cells of a rAAV producer cell line generated by delivering a rAAV vector to an engineered rAAV packaging cell line. In certain embodiments, rAAV is produced by infecting the cells of a rAAV producer cell line in which expression of one or more genes, proteins, or non-coding RNAs have been modulated. In certain embodiments, the production of rAAV from engineered rAAV packaging and/or producer cell line is enhanced as compared to a control parental cell line.

In certain embodiments, cells of the engineered packaging cell line are infected with a helper virus (e.g., adenovirus (AV) or herpes simplex virus), which allows the rAAV to replicate. In some embodiments, cells of the engineered producer cell line are infected with a helper virus (e.g., adenovirus (AV) or herpes simplex virus).

Methods of Harvesting rAAV rAAV particles may be obtained from engineered rAAV packaging and/or producer cells by lysing the cells. Lysis of engineered rAAV packaging and/or producer cells can be accomplished by methods that chemically or enzymatically treat the cells in order to release infectious viral particles. These methods include the use of nucleases such as benzonase or DNAse, proteases such as trypsin, or detergents or surfactants. Physical disruption, such as homogenization or grinding, or the application of pressure via a microfluidizer pressure cell, or freeze-thaw cycles may also be used. In certain embodiments, lysates from the engineered rAAV packaging and/or producer cells can be used to harvest rAAV particles.

In certain embodiments, cell culture supernatant may be collected from engineered rAAV packaging and/or producer cells without the need for cell lysis. In certain embodiments of the present disclosure, the engineered rAAV packaging and/or producer cells secrete rAAV particles that can be collected from the cell culture supernatant without the need for cell lysis. In certain embodiments, the engineered rAAV packaging and/or producer cell line has a higher rAAV titer than that of a control parental cell line such that more rAAV is harvested from the engineered rAAV packaging and/or producer cell line compared to the control parental cell line.

After harvesting rAAV particles, it may be necessary to purify the sample containing rAAV, to remove, for example, the cellular debris resulting from cell lysis. Methods of minimal purification of AAV particles are known in the art. Two exemplary purification methods are Cesium chloride (CsCl)- and iodixanol-based density gradient purification. Both methods are described in Strobel et al., Human Gene Therapy Methods., 26(4): 147-157 (2015). Minimal purification can also be accomplished using affinity chromatography using, for example, AVB Sepharose affinity resin (GE Healthcare Bio-Sciences AB, Uppsala, Sweden). Methods of AAV purification using AVB Sepharose affinity resin are described in, for example, Wang et al., Mol Ther Methods Clin Dev., 2:15040 (2015). Following purification, rAAV particles may be filtered and stored at $\leq -60°$ C.

In certain embodiments, the present disclosure provides a method of harvesting rAAV particles that are produced from an engineered rAAV packaging cell line after the cells have been co-infected with two different adenoviruses.

In certain embodiments, the present disclosure provides a method of harvesting rAAV particles that are produced after infection of a rAAV producer cell line generated from an engineered rAAV packaging cell line.

In certain embodiments, the present disclosure provides a method of harvesting rAAV particles that are produced after infection of an engineered rAAV producer cell line with a helper virus.

Quantification of rAAV Particles

Quantification of rAAV particles is complicated by the fact that AAV infection does not result in cytopathic effects in vitro, and therefore plaque assays cannot be used to determine infectious titers. rAAV particles can be quantified using a number of methods, however, including quantitative polymerase chain reaction (qPCR) (Clark et al., Hum. Gene Ther. 10, 1031-1039 (1999)), dot-blot hybridization (Samulski et al., J. Virol. 63, 3822-3828 (1989)), and by optical density of highly purified vector preparations (Sommer et al., Mol. Ther. 7, 122-128 (2003)). DNase-resistant particles (DRP) can be quantified by real-time quantitative gene expression reduced polymerase chain reaction (qPCR) (DRP-qPCR) in a thermocycler (for example, an iCycler iQ 96-well block format thermocycler (Bio-Rad, Hercules, Calif.)). Samples containing rAAV particles can be incubated in the presence of DNase I (100 U/ml; Promega, Madison, Wis.) at 37° C. for 60 min, followed by proteinase K (Invitrogen, Carlsbad, Calif.) digestion (10 U/ml) at 50° C. for 60 min, and then denatured at 95° C. for 30 min. The primer-probe set used should be specific to a non-native portion of the rAAV vector genome, for example, the poly(A) sequence of the protein of interest. The PCR product can be amplified using any appropriate set of cycling parameters, based on the length and composition of the primers, probe, and amplified sequence. Alternative protocols are disclosed in, for example, Lock et al., Human Gene Therapy Methods 25(2): 115-125 (2014).

Viral genome amplification can also be measured using qPCR techniques similar to those described above. However, in order to quantify total genome amplification within producer cells, only intracellular samples are collected and the samples are not treated with DNase I in order to measure both packaged and unpackaged viral genomes. Viral genome amplification may be calculated on a per-host-cell basis by concomitantly measuring a host cell housekeeping gene, for example, RNase P.

The infectivity of rAAV particles can be determined using a TCID50 (tissue culture infectious dose at 50%) assay, as described for example in Zhen et al., Human Gene Therapy 15:709-715 (2004). In this assay, rAAV vector particles are serially diluted and used to co-infect a Rep/Cap-expressing cell line along with AV particles in 96-well plates. 48 hours post-infection, total cellular DNA from infected and control wells is extracted. rAAV vector replication is then measured using qPCR with transgene-specific probe and primers. TCID50 infectivity per milliliter (TCID50/ml) is calculated with the Karber equation, using the ratios of wells positive for AAV at 10-fold serial dilutions.

Therapeutic Applications

The rAAV produced from the engineered rAAV packaging and/or producer cell lines described herein can be used, e.g., for gene therapy in mammals. The rAAV produced from the engineered cells described herein can be used for ex vivo and/or in vivo gene therapy applications. The rAAV produced from the engineered cells described herein can be used, e.g., to deliver small molecules (e.g., siRNAs or sgRNAs), peptides, and/or proteins.

In some embodiments, the rAAV generated from the engineered cell lines described herein can be used to treat a disease or a disorder in a human subject in need. In certain embodiments, the rAAV generated from the engineered cell lines described herein can be administered in conjunction with a pharmaceutically acceptable carrier.

Any suitable method or route can be used to administer a rAAV or a rAAV-containing composition produced from the engineered packaging and/or producer cell lines described herein. Routes of administration include, for example, systemic, oral, inhalation, intranasal, intratracheal, intraarterial, intraocular, intravenous, intramuscular, subcutaneous, intradermal, and other parenteral routes of administration. In some embodiments, the rAAV or a composition comprising a rAAV produced from the engineered packaging and/or producer cell line is administered intravenously.

Practice of the disclosure will be more fully understood from the foregoing examples, which are presented herein for illustrative purposes only, and should not be construed as limiting the disclosure in any way.

EXAMPLES

Figure 2A:
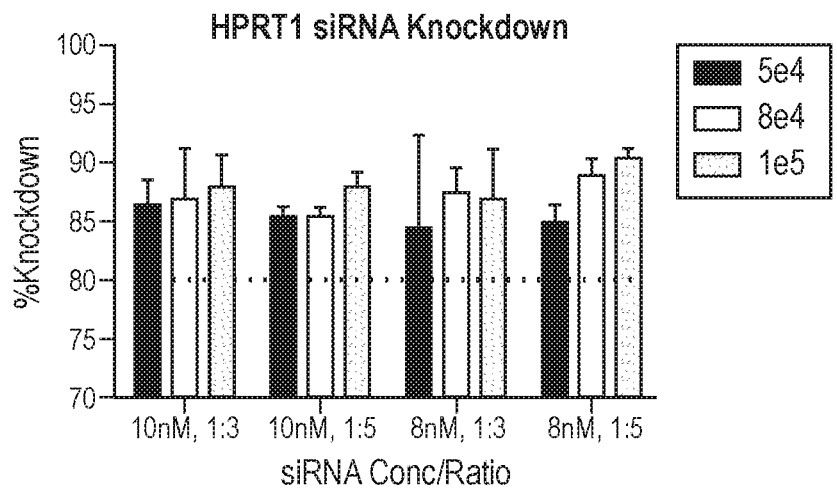
FIGS. 2A-2D show experimental data generated from the optimization and development of HPRT1 siRNA knockdown experiments.
Figure 2B:
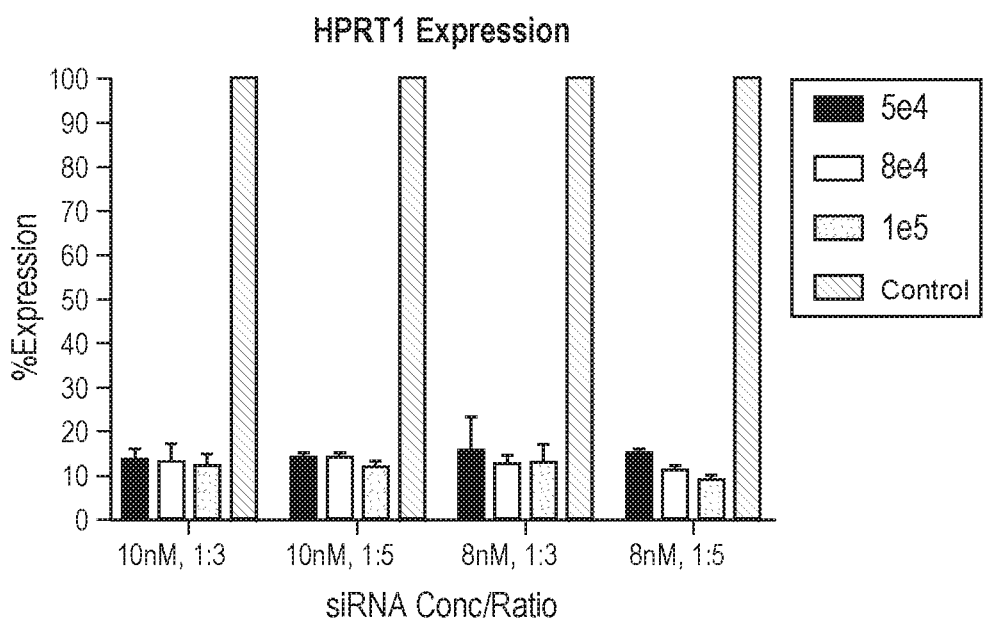
Figure 2C:
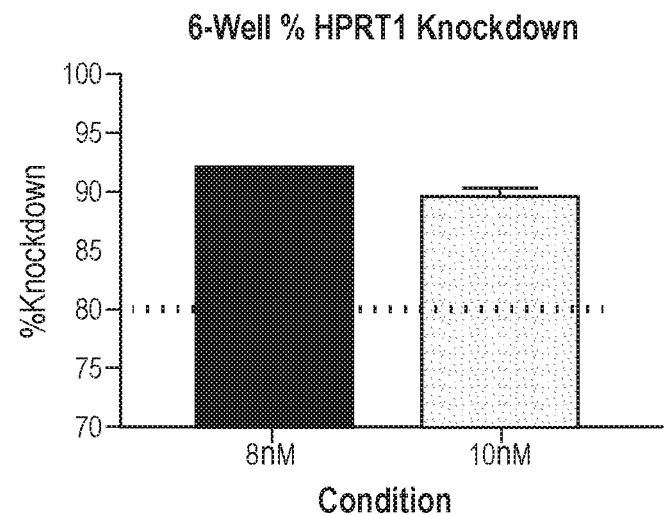
Figure 2D:
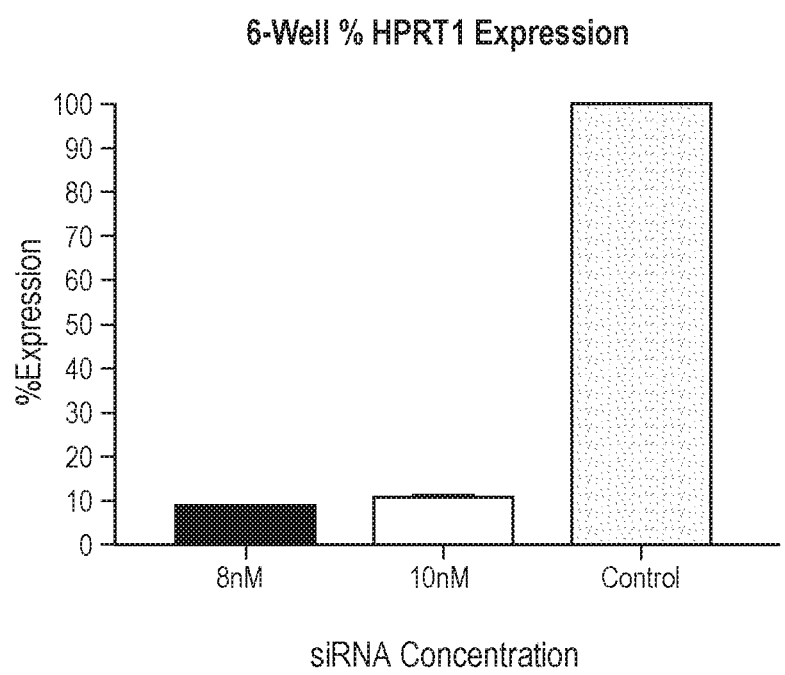

Example 1: Development of Knockdown Protocols siRNA knockdown experiments were optimized and developed for 6-well and 24-well formats by knocking down the house keeping gene, HPRT1. The experiments performed in 24-wells were evaluated based on numerous factors such as seeding density, cell culture conditions (e.g., percent carbon dioxide ($CO_2$), percent of Fetal Bovine Serum (FBS)), ratio between transfection reagent (Lipofectamine® RNAiMax) and siRNA ("Ratio"), incubation time, and siRNA concentration. Commercially available siRNAs designed for HPRT1 gene knockdown were used to optimize the experimental conditions. HeLa producer cells were transfected with varying concentrations of siRNA using Lipofectamine® RNAiMax according to the manufacturer's instructions. Percent reduction of HPRT1 expression was determined by real time PCR. The optimized 24-well siRNA knockdown method was capable of knocking down the highly expressed gene, HPRT1, by more than 80% compared to baseline control. As shown in FIG. 2A-D, cells seeded at $1 \times 10^5$ cells per well, 1:5 ratio between transfection reagent and siRNA, 8 nM of siRNA showed the highest knockdown efficiency. FIG. 2A shows the effect of varying siRNA concentrations/ratios used on the percent knockdown of HIPRT1. FIG. 2B shows the effect of varying siRNA concentrations/ratios on the percent expression of HPRT1. For the 6-well protocol optimization, two different siRNA concentrations were tested. Seeding densities of $5 \times 10^4$, $8 \times 10^4$, and $1 \times 10^5$ were tested for the data plotted in FIGS. 2A and 2B. FIG. 2C shows the effect of varying siRNA concentrations on the percent knockdown of HPRT1. FIG. 2D shows the effect of varying concentrations of siRNA on the percent expression of HPRT1. All experiments were performed in triplicate.

Example 2: RNA Sequencing

Eight three-liter bioreactors were run at supplemented and non-supplemented production conditions across two different HeLaS3 producer cell lines. Two additional bioreactors were run without Adenovirus5 (Ad5) as uninfected controls. Table 3 lists details on bioreactor conditions and production levels.

TABLE 3

Bioreactor conditions and production levels.

| Condition | Cell Line | Production Level | Seeding Density | Base Media | Supplement(s) | Ad5 |
|---|---|---|---|---|---|---|
| 1 | 21C5 | No production control | $0.7 \times 10^6$ cells/mL | 90% DMEM/ 10% Ex-Cell | – | None |
| 2 | 21C5 | Low | $0.7 \times 10^6$ cells/mL | 90% DMEM/ 10% Ex-Cell | – | 200 MOI |
| 3 | 21C5 | Low | $0.7 \times 10^6$ cells/mL | 90% DMEM/ 10% Ex-Cell | – | 200 MOI |
| 4 | 21C5 | Medium | $0.7 \times 10^6$ cells/mL | 90% DMEM/ 10% Ex-Cell | + | 200 MOI |
| 5 | 21C5 | Medium | $0.7 \times 10^6$ cells/mL | 90% DMEM/ 10% Ex-Cell | + | 200 MOI |
| 6 | 21C5 | High | $0.7 \times 10^6$ cells/mL | 90% DMEM/ 10% Ex-Cell | + | 200 MOI |
| 7 | 2B6 | No production control | $0.7 \times 10^6$ cells/mL | 90% DMEM/ 10% Ex-Cell | – | None |
| 8 | 2B6 | Low | $0.7 \times 10^6$ cells/mL | 90% DMEM/ 10% Ex-Cell | – | 200 MOI |
| 9 | 2B6 | Medium | $0.7 \times 10^6$ cells/mL | 90% DMEM/ 10% Ex-Cell | + | 200 MOI |
| 10 | 2B6 | High | $0.7 \times 10^6$ cells/mL | 90% DMEM/ 10% Ex-Cell | + | 200 MOI |

Abbreviations used in Table 3: addition of one or more supplements is indicated by (+); absence of one or more supplements is indicated by (−); MOI—Multiplicity of infection.

Thirty hours post infection with Ad5, samples were pulled for RNA-Seq. Samples were washed once with PBS and cell pellets were stored at −80° C. until ready for shipment. RNA extraction and cDNA synthesis of extracted RNA were performed by methods well known in the art. Prior to sequencing, library preparation was done using commercially available RNA-Seq library preparation kits. RNA sequencing was done using commercially available Illumina sequencing platforms. Reads generated were mapped to human genome, Ad5 genome, and AAV2 genome using mapping methods well known in the art. Any reads mapped to Ad5 genome were discarded. Another round of sequencing was performed to enrich for reads mapped to the human genome. Differential analyses were performed using the data generated by RNA Sequencing (see Table 4).

TABLE 4

Differential analyses

| Differential analysis # | Control Condition | Experimental Condition |
|---|---|---|
| 1 | PCL1; No Production | PCL1*; Production (N.S.) |
| 2 | PCL1; No Production | PCL2; No Production |
| 3 | PCL1; No Production | PCL1; Production (S) |
| 4 | PCL1; Production (N.S.) | PCL1; Production (S) |
| 5 | PCL1; Production (N.S.) | PCL1; Production (S) |
| 6 | PCL1; Production (N.S.) | PCL2; Production (N.S.) |
| 7 | PCL2; No Production | PCL2; Production (N.S.) |
| 8 | PCL2; No Production | PCL2; Production (S) |
| 9 | PCL2; No Production | PCL2; Production (S) |
| 10 | PCL1; Production (S) | PCL2; Production (S) |
| 11 | PCL2; Production (S) | PCL2; Production (S) |
| 12 | PCL1; Production (S) | PCL1; Production (S) |
| 13 | PCL1; Production (S) | PCL1; Production (S) |

*PCL1—producer cell line 1; PCL2—producer cell line 2; No Production—uninfected control cells; Production (N.S.)—Ad5 infected cells cultured under non-supplemented conditions; Production (S)—Ad5 infected cells cultured under supplemented conditions.

In this example, differential expression analysis was calculated as the log fold change (LogFC) in mRNA levels of the experimental condition compared to the control condition. Upregulated genes were expressed as a positive LogFC and downregulated genes were expressed as a negative LogFC. Differentially expressed genes having a p-value≤0.05 were considered statistically significant. Within each differential analysis hundreds to thousands of genes were significantly up or down regulated. A filtering criteria was established (see, e.g., FIG. 6) and applied to reduce the data set down to a manageable number of genes for evaluation. Gene sets were aligned and moved to the filter criteria as described in Example 6.

Example 3: Validation of Results Obtained from RNA Sequencing by RT-qPCR

Figure 3A:
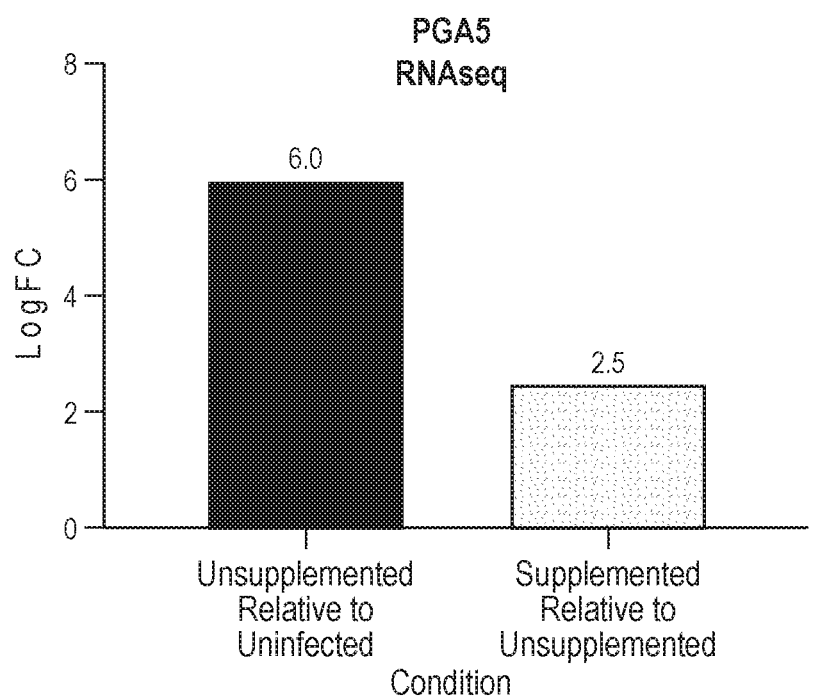
FIGS. 3A-3B show the log fold change values in gene expression obtained from bioinformatic analysis of RNA-Seq data for PGA5 (FIG. 3A) and SPANXN3 (FIG. 3B), represented as log fold change in gene expression in cells cultured in unsupplemented cell culture medium relative to uninfected cells (cells not infected with a helper virus), and log fold change in gene expression in cells cultured in supplemented cell culture medium relative to unsupplemented cell culture medium.
Figure 3B:
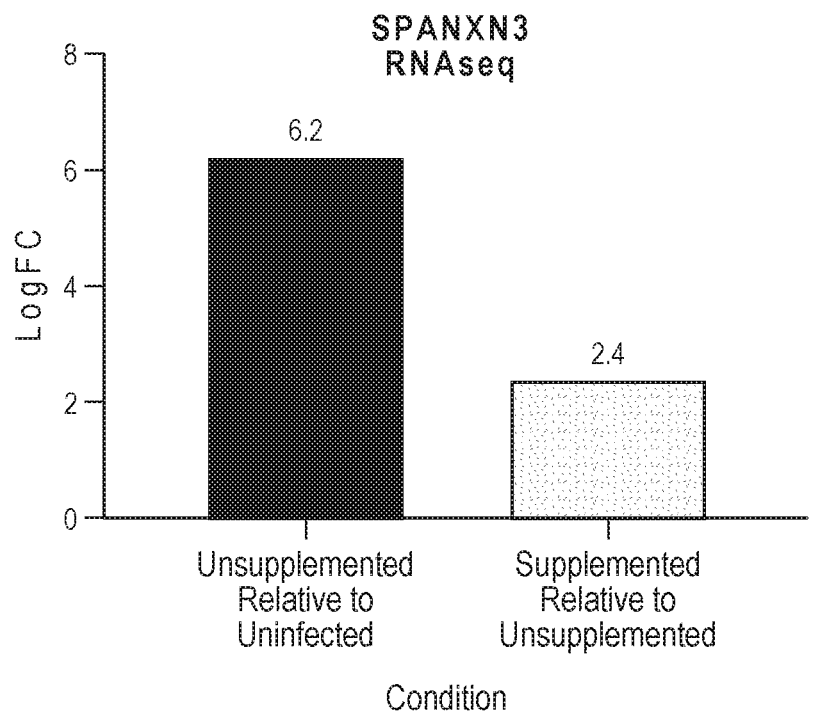

A small set of genes were selected for validation of RNA Sequencing data. RNA-Seq results were confirmed using an RT-qPCR assay following methods well-known in the art. The ΔΔCt method was used to analyze data. RT-qPCR independently confirmed the trends observed in the RNA-Seq data. FIG. 3A-B shows the log fold change values in gene expression obtained from bioinformatic analysis of RNA-Seq data for PGA5 (FIG. 3A) and SPANXN3 (FIG. 3B). X-axis shows the conditions (supplemented (differential analysis #5 as described in Table 4) versus non-supplemented (differential analysis #1 as described in Table 4)) in which the producer cell lines were grown and y-axis shows the log fold change (LogFC) in gene expression. Log fold change in PGA5 (FIG. 3A) and SPANXN3 (FIG. 3B) expression in cells cultured in unsupplemented cell culture medium is plotted relative to the corresponding gene expression in uninfected cells (cells not infected with a helper virus). Log fold change in PGA5 (FIG. 3A) and SPANXN3 (FIG. 3B) expression in cells cultured in supplemented cell culture medium is plotted relative to the corresponding gene expression in cells cultured in unsupplemented cell culture medium.

Figure 3C:
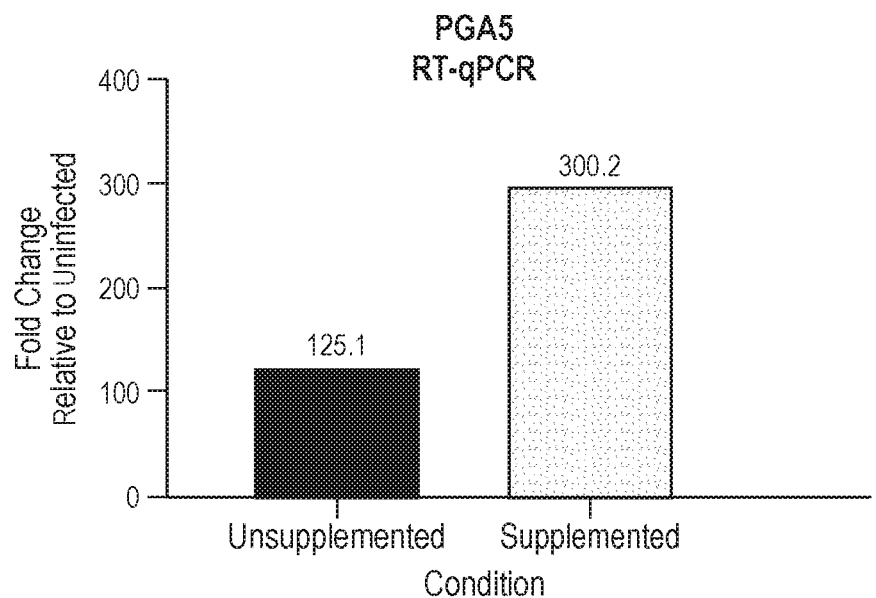
FIGS. 3C-3D show RT-qPCR fold change values in the expression of PGA5 (FIG. 3C) and SPANXN3 (FIG. 3D) in cells cultured in unsupplemented and supplemented cell culture medium, relative to uninfected cells.
Figure 3D:
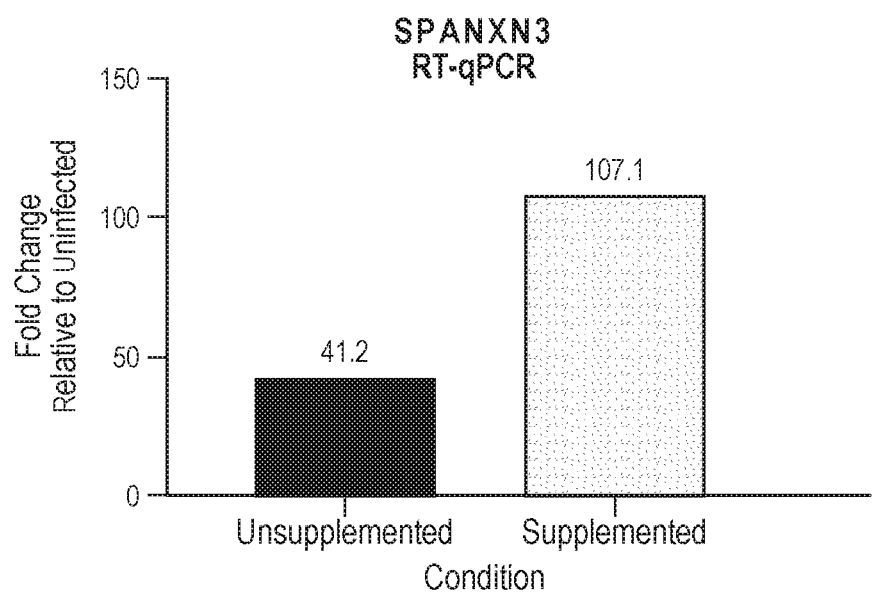

PGA5 and SPANXN3 gene expression in producer cell lines grown under supplemented and non-supplemented conditions was also evaluated by RT-qPCR by using methods well-known in the art. FIG. 3C-D show RT-qPCR fold change values in the expression of PGA5 (FIG. 3C) and SPANXN3 (FIG. 3D) in cells cultured in unsupplemented and supplemented cell culture medium, relative to uninfected cells (cells not infected with a helper virus). FIG. 3A-D show that data obtained from qPCR and RNA Sequencing follow the same trend.

Figure 4A:
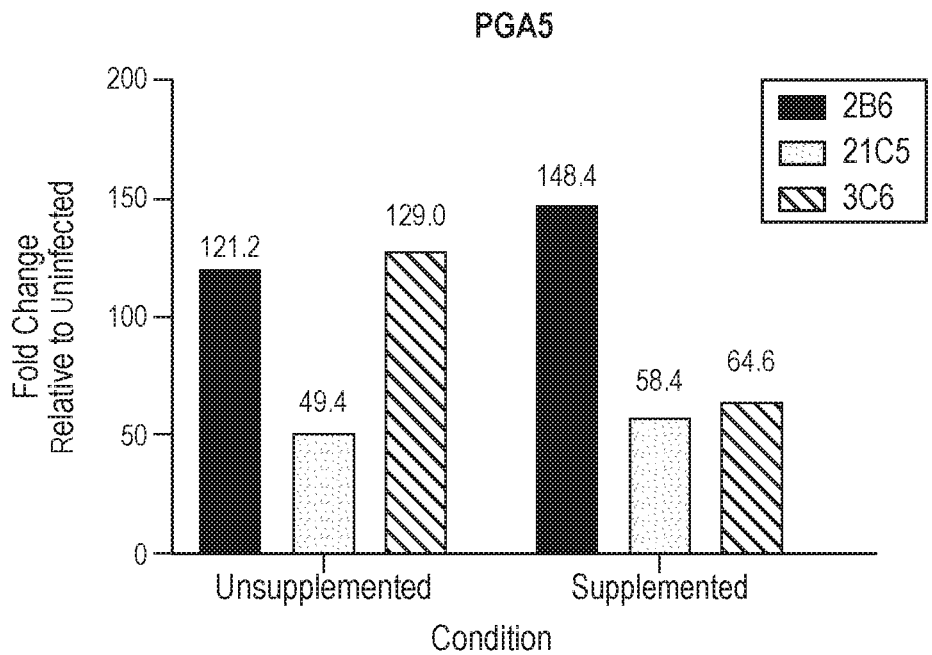
FIGS. 4A-4B show the fold change values in PGA5 (FIG. 4A) and SPANXN3 (FIG. 4B) expression in producer cell line clones cultured in unsupplemented cell culture medium and supplemented cell culture medium relative to uninfected cells (cells not infected with a helper virus), as determined from RT-qPCR. 21C5, 3C6, 2B6 represent different clones of the HeLa producer cell line.
Figure 4B:
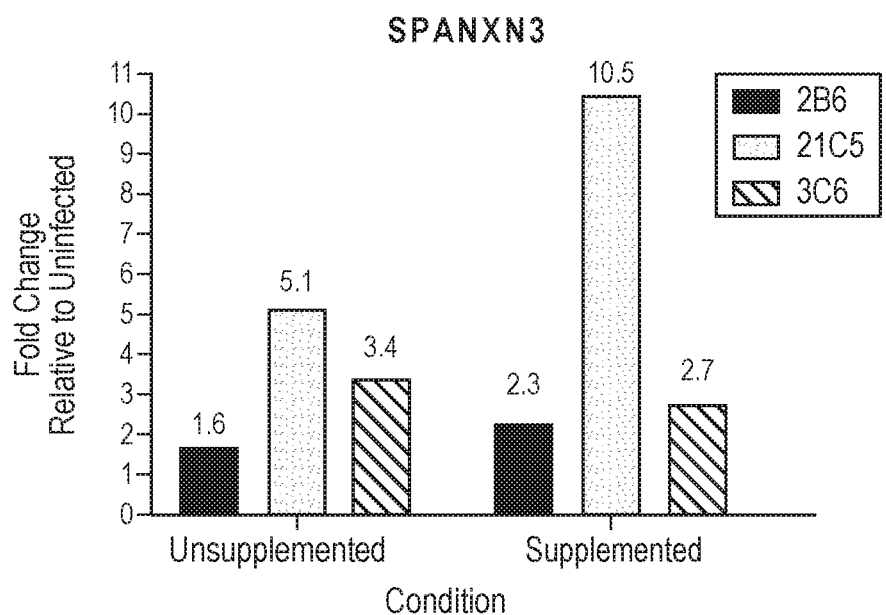
Figure 4C:
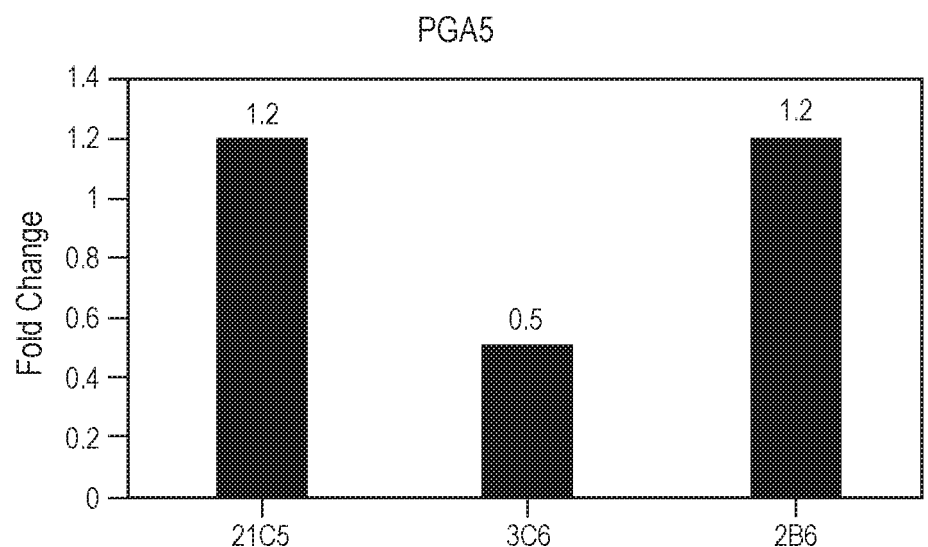
FIGS. 4C-4D show relative fold increase in PGA5 (FIG. 4C) and SPANXN3 (FIG. 4D) expression in producer cell line clones 21C5, 3C6, 2B6 cultured in supplemented cell culture medium compared to the clones cultured in non-supplemented cell culture medium.
Figure 4D:
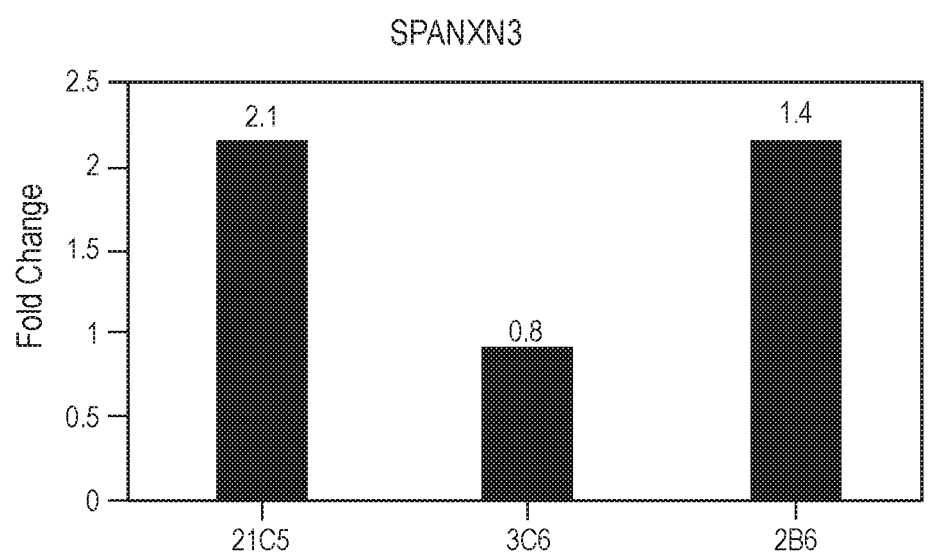

Example 4: Validation of Results Obtained from RNA Sequencing by RT-qPCR in Different Clones of a Producer Cell Line RNA Sequencing results were further validated by running RT-qPCR experiments on RNA extracted from different clones of a HeLa S3 producer cell line. FIG. 4A-B show the fold change values in PGA5 (FIG. 4A) and SPANXN3 (FIG. 4B) expression in producer cell line clones cultured in unsupplemented cell culture medium and supplemented cell culture medium relative to uninfected cells (cells not infected with a helper virus), as determined from RT-qPCR. 21C5, 3C6, and 2B6 represent different clones of the HeLa producer cell line. FIG. 4C-D show relative fold increase in PGA5 (FIG. 4C) and SPANXN3 (FIG. 4D) expression in producer cell line clones 21C5, 3C6, and 2B6 cultured in supplemented cell culture medium compared to the clones cultured in non-supplemented cell culture medium. These results further validate bioinformatic RNA Sequencing and RT-qPCR data described in Example 3.

Example 5: Effect of Gene Knockdown on rAAV Titer

Knockdown experiments were performed by individually knocking down genes in HeLa producer cell lines based on the optimized protocol discussed in Example 1. siRNA nucleotide sequences were designed for each gene (see Table 1).

Figure 5A:
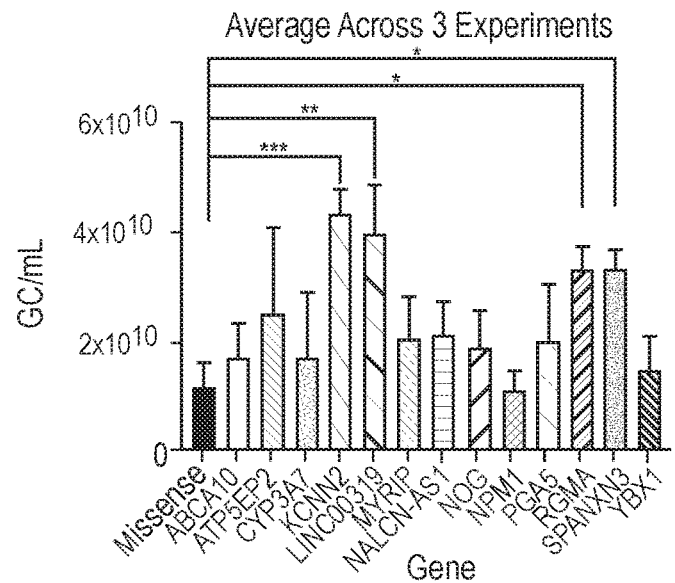
FIGS. 5A-5F show the effect of reducing expression of individual genes in different producer cell lines on rAAV titers. The figures show the titers of produced rAAV in genome copies (GC) per milliliters (mL) for producer cell line #1 (FIG. 5A), producer cell line #2 (FIG. 5B), and producer cell line #3 (FIG. 5C).
Figure 5B:
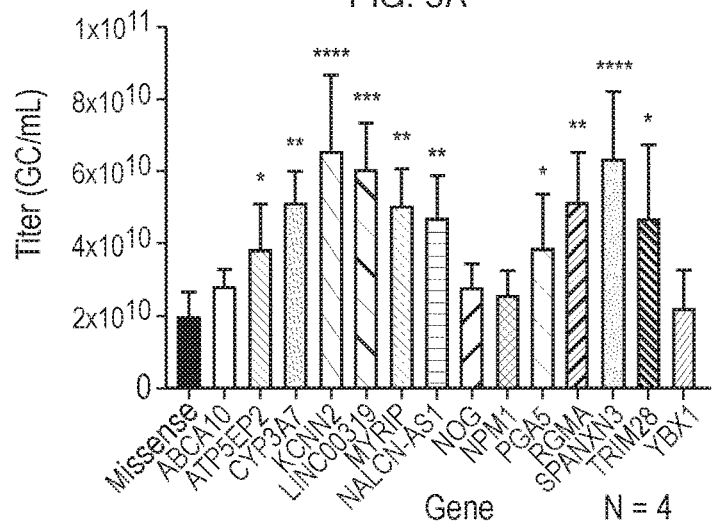
Figure 5C:
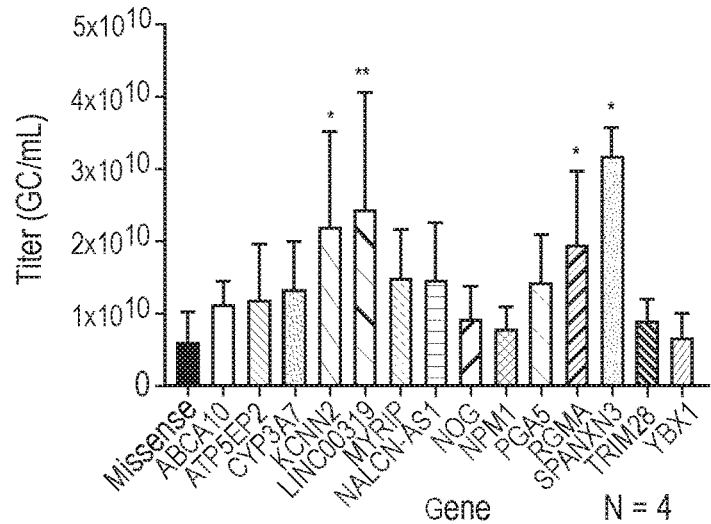
Figure 5D:
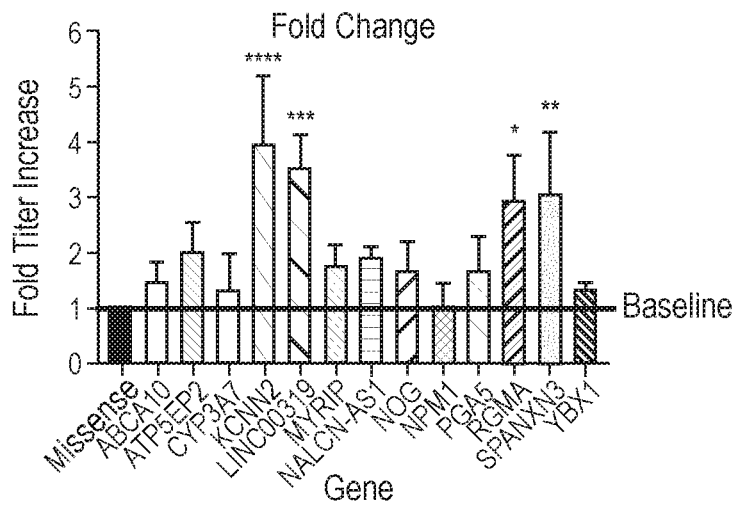
Figure 5E:
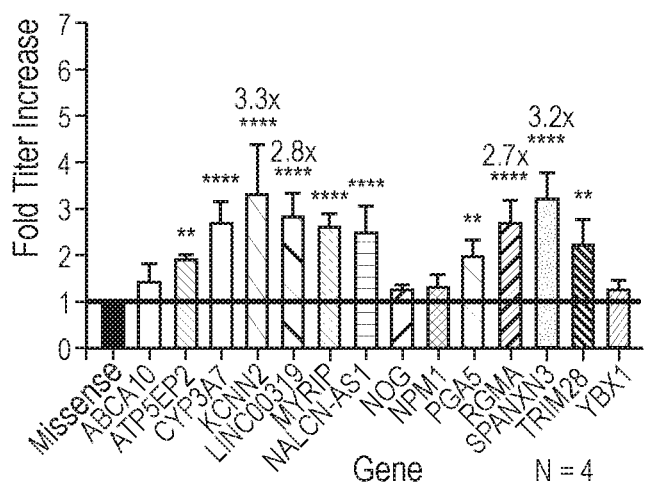
Figure 5F:
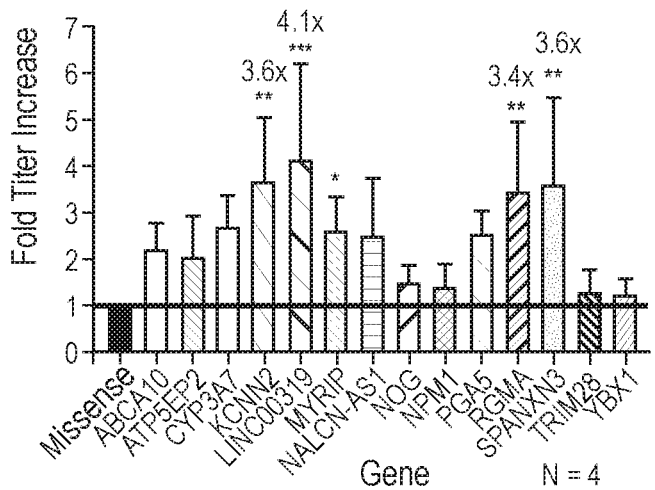

The condition settled upon as a $1\times10^5$ seeding density with 8 nM siRNA and a siRNA:RNAiMAX ratio of 1:5. AAV production was induced 24 hours post reduction of expression of genes, and rAAV was harvested 72 hours post infection. Titer was determined for each sample and compared to a non-targeting missense siRNA control. This experiment was performed independently three times, results were averaged, and statistical analysis was performed. FIGS. 5A-5C show the result of siRNA of individual genes in producer cell lines 1-3, respectively, on absolute rAAV titer (GC/mL; GC=genome copies). FIGS. 5D-5F show the fold increase on rAAV titer by siRNA of individual genes in different producer cell lines 1-3, respectively.

As shown in FIGS. 5A-5F, reduction of expression of KCNN2, LINC00319, RGMA, or SPANXN3 in producer cell lines resulted in statistically significant 2-4-fold higher rAAV titers over missense control. Across three producer cell lines, these four genes show a statistically relevant positive impact on titer when knocked down. These results indicate that these genes are excellent targets for more permanent modifications, such as CRISPR/Cas9 knockouts.

Example 6: Gene Filtering Methodology

For filter 1, the genes from differential analysis 1 and 7 (as described in Table 3) were aligned. The differential analysis for 1 and 7 defined genes that are up or down-regulated upon the addition of adenovirus 5 in non-supplemented conditions. Analysis 1 looked at the cells from 21C5 producer cell line (producer cell line 1, PCL1). Analysis 7 looked at the cells from 2B6 (producer cell line 2, PCL2). List of genes after this filter 1 identified genes that were not cell line specific, and this alignment provided a total of 9149 genes that were in common between the two producer cell lines.

For filter 2, the genes from filter 1 were the aligned with genes present in differential analysis 5. Analysis 5 looked at genes that were up and down regulated in cells from 21C5 producer cell line (PCL1) in supplemented conditions compared to non-supplemented conditions. The purpose of this differential analysis was to define the effects of production under supplemented conditions in regards to production under non-supplemented conditions. The purpose of aligning the gene set from filter 1 with differential analysis 5 was to identify genes in the improved productivity conditions that are 1) not a byproduct of the improved production conditions 2) potentially relevant for two different cell lines. After alignment, 374 genes were moved forward.

For filter 3, only genes that had a large Log Fc threshold of >2 Log FC± were moved forward. This was done to ensure a high level of up/down regulation in the genes being moved forward, and to give a degree of confidence that the genes selected were not artifacts of the RNA-Seq. After the filter, 77 genes were moved forward.

Figure 6:
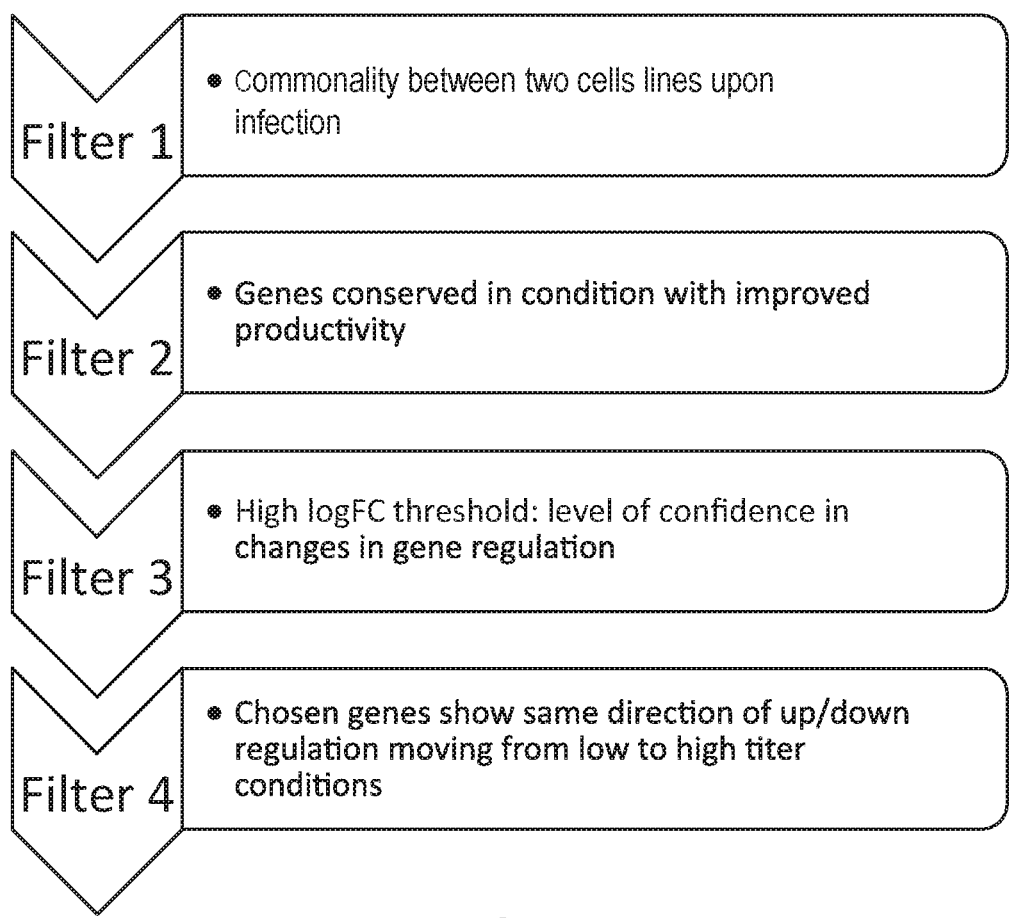
FIG. 6 is an illustrative flow-chart showing an exemplary gene filtering methodology.

For filter 4, only genes that showed both up-regulation in differential analysis 1 and differential analysis 5 or down-regulation in differential analysis 1 and differential analysis 5 were kept. For example, one of the 77 genes must show up-regulation from differential analysis 1 and further up-regulation in differential analysis 5 or down-regulation in differential analysis 1 and further down-regulation in differential analysis 5. The purpose of this filter was to ensure that, for the genes being evaluated, high titer conditions were not having an antagonistic effect on that particular gene's regulation compared to low titer conditions. After the filter eleven genes were left to be evaluated. An illustrative flow-chart showing an exemplary gene filtering methodology is shown in FIG. 6 (abbreviation used: LogFC=Log fold change).

Table 5 provides Log 2FC data from each comparison during the process of filtering down important genes for productivity.

TABLE 5

Log2FC data

| Gene | Differential Analysis 7 | Differential Analysis 1 | Differential Analysis 5 |
|---|---|---|---|
| ATP5EP2 | 2.409 | −1.1 | −7.511 |
| LINC00319 | −4.382 | −1.432 | −6.58 |
| CYP3A7 | −8.018 | −3.149 | −2.814 |
| ABCA10 | −4.257 | −2.025 | −3.131 |
| NOG | −5.585 | −1.468 | −2.814 |
| SPANXN3 | 4.99 | 6.238 | 2.423 |
| PGA5 | 8.153 | 6.019 | 2.519 |
| MYRIP | 2.045 | 2.771 | 2.175 |
| KCNN2 | 3.656 | 2.807 | 2.066 |
| NALCN-AS1 | 4.558 | 2.639 | 2.024 |
| RGMA | 2.764 | 2.303 | 2.03 |

Example 7: Gene Knockout of KCNN2

In this example, two existing, highly optimized monoclonal HeLa producer cell lines (PCLs)—2H5 and 7B12—were genetically modified to knockout the KCNN2 gene (previously identified in the RNA-seq screen described herein), which encodes a calcium-activated potassium channel protein, SK2.

KCNN2 was knocked out in 2H5 or 7B12 HeLa cells using an eGFP selectable marker. Suspected KCNN2 knockouts were enriched for eGFP expression and seeded in 96-well plates. Cell colonies were allowed to form, genomic DNA was harvested, and PCR was performed to amplify the region containing the knockout. The PCR product was Sanger sequenced and the sequencing files were analyzed for the presence of insertion/deletions. 2H5 and 7B12 clones with a high likelihood of knockout were scaled-up for further testing.

Figure 8A:
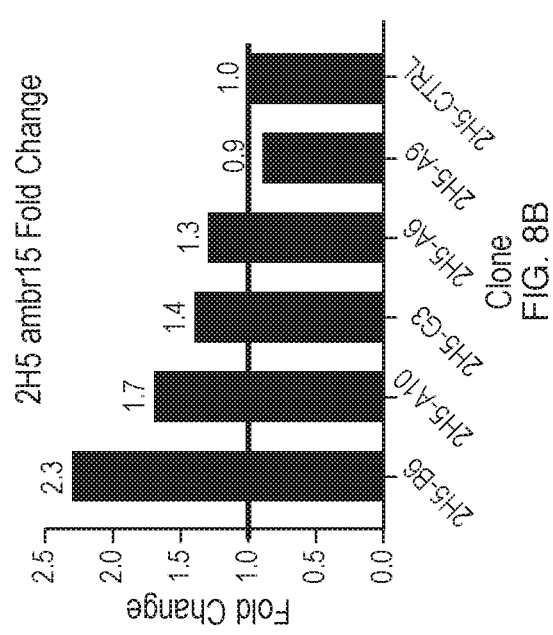
FIG. 8A shows the Ambr® 15 titers of the top five 2H5 knockout clones. Titer is reported as genome copies per mL. The control sample is unmodified 2H5.
Figure 8B:
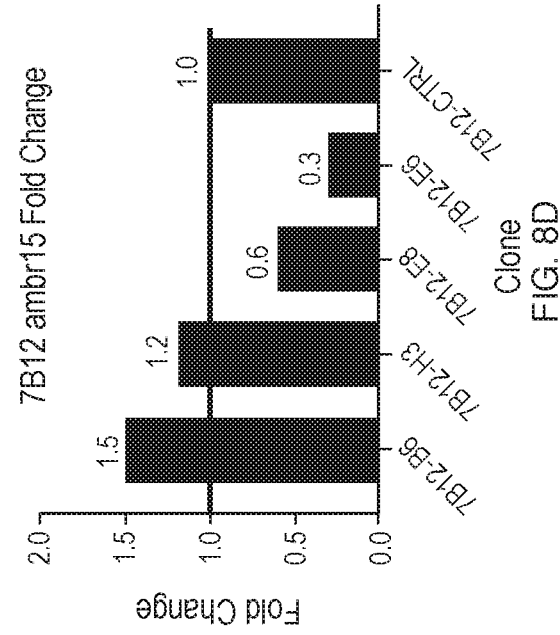
FIG. 8B shows the fold change in titer compared to the 2H5 control. 2H5 titer was set to 1 and other titers are displayed as the fold increase above the 2H5 control.
Figure 8C:
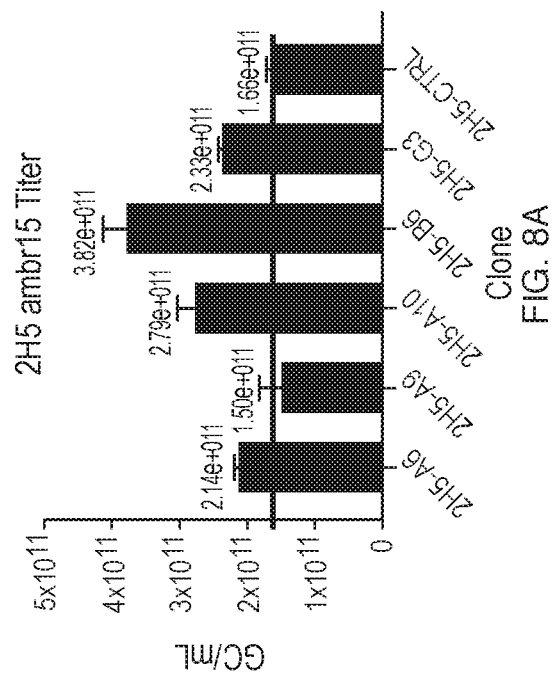
FIG. 8C shows the Ambr® 15 titers of the top four 7B12 knockout clones. Titer is reported as genome copies per mL. The control sample is unmodified 7B12.
Figure 8D:
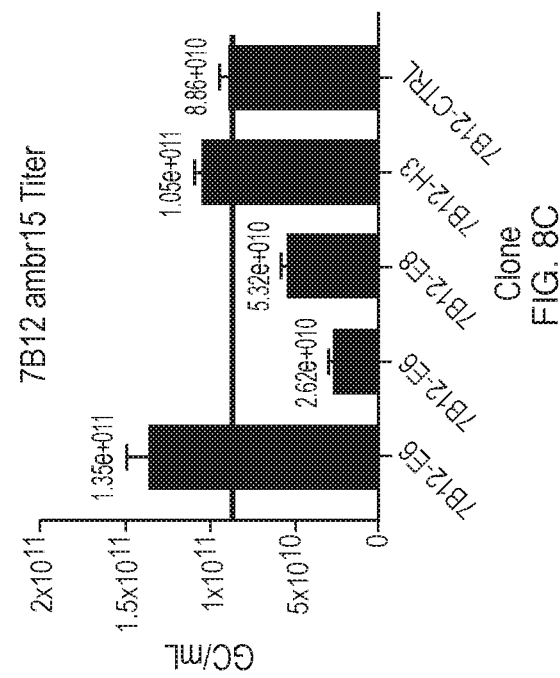
FIG. 8D shows the fold change in titer compared to the 7B12 control. 7B12 titer was set to 1 and other titers are displayed as the fold increase above the 7B12 control.

Top clones were transferred into serum free, suspension culture. Clone productivity compared to the parental line was assessed through a 24 deep well rAAV production. Clones were seeded at $2\times10^5$ cells/mL in 3 mL of culture and infected with Ad5 at a multiplicity of infection (MOI) of 50. Four days post infection, rAAV was harvested and assessed for titer. Fold increase in titer was normalized to the parental control. The best clones displayed 1.5-2.7 fold increases in titer compared to the control samples. 2H5 titers ranged from $2.46\times10^9$-$4.98\times10^{10}$ GC/mL (FIG. 7A). When titers were normalized to the parental control, fold increases were seen ranging from 1.2-2.7 fold (FIG. 7B). 7B12 titers ranged from $4.33\times10^8$-$1.88\times10^{10}$ GC/mL (FIG. 7C). When titers were normalized to the parental control, fold increases were seen ranging from 1.5-2.6 fold (FIG. 7D). Clones with a minimum of 1.5 fold increase were then scaled into shake flask culture and inoculated into the Ambr® 15 for high seeding density, supplemented rAAV production. Cells were seeded at $1.5\times10^6$ cells/mL and infected with Ad5 at an MOI of 50. rAAV was harvested four days post infection and assessed for titer. Fold increase in titer was normalized to the parental control. The best clones displayed 1.5-2.3 fold increases in titer compared to the control samples. 2H5 titers ranged from $1.5\times10^{11}$-$3.82\times10^{11}$ GC/mL (FIG. 8A). When titers were normalized to the parental control, fold increases were seen ranging from 1.3-2.3 fold (FIG. 8B). 7B12 titers ranged from $2.62\times10^{10}$-$1.35\times10^{11}$ GC/mL (FIG. 8C). When titers were normalized to the parental control, fold increases were seen ranging from 1.2-1.5 fold (FIG. 8D).

These data establish that reducing or eliminating the expression of one or more genes described herein (e.g., via gene knockout) in AAV-producing cells can be employed to increase the production of rAAV from engineered cells.

Example 8: Multi-Combinatorial siRNA Knockdowns

In this example, multi-combinational knockdown of genes previously identified in the RNA-seq screen described herein using siRNA was performed to determine if targeting multiple genes simultaneously would produce an additive effect on titer.

Multi-combinational knockdowns were performed using a modification of the methods described in Example 5. Briefly, cells were transfected using 8 nM of each siRNA and maintaining a ratio of siRNA:RNAiMAX of 1:5. AAV production was induced 24 hours post reduction of expression of genes, and rAAV was harvested 72 hours post infection. Titer was determined for each sample and compared to a non-targeting missense siRNA control.

Figure 9B:
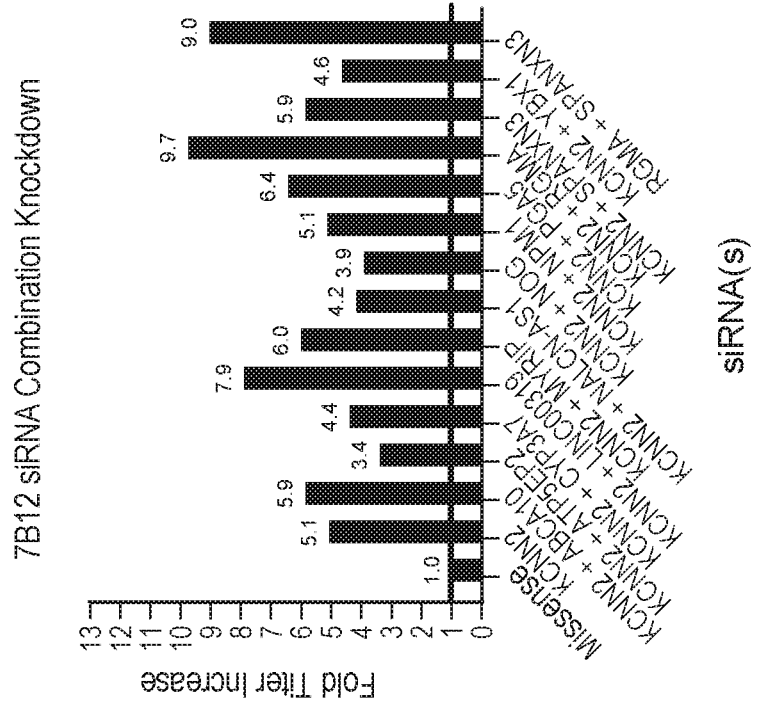
FIGS. 9A-9B show the effect on rAAV titer generated by reducing expression of various gene combinations in two producer cell lines. The figures show fold change in rAAV titer compared to a control treated with missense siRNA.
Figure 9A:
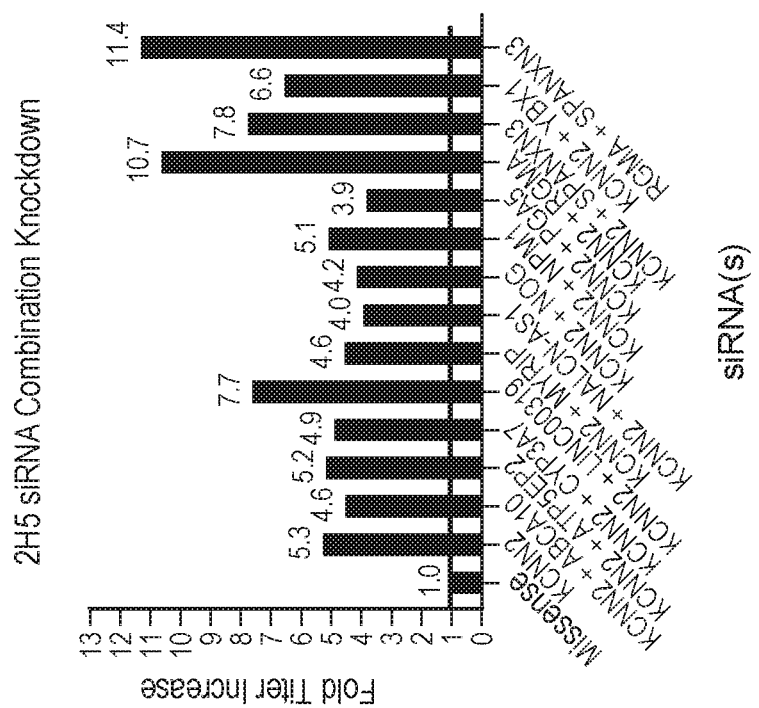

In this example, KCNN2 was knocked down in combination with the panel of other siRNAs previously described. Additionally, RGMA and SPANXN3 were knocked down in combination with each other. In 2H5, combination knockdowns displayed a range of titer increases from 4.6-11.4 fold compared to a missense control (FIG. 9A). In 7B12, combination knockdowns displayed a range of titer increases 3.4-9.7 fold compared to the missense control (FIG. 9B). Every combination displayed an increase in titer; however, not all combinations were an improvement over knocking down KCNN2 alone. KCNN2 knockdown led to a 5.3 fold increase in 2H5 (FIG. 9A) and a 5.1 fold increase in 7B12 (FIG. 9B).

These data establish that additional increases in the production of rAAV can be gained through direct targeting of multiple genomic regions in established high rAAV titer producing monoclonal PCLs.

NUMBERED EMBODIMENTS

1. A recombinant adeno-associated virus (rAAV) packaging and/or producer cell line comprising cells in which the expression of ATP5EP2, LINC00319, CYP3A7, ABCA10, NOG, RGMA, SPANXN3, PGA5, MYRIP, KCNN2, and/or NALCN-AS1 is reduced compared to control parental cells.
2. The packaging and/or producer cell line according to embodiment 1, comprising cells in which expression of KCNN2, LINC00319, RGMA, and SPANXN3 is reduced compared to control parental cells.
3. The packaging and/or producer cell line according to embodiment 1 or 2, wherein the expression is reduced using a nuclease, a double stranded RNA (dsRNA), a small interfering RNA (siRNA), a small hairpin RNA (shRNA), a microRNA (miRNA), or an antisense RNA oligonucleotide (ASO).
4. The packaging and/or producer cell line according to any one of embodiment 1-3, wherein the expression is reduced with an siRNA comprising a nucleotide sequence selected from any one of SEQ ID NOs: 1-11.
5. The packaging and/or producer cell line according to embodiment 4, wherein expression of ATP5EP2 is reduced, and the siRNA comprises the nucleotide sequence of SEQ ID NO: 1 in the sense strand and the nucleotide sequence of SEQ ID NO: 32 in the anti-sense strand.
6. The packaging and/or producer cell line according to embodiment 4, wherein expression of LINC00319 is reduced, and the siRNA comprises the nucleotide sequence of SEQ ID NO: 2 in the sense strand and the nucleotide sequence of SEQ ID NO: 33 in the anti-sense strand.
7. The packaging and/or producer cell line according to embodiment 4, wherein expression of CYP3A7 is reduced, and the siRNA comprises the nucleotide sequence of SEQ ID NO: 3 in the sense strand and the nucleotide sequence of SEQ ID NO: 34 in the anti-sense strand.
8. The packaging and/or producer cell line according to embodiment 4, wherein expression of NOG is reduced, and the siRNA comprises the nucleotide sequence of SEQ ID NO: 4 in the sense strand and the nucleotide sequence of SEQ ID NO: 35 in the anti-sense strand.
9. The packaging and/or producer cell line according to embodiment 4, wherein expression of SPANXN3 is reduced, and the siRNA comprises the nucleotide sequence of SEQ ID NO: 5 in the sense strand and the nucleotide sequence of SEQ ID NO: 36 in the anti-sense strand.
10. The packaging and/or producer cell line according to embodiment 4, wherein expression of MYRIP is reduced, and the siRNA comprises the nucleotide sequence of SEQ ID NO: 6 in the sense strand and the nucleotide sequence of SEQ ID NO: 37 in the anti-sense strand.
11. The packaging and/or producer cell line according to embodiment 4, wherein expression of KCNN2 is reduced, and the siRNA comprises the nucleotide sequence of SEQ ID NO: 7 in the sense strand and the nucleotide sequence of SEQ ID NO: 38 in the anti-sense strand.
12. The packaging and/or producer cell line according to embodiment 4, wherein expression of NALCN-AS1 is reduced, and the siRNA comprises the nucleotide sequence of SEQ ID NO: 8 in the sense strand and the nucleotide sequence of SEQ ID NO: 39 in the anti-sense strand.
13. The packaging and/or producer cell line according to embodiment 4, wherein expression of RGMA is reduced, and the siRNA comprises the nucleotide sequence of SEQ ID NO: 9 in the sense strand and the nucleotide sequence of SEQ ID NO: 40 in the anti-sense strand.
14. The packaging and/or producer cell line according to embodiment 4, wherein expression of PGA5 is reduced, and the siRNA comprises the sequence of SEQ ID NO: 10 in the sense strand and the sequence of SEQ ID NO: 41 in the anti-sense strand.
15. The packaging and/or producer cell line according to embodiment 4, wherein expression of ABCA10 is reduced, and the siRNA comprises the sequence of SEQ ID NO: 11 in the sense strand and the sequence of SEQ ID NO: 42 in the anti-sense strand.
16. The packaging and/or producer cell line according to embodiment 3, wherein the nuclease is selected from the group consisting of a Zinc Finger nuclease (ZFN), a meganuclease, a transcription activator-like effector nuclease (TALEN), or a clustered regularly interspaced short palindromic repeats (CRISPR) associated protein.
17. The packaging and/or producer cell line according to one of embodiments 1-16, wherein the expression is reduced using CRISPR genome editing.
18. The packaging and/or producer cell line according to embodiment 17, wherein the expression is reduced using a guide RNA pair, wherein each guide RNA:
    (a) comprises a sequence selected from the nucleotide sequences of SEQ ID NOs: 12-15, and/or
    (b) targets a target DNA sequence selected from any one of the nucleotide sequences of SEQ ID NO: 16-31.
19. The packaging and/or producer cell line according to embodiment 18, wherein the gRNA pair is used to target KCNN2 and comprises a first gRNA molecule comprising the sequence of SEQ ID NO: 12 and a second gRNA molecule comprising the sequence of SEQ ID NO: 13.
20. The packaging and/or producer cell line according to embodiment 18, wherein the gRNA pair is used to target KCNN2 and comprises a first gRNA molecule comprising the sequence of SEQ ID NO: 14 and a second gRNA molecule comprising the sequence of SEQ ID NO: 15.
21. The packaging and/or producer cell line of embodiment 19 or 20, wherein each gRNA molecule is a 2'O-methyl analog comprising 3' phosphorothioate internucleotide linkages in the terminal three nucleotides on either or both its 5' and 3' ends.
22. The packaging and/or producer cell line according to any one of embodiments 1-21, wherein the gene expression is eliminated compared to control parental cells.
23. The packaging and/or producer cell line according to any one of embodiments 1-22, wherein the cell line is a human cell line.
24. The packaging and/or producer cell line according to embodiment 23, wherein the human cell line is a HeLa cell line or a human embryonic kidney (HEK) 293 cell line.
25. The cell line according to any one of embodiments 1-24, wherein the cell line is a rAAV packaging cell line.
26. The cell line according to any one of embodiments 1-24, wherein the cell line is a rAAV producer cell line.
27. The cell line according to embodiment 26, wherein the titer of rAAV is increased about 1.5 to about 7 fold compared to the titer of rAAV produced from a cell line comprising the control parental cells.
28. A lysate of the cell line according to any one of embodiments 1-27.

29. A cell culture supernatant from a cell line according to any one of embodiments 1-27.

30. A method of generating a producer cell line, the method comprising delivering a recombinant adeno-associated virus (rAAV) vector to cells of a packaging cell line according to embodiment 25.

31. A method of producing rAAV, the method comprising infecting the cells of a producer cell line generated by the method of embodiment 30 with a helper virus.

32. A method of producing rAAV, the method comprising infecting the cells of a producer cell line according to embodiment 26 with a helper virus.

33. A method of embodiment 31 or 32, wherein the rAAV is harvested from the producer cell line.

34. A method of any one of embodiments 31 to 33, wherein the production of rAAV is enhanced as compared to a control parental cell line.

35. A method of identifying one or more genes relevant to the production of rAAV, the method comprising:

adding one or more supplements that increase the rAAV titer in a cell line;

measuring the global gene expression across the transcriptome in supplemented and non-supplemented cell lines;

obtaining a list of genes that are differentially expressed between supplemented and non-supplemented cell lines; and identifying one or more genes that are relevant to the production of rAAV.

36. The method of embodiment 35, wherein the one or more supplements added to the cell line comprise dexamethasone, hydrocortisone, prednisolone, methylprednisolone, betamethasone, cortisone, prednisone, budesonide, or triamcinolone.

37. A method of producing a rAAV packaging and/or producer cell line to promote increased production of rAAV, the method comprising modulating the expression of one or more genes identified using the method of embodiment 35.

38. The method of any one of embodiments 35-37, wherein the cell line is a rAAV packaging cell line.

39. The method of any one of embodiments 35-37, wherein the cell line is a rAAV producer cell line.

40. The method of embodiment 39, wherein the rAAV producer cell line increases rAAV titer at least 1.5 fold greater than the rAAV titer produced by a rAAV producer cell line without the modulation of expression of the corresponding one or more genes.

41. The method of any one of embodiments 37-40, wherein modulating the expression comprises reduction of expression of one or more genes.

42. The method of any one of embodiments 37-40, wherein modulating the expression comprises elimination of expression of one or more genes.

43. The method of any one of embodiments 30-42, wherein the cell line is a human cell line.

44. The method of embodiment 43, wherein the human cell line is a HeLa cell line or a human embryonic kidney (HEK) 293 cell line.

45. A recombinant adeno-associated virus (rAAV) packaging and/or producer cell line comprising cells which have been engineered to reduce the expression and/or activity of a gene product expressed from ATP5EP2, LINC00319, CYP3A7, ABCA10, NOG, RGMA, SPANXN3, PGA5, MYRIP, KCNN2, and/or NALCN-AS1 as compared to corresponding unmodified parental cells.

46. The rAAV packaging and/or producer cell line of embodiment 45, wherein the expression and/or activity of a gene product expressed from ATP5EP2, LINC00319, CYP3A7, ABCA10, NOG, RGMA, SPANXN3, PGA5, MYRIP, KCNN2, and/or NALCN-AS1 is reduced indefinitely or permanently.

47. The rAAV packaging and/or producer cell line of embodiment 46, wherein the cell line has been engineered to comprise a gene disruption or a partial or complete gene deletion in at least one of ATP5EP2, LINC00319, CYP3A7, ABCA10, NOG, RGMA, SPANXN3, PGA5, MYRIP, KCNN2, and/or NALCN-AS1.

48. The rAAV packaging and/or producer cell line of embodiment 47, wherein the cell line has been engineered to comprise a gene disruption in at least one of ATP5EP2, LINC00319, CYP3A7, ABCA10, NOG, RGMA, SPANXN3, PGA5, MYRIP, KCNN2, and/or NALCN-AS1.

49. The rAAV packaging and/or producer cell line of embodiment 47, wherein the cell line has been engineered to comprise a gene disruption in at least two genes selected from ATP5EP2, LINC00319, CYP3A7, ABCA10, NOG, RGMA, SPANXN3, PGA5, MYRIP, KCNN2, and NALCN-AS1.

50. The rAAV packaging and/or producer cell line of embodiment 47, wherein the cell line has been engineered to comprise a partial or complete gene deletion in at least one of ATP5EP2, LINC00319, CYP3A7, ABCA10, NOG, RGMA, SPANXN3, PGA5, MYRIP, KCNN2, and/or NALCN-AS1.

51. The rAAV packaging and/or producer cell line of embodiment 47, wherein the cell line has been engineered to comprise a partial or complete gene deletion in at least two genes selected from ATP5EP2, LINC00319, CYP3A7, ABCA10, NOG, RGMA, SPANXN3, PGA5, MYRIP, KCNN2, and NALCN-AS1.

52. A recombinant adeno-associated virus (rAAV) packaging and/or producer cell line, wherein said cell line exhibits reduced expression and/or activity of a polypeptide or polyribonucleotide expressed from at least one of ATP5EP2, LINC00319, CYP3A7, ABCA10, NOG, RGMA, SPANXN3, PGA5, MYRIP, KCNN2, and NALCN-AS1 as compared to a corresponding parental cell line.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

What is claimed is:

1. A recombinant adeno-associated virus (rAAV) packaging and/or producer cell line comprising a plurality of engineered cells which have reduced expression of a gene product expressed from Potassium Calcium-Activated Channel Subfamily N Member 2 (KCNN2) as compared to corresponding unmodified parental cells.

2. The rAAV packaging and/or producer cell line according to claim 1, wherein the plurality of engineered cells further have reduced expression of a gene product expressed from Repulsive Guidance Molecule BMP Co-Receptor A (RGMA), ATP Synthase F1 Subunit Epsilon Pseudogene 2 (ATP5EP2), Long Intergenic Non-Protein Coding RNA 319 (LINC00319), Cytochrome P450 Family 3 Subfamily A Member 7 (CYP3A7), ATP Binding Cassette Subfamily A Member 10 (ABCA10), Noggin (NOG), SPANX Family Member N3 (SPANXN3), Pepsinogen A5 (PGA5), Myosin VIIA And Rab Interacting Protein (MYRIP), and/or NALCN Antisense RNA 1 (NALCN-AS1) compared to corresponding unmodified parental cells.

3. The rAAV packaging and/or producer cell line of claim 2, wherein the plurality of engineered cells comprise a gene disruption in at least one of Repulsive Guidance Molecule BMP Co-Receptor A (RGMA), ATP Synthase F1 Subunit Epsilon Pseudogene 2 (ATP5EP2), Long Intergenic Non-Protein Coding RNA 319 (LINC00319), Cytochrome P450 Family 3 Subfamily A Member 7 (CYP3A7), ATP Binding Cassette Subfamily A Member 10 (ABCA10), Noggin (NOG), SPANX Family Member N3 (SPANXN3), Pepsinogen A5 (PGA5), Myosin VIIA And Rab Interacting Protein (MYRIP), and NALCN Antisense RNA 1 (NALCN-AS1).

4. The rAAV packaging and/or producer cell line of claim 2, wherein the plurality of engineered cells comprise a partial gene deletion in at least one of Repulsive Guidance Molecule BMP Co-Receptor A (RGMA), ATP Synthase F1 Subunit Epsilon Pseudogene 2 (ATP5EP2), Long Intergenic Non-Protein Coding RNA 319 (LINC00319), Cytochrome P450 Family 3 Subfamily A Member 7 (CYP3A7), ATP Binding Cassette Subfamily A Member 10 (ABCA10), Noggin (NOG), SPANX Family Member N3 (SPANXN3), Pepsinogen A5 (PGA5), Myosin VIIA And Rab Interacting Protein (MYRIP), and NALCN Antisense RNA 1 (NALCN-AS1).

5. The rAAV packaging and/or producer cell line of claim 2, wherein the plurality of engineered cells comprise a complete gene deletion in at least one of Repulsive Guidance Molecule BMP Co-Receptor A (RGMA), ATP Synthase F1 Subunit Epsilon Pseudogene 2 (ATP5EP2), Long Intergenic Non-Protein Coding RNA 319 (LINC00319), Cytochrome P450 Family 3 Subfamily A Member 7 (CYP3A7), ATP Binding Cassette Subfamily A Member 10 (ABCA10), Noggin (NOG), SPANX Family Member N3 (SPANXN3), Pepsinogen A5 (PGA5), Myosin VIIA And Rab Interacting Protein (MYRIP), and NALCN Antisense RNA 1 (NALCN-AS1).

6. The rAAV packaging and/or producer cell line of claim 1, wherein the cell line is a HeLa cell line or a human embryonic kidney (HEK) 293 cell line.

7. The rAAV packaging and/or producer cell line according to claim 1, wherein the expression of KCNN2 in the plurality of engineered cells has been reduced using
 a) a nuclease selected from the group consisting of a Zinc Finger nuclease (ZFN), a meganuclease, a transcription activator-like effector nuclease (TALEN), and a clustered regularly interspaced short palindromic repeats (CRISPR) associated protein, or
 b) CRISPR genome editing.

8. The rAAV packaging and/or producer cell line according to claim 1, wherein the expression of KCNN2 in the plurality of engineered cells has been reduced using a guide RNA (gRNA) pair, wherein each gRNA:
 (a) comprises a sequence selected from the nucleotide sequences of SEQ ID NOs: 12-15, and/or
 (b) targets a target DNA sequence selected from any one of the nucleotide sequences of SEQ ID NOs: 16-19.

9. The rAAV packaging and/or producer cell line of claim 8, wherein each gRNA molecule is a 2' O-methyl analog comprising 3' phosphorothioate internucleotide linkages in the terminal three nucleotides on either or both its 5' and 3' ends.

10. The rAAV packaging and/or producer cell line according to claim 1, wherein the gene expression of KCNN2 in the plurality of engineered cells is eliminated compared to corresponding unmodified parental cells.

11. The rAAV packaging and/or producer cell line according to claim 1, wherein the cell line is a rAAV packaging cell line.

12. The rAAV packaging and/or producer cell line according to claim 1, wherein the cell line is a rAAV producer cell line.

13. A lysate of the rAAV producer cell line or a cell culture supernatant from a rAAV producer cell line according to claim 12.

14. A method of generating a producer cell line, the method comprising delivering a recombinant adeno-associated virus (rAAV) vector to the plurality of cells of the rAAV packaging cell line according to claim 11.

15. A method of producing rAAV, the method comprising infecting the cells of a rAAV producer cell line generated by the method of claim 14 with a helper virus.

16. The method of claim 15, wherein the production of rAAV is enhanced as compared to a control parental cell line.

17. The method of claim 15, wherein the cell line is a HeLa cell line or a human embryonic kidney (HEK) 293 cell line.

* * * * *